000
(12) United States Patent
Wu

(10) Patent No.: US 11,931,420 B2
(45) Date of Patent: Mar. 19, 2024

(54) COMBINATION THERAPIES USING AN ANTI-BCMA ANTIBODY DRUG CONJUGATE (ADC) IN COMBINATION WITH A GAMMA SECRETASE INHIBITOR (GSI)

(71) Applicant: CELGENE CORPORATION, Summit, NJ (US)

(72) Inventor: Kaida Wu, Watertown, MA (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 17/733,327

(22) Filed: Apr. 29, 2022

(65) Prior Publication Data

US 2022/0401569 A1 Dec. 22, 2022

Related U.S. Application Data

(60) Provisional application No. 63/182,598, filed on Apr. 30, 2021.

(51) Int. Cl.
*A61K 47/68* (2017.01)
*A61K 31/55* (2006.01)
*A61P 35/02* (2006.01)
*C07K 16/28* (2006.01)
*A61K 39/00* (2006.01)

(52) U.S. Cl.
CPC .......... *A61K 47/6803* (2017.08); *A61K 31/55* (2013.01); *A61K 47/6849* (2017.08); *A61K 47/6889* (2017.08); *A61P 35/02* (2018.01); *C07K 16/2878* (2013.01); *C07K 16/2896* (2013.01); *A61K 2039/505* (2013.01); *A61K 2039/545* (2013.01)

(58) Field of Classification Search
None
See application file for complete search history.

(56) References Cited

U.S. PATENT DOCUMENTS

| 4,289,872 A | 9/1981 | Denkewalter et al. |
| 4,486,414 A | 12/1984 | Pettit |
| 4,542,225 A | 9/1985 | Blattler et al. |

(Continued)

FOREIGN PATENT DOCUMENTS

| EP | 0606046 A1 | 7/1994 |
| EP | 0780386 A1 | 6/1997 |

(Continued)

OTHER PUBLICATIONS

ClinicalTrials.gov Identifier: NCT04036461, A Study of CC-99712, a BCMA Antibody-Drug Conjugate, in Participants With Relapsed and Refractory Multiple Myeloma, 2019, downloaded Jun. 2, 2023 from https://clinicaltrials.gov/ct2/show/NCT04036461 (Year: 2019).*

(Continued)

*Primary Examiner* — Karl J Puttlitz
(74) *Attorney, Agent, or Firm* — JONES DAY

(57) ABSTRACT

The present disclosure relates to methods of using antibody conjugates with binding specificity for BCMA (BCMA) and its isoforms and homologs in combination with a gamma secretase inhibitor (GSI), such as in therapeutic methods. Also provided are pharmaceutical compositions and kits comprising the antibody conjugates and GSI.

25 Claims, 2 Drawing Sheets

Specification includes a Sequence Listing.

(56) References Cited

U.S. PATENT DOCUMENTS

| | | | |
|---|---|---|---|
| 4,618,492 | A | 10/1986 | Blattler et al. |
| 4,625,014 | A | 11/1986 | Senter et al. |
| 4,816,444 | A | 3/1989 | Pettit et al. |
| 4,879,278 | A | 11/1989 | Pettit et al. |
| 4,978,744 | A | 12/1990 | Pettit et al. |
| 4,986,988 | A | 1/1991 | Pettit et al. |
| 5,076,973 | A | 12/1991 | Pettit et al. |
| 5,138,036 | A | 8/1992 | Pettit et al. |
| 5,229,490 | A | 7/1993 | Tam |
| 5,410,024 | A | 4/1995 | Pettit et al. |
| 5,504,191 | A | 4/1996 | Pettit et al. |
| 5,521,284 | A | 5/1996 | Pettit et al. |
| 5,530,097 | A | 6/1996 | Pettit et al. |
| 5,554,725 | A | 9/1996 | Pettit |
| 5,599,902 | A | 2/1997 | Pettit et al. |
| 5,635,483 | A | 6/1997 | Pettit et al. |
| 5,643,575 | A | 7/1997 | Martinez et al. |
| 5,663,149 | A | 9/1997 | Pettit et al. |
| 5,665,860 | A | 9/1997 | Pettit et al. |
| 5,780,588 | A | 7/1998 | Pettit et al. |
| 5,861,510 | A | 1/1999 | Piscopio et al. |
| 5,863,949 | A | 1/1999 | Robinson et al. |
| 5,932,462 | A | 8/1999 | Harris et al. |
| 6,034,065 | A | 3/2000 | Pettit et al. |
| 6,239,104 | B1 | 5/2001 | Pettit et al. |
| 6,323,315 | B1 | 11/2001 | Pettit et al. |
| 7,375,078 | B2 | 5/2008 | Feng |
| 8,431,558 | B2 | 4/2013 | Bertozzi et al. |
| 8,703,936 | B2 | 4/2014 | Jewett et al. |
| 9,145,361 | B2 | 9/2015 | Gee et al. |
| 9,222,940 | B2 | 12/2015 | van Delft et al. |
| 10,000,571 | B2 | 6/2018 | Ashkenazi et al. |
| 10,000,576 | B1 | 6/2018 | Weisser et al. |
| 10,005,844 | B2 | 6/2018 | Siebel et al. |
| 10,072,088 | B2 | 9/2018 | Pillarisetti et al. |
| 10,465,009 | B2 | 11/2019 | Armitage et al. |
| 10,683,369 | B2 | 6/2020 | Vu et al. |
| 2003/0083263 | A1 | 5/2003 | Doronina et al. |
| 2003/0143596 | A1 | 7/2003 | Bentley et al. |
| 2005/0009751 | A1 | 1/2005 | Senter et al. |
| 2005/0238649 | A1 | 10/2005 | Doronina et al. |
| 2013/0189287 | A1 | 7/2013 | Bregeon et al. |
| 2013/0251783 | A1 | 9/2013 | Parmentier et al. |
| 2014/0356385 | A1 | 12/2014 | Dennler et al. |
| 2019/0040152 | A1 | 2/2019 | Kinneer et al. |
| 2019/0083641 | A1 | 3/2019 | Stafford et al. |
| 2021/0130483 | A1 | 5/2021 | Yam et al. |
| 2022/0323599 | A1 | 10/2022 | Lee et al. |
| 2022/0362394 | A1 | 11/2022 | Lee et al. |

FOREIGN PATENT DOCUMENTS

| | | | |
|---|---|---|---|
| EP | | 0606046 B1 | 10/1997 |
| EP | | 0931788 A2 | 7/1999 |
| EP | | 0931788 A3 | 7/1999 |
| EP | | 0818442 A2 | 5/2000 |
| EP | | 0818442 A3 | 5/2000 |
| EP | | 1004578 A2 | 5/2000 |
| EP | | 1004578 A3 | 5/2000 |
| EP | | 0780386 B1 | 2/2002 |
| EP | | 0931788 B1 | 11/2002 |
| EP | | 1004578 B1 | 2/2004 |
| WO | WO 1990005719 A1 | | 5/1990 |
| WO | WO 1993021259 A1 | | 10/1993 |
| WO | WO 1996021469 A1 | | 7/1996 |
| WO | WO 1996027583 A1 | | 9/1996 |
| WO | WO 1996033172 A1 | | 10/1996 |
| WO | WO 1997022596 A1 | | 6/1997 |
| WO | WO 1997030035 A1 | | 8/1997 |
| WO | WO 1997032856 A1 | | 9/1997 |
| WO | WO 1998003516 A1 | | 1/1998 |
| WO | WO 1998033768 A1 | | 1/1998 |
| WO | WO 1998007697 A1 | | 2/1998 |
| WO | WO 1998013354 A1 | | 4/1998 |
| WO | WO 1998030566 A1 | | 7/1998 |
| WO | WO 1998034915 A1 | | 8/1998 |
| WO | WO 1998034918 A1 | | 8/1998 |
| WO | WO 1999007675 A1 | | 2/1999 |
| WO | WO 1999029667 A1 | | 6/1999 |
| WO | WO 1999052889 A1 | | 10/1999 |
| WO | WO 1999052910 A1 | | 10/1999 |
| WO | WO 2002088172 A2 | | 11/2002 |
| WO | WO 2002088172 A3 | | 11/2002 |
| WO | WO 2004010957 A2 | | 2/2004 |
| WO | WO 2004010957 A3 | | 2/2004 |
| WO | WO 2014089335 A2 | | 6/2014 |
| WO | WO 2014089335 A3 | | 6/2014 |
| WO | WO 2015166073 A1 | | 11/2015 |
| WO | WO 2016090327 A2 | | 6/2016 |
| WO | WO 2016123582 A1 | | 8/2016 |
| WO | WO 2016166629 A1 | | 12/2016 |
| WO | WO 2017087901 A2 | | 5/2017 |
| WO | WO 2017087901 A3 | | 5/2017 |
| WO | WO 2017132615 A1 | | 8/2017 |
| WO | WO 2017132617 A1 | | 8/2017 |
| WO | WO 2018201051 A1 | | 11/2018 |
| WO | WO 2019023316 A1 | | 1/2019 |
| WO | WO 2019055909 A1 | | 3/2019 |
| WO | WO 2019055931 A1 | | 3/2019 |
| WO | WO 2019190969 A1 | | 10/2019 |
| WO | 2020227105 | * | 11/2020 |
| WO | WO 2020227105 A1 | | 11/2020 |
| WO | WO 2020227110 A1 | | 11/2020 |
| WO | WO 2020252015 A1 | | 12/2020 |

OTHER PUBLICATIONS

Investor Village, downloaded May 30, 2023 from https://www.investorvillage.com/smbd.asp?mb=4235&mn=3391&pt=msg&mid=20900430 2020 (Year: 2020).*

National Cancer Institute Drug Dictionary, Crenigacestat, downloaded May 30, 2023 from https://www.cancer.gov/publications/dictionaries/cancer-drug/def/crenigacestat?redirect=true 2023 (Year: 2023).*

Newman, J. Nat. Prod. 2021, 84, 3, 917-931 (Year: 2021).*

Alley et al., 2010, "Antibody-drug conjugates: targeted drug delivery for cancer," Curr. Opin. Chem. Biol., 14(4):529-537.

Amsberry et al., 1990, "The lactonization of 2'-hydroxyhydrocinnamic acid amides: a potential prodrug for amines," J. Org. Chem., 55(23):5867-5877.

Avery et al., 2003, "BAFF selectively enhances the survival of plasmablasts generated from human memory B cells," J. Clin. Invest., 112(2):286-297.

Cai et al., 2015, "A simplified and robust protocol for immunoglobulin expression in *Escherichia coli* cell-free protein synthesis systems," Biotechnol Prog., 31(3):823-831.

Chilosi et al., 1999, "CD138/syndecan-1: a useful immunohistochemical marker of normal and neoplastic plasma cells on routine trephine bone marrow biopsies," Mod. Pathol., 12(12):1101-1106.

ClinicalTrials.gov Identifier: NCT03502577 v01, "BCMA-Specific CAR T-Cells Combined With a Gamma Secretase Inhibitor (LY3039478) to Treat Relapsed or Persistent Multiple Myeloma," last update posted on Apr. 18, 2018 (10 pages).

ClinicalTrials.gov Identifier: NCT03502577 v03, "BCMA-Specific CAR T-Cells Combined With a Gamma Secretase Inhibitor (LY3039478) to Treat Relapsed or Persistent Multiple Myeloma," first posted on Apr. 18, 2018, last update posted on Jun. 20, 2018 (10 pages).

ClinicalTrials.gov Identifier: NCT03502577 v14, "BCMA-Specific CAR T-Cells Combined With a Gamma Secretase Inhibitor (JSMD194) to Treat Relapsed or Persistent Multiple Myeloma," first posted on Apr. 18, 2018, last update posted on Aug. 2, 2021 (10 pages).

Cowan et al., 2019, "Efficacy and Safety of Fully Human Bcma Car T Cells in Combination with a Gamma Secretase Inhibitor to Increase Bcma Surface Expression in Patients with Relapsed or Refractory Multiple Myeloma," Blood, 134 (Supplement1):204 (4 pages).

Darce et al., 2007, "Divergent effects of BAFF on human memory B cell differentiation into Ig-secreting cells," J. Immunol., 178(9):5612-5622.

(56) References Cited

OTHER PUBLICATIONS

Dimasi et al., 2017, "Efficient Preparation of Site-Specific Antibody-Drug Conjugates Using Cysteine Insertion," Mol. Pharm., 14(5):1501-1516.
Dreier et al., 2011, "Ribosome display: a technology for selecting and evolving proteins from large libraries," Methods Mol. Biol., 687:283-306.
Hamann, 2005, "Monoclonal antibody-drug conjugates," Expert Opinion on Therapeutic Patents, 15(9):1087-1103.
Hanes et al., 1997, "In vitro selection and evolution of functional proteins by using ribosome display," Proc. Natl. Acad. Sci. USA, 94(10):4937-4942.
Hay et al., 1999, "A 2-nitroimidazole carbamate prodrug of 5-amimo-1-(chloromethyl)-3-[(5,6,7- trimethoxyindol-2-yl)carbony 1]-1,2-dihydro-3H--benz[E]indole (amino-seco-CBI-TMI) for use with ADEPT and GDEPT," Bioorg. Med. Chem. Lett., 9(15):2237-2242.
Heckman et al., 2007, "Gene splicing and mutagenesis by PCR-driven overlap extension," Nat. Protoc., 2(4):924-932.
Hengeveld et al., 2015, "B-cell activating factor in the pathophysiology of multiple myeloma: a target for therapy?" Blood Cancer J., 5(2):e282 (8 pages).
International Searching Authority, International Search Report and Written Opinion for International Patent Application No. PCT/US2020/031052 (Pub No. WO 2020227105) dated Sep. 9, 2020 (17 pages).
International Searching Authority, International Search Report and Written Opinion for International Patent Application No. PCT/US2020/031067 (Pub No. WO 2020227110) dated Jul. 24, 2020 (15 pages).
International Searching Authority, International Search Report and Written Opinion for International Patent Application No. PCT/US2022/026899 dated Jul. 19, 2022 (16 pages).
Kingsbury et al., 1984, "A novel peptide delivery system involving peptidase activated prodrugs as antimicrobial agents. Synthesis and biological activity of peptidyl derivatives of 5-fluorouracil," J. Med. Chem., 27(11):1447-1451.
Kivi et al., 2016, "HybriFree: a robust and rapid method for the development of monoclonal antibodies from different host species," BMC Biotechnol., 16:2 (14 pages).
Kumar et al., 2016, "International Myeloma Working Group consensus criteria for response and minimal residual disease assessment in multiple myeloma," Lancet. Oncol., 17(8):e328-e346.
Kuramochi et al., 2014, "Humanization and simultaneous optimization of monoclonal antibody," Methods Mol. Biol., 1060:123-137.
Marks et al., 2004, "Selection of human antibodies from phage display libraries," Methods Mol. Biol., 248:161-176.
O'Connor et al., 2004, "BCMA is essential for the survival of long-lived bone marrow plasma cells," J. Exp. Med., 199(1):91-98.
Phipps et al., 2015, "Daratumumab and its potential in the treatment of multiple myeloma: overview of the preclinical and clinical development," Ther. Adv. Hematol., 6(3):120-127.
Pont et al., 2019, "γ-Secretase inhibition increases efficacy of BCMA-specific chimeric antigen receptor T cells in multiple myeloma," Blood, 134(19):1585-1597.
Rajan et al., 2012, "Simplified synthetic antibody libraries," Methods Enzymol., 502:3-23.
Rodrigues et al., 1995, "Synthesis and beta-lactamase-mediated activation of a cephalosporin-taxol prodrug," Chem. Biol., 2(4):223-227.
Stafford et al., 2014, "In vitro Fab display: a cell-free system for IgG discovery," Protein Eng. Des. Sel., 27(4):97-109.
Storm et al., 1972, "Effect of small changes in orientation on reaction rate," J. Am. Chem. Soc., 94(16):5815-5825.
Tai et al., 2014, "Novel anti-B-cell maturation antigen antibody-drug conjugate (GSK2857916) selectively induces killing of multiple myeloma," Blood, 123(20):3128-3138.
Thompson et al., 2016, "Rational design, biophysical and biological characterization of site-specific antibody-tubulysin conjugates with improved stability, efficacy and pharmacokinetics," J. Control Release, 236:100-116.
Trudel et al., 2018, "Targeting B-cell maturation antigen with GSK2857916 antibody-drug conjugate in relapsed or refractory multiple myeloma (BMA117159): a dose escalation and expansion phase 1 trial," Lancet Oncol., 19(12):1641-1653.
Trudel et al., 2019, "Antibody-drug conjugate, GSK2857916, in relapsed/refractory multiple myeloma: an update on safety and efficacy from dose expansion phase I study," Blood Cancer J., 9(4):37 (10 pages).
Xu et al., 2001, "B-cell maturation protein, which binds the tumor necrosis factor family members BAFF and APRIL, is dispensable for humoral immune responses," Mol. Cell Biol., 21(12):4067-4074.
Yin et al., 2012, "Aglycosylated antibodies and antibody fragments produced in a scalable in vitro transcription-translation system," MAbs, 4(2):217-225.
Zimmerman et al., 2014, "Production of site-specific antibody-drug conjugates using optimized non-natural amino acids in a cell-free expression system," Bioconjug. Chem., 25(2):351-361.
Chen et al., 1995, "Enhancement and destruction of antibody function by somatic mutation: unequal occurrence is controlled by V gene combinatorial associations," EMBO J., 14(12):2784-2794.
ClinicalTrials.gov Identifier: NCT04036461 v1, "A Phase 1, Multicenter, Open-label, Dose Finding Study of CC-99712, a BCMA Antibody-Drug Conjugate, in Subjects With Relapsed and Refractory Multiple Myeloma," first posted Jul. 29, 2019, last update posted Jul. 29, 2019 (9 pages).
ClinicalTrials.gov Identifier: NCT04036461 v2, "A Phase 1, Multicenter, Open-label, Dose Finding Study of CC-99712, a BCMA Antibody-Drug Conjugate, in Subjects With Relapsed and Refractory Multiple Myeloma," first posted Jul. 29, 2019, last update posted Nov. 1, 2019 (10 pages).
ClinicalTrials.gov Identifier: NCT04036461 v3, "A Phase 1, Multicenter, Open-label, Dose Finding Study of CC-99712, a BCMA Antibody-Drug Conjugate, in Subjects With Relapsed and Refractory Multiple Myeloma," first posted Jul. 29, 2019, last update posted Dec. 20, 2019 (10 pages).
ClinicalTrials.gov Identifier: NCT04036461 v4, "A Phase 1, Multicenter, Open-label, Dose Finding Study of CC-99712, a BCMA Antibody-Drug Conjugate, in Subjects With Relapsed and Refractory Multiple Myeloma," first posted Jul. 29, 2019, last update posted Apr. 9, 2020 (10 pages).
ClinicalTrials.gov Identifier: NCT04036461 v5, "A Phase 1, Multicenter, Open-label, Dose Finding Study of CC-99712, a BCMA Antibody-Drug Conjugate, in Subjects With Relapsed and Refractory Multiple Myeloma," first posted Jul. 29, 2019, last update posted Aug. 31, 2020 (10 pages).
ClinicalTrials.gov Identifier: NCT04036461 v6, "A Phase 1, Multicenter, Open-label, Dose Finding Study of CC-99712, a BCMA Antibody-Drug Conjugate, in Subjects With Relapsed and Refractory Multiple Myeloma," first posted Jul. 29, 2019, last update posted Jan. 6, 2021 (10 pages).
ClinicalTrials.gov Identifier: NCT04036461 v7, "A Phase 1, Multicenter, Open-label, Dose Finding Study of CC-99712, a BCMA Antibody-Drug Conjugate, in Subjects With Relapsed and Refractory Multiple Myeloma," first posted Jul. 29, 2019, last update posted Feb. 17, 2021 (10 pages).
ClinicalTrials.gov Identifier: NCT04036461 v8, "A Phase 1, Multicenter, Open-label, Dose Finding Study of CC-99712, a BCMA Antibody-Drug Conjugate, in Subjects With Relapsed and Refractory Multiple Myeloma," first posted Jul. 29, 2019, last update posted Aug. 18, 2021 (11 pages).
Fellouse et al., 2007, "High-throughput generation of synthetic antibodies from highly functional minimalist phage-displayed libraries," J. Mol. Biol., 373(4):924-940.
Herold et al., 2017, "Determinants of the assembly and function of antibody variable domains," Sci. Rep., 7(1):12276 (17 pages).

(56) References Cited

OTHER PUBLICATIONS

International Searching Authority, International Search Report and Written Opinion for International Patent Application No. PCT/US2019/023844 (Pub No. WO 2019190969) dated Sep. 3, 2019 (17 pages).

Kranz et al., 1981, "Restricted reassociation of heavy and light chains from hapten-specific monoclonal antibodies," Proc. Natl. Acad. Sci. USA, 78(9):5807-5811.

Lamminmaki et al., 2001, "Crystal structure of a recombinant anti-estradiol Fab fragment in complex with 17beta-estradiol," J. Biol. Chem., 276(39):36687-36694.

MacCallum et al., 1996, "Antibody-antigen interactions: contact analysis and binding site topography," J. Mol. Biol., 262(5):732-745.

Mohan et al., 2021, "Risk of Infections with BCMA-Directed Immunotherapy in Multiple Myeloma," Blood, 138(Supp 1):1626.

Mohyuddin et al., 2021, "Rethinking mechanisms of neurotoxicity with BCMA directed therapy," Crit. Rev. Oncol. Hematol., 166:103453 (5 pages).

Nezlin, 1970, "Chapter IV—The Structure of Antibodies," in Biochemistry of Antibodies, Springer, Boston, MA, pp. 127-208.

Sidhu et al., 2004, "Phage-displayed antibody libraries of synthetic heavy chain complementarity determining regions," J. Mol. Biol., 338(2):299-310.

\* cited by examiner

COMBINATION THERAPIES USING AN ANTI-BCMA ANTIBODY DRUG CONJUGATE (ADC) IN COMBINATION WITH A GAMMA SECRETASE INHIBITOR (GSI)

CROSS-REFERENCE TO RELATED APPLICATIONS

This application claims the benefit of U.S. Provisional Application No. 63/182,598, filed Apr. 30, 2021, which is incorporated by reference herein in its entirety.

REFERENCE TO SEQUENCE LISTING SUBMITTED ELECTRONICALLY

This application incorporates by reference a Sequence Listing submitted with this application as text file entitled 14247-660-999_SEQ_LISTING.txt created on Apr. 15, 2022 and having a size of 30,224 bytes.

FIELD OF THE INVENTION

Provided herein are methods of using antibody conjugates with binding specificity for B-cell maturation antigen (BCMA) in combination with a gamma secretase inhibitor (GSI), such as in therapeutic methods. Also provided herein are pharmaceutical compositions and kits comprising the antibody conjugates and a gamma secretase inhibitor (GSI). The methods of using the conjugates and compositions are useful, for example, in methods of treatment and prevention of cell proliferation and cancer, such as multiple myeloma (e.g., relapsed or refractory multiple myeloma).

BACKGROUND

B-cell maturation antigen (BCMA) is a member of the tumor necrosis factor (TNF) receptor superfamily which recognizes B-cell activating factor. The protein in humans is encoded by the tumor necrosis factor receptor superfamily member 17 (TNFRSF17) gene and is preferentially expressed in mature B lymphocytes.

BCMA plays an important role in regulating B-cell maturation and differentiation into plasma cells. It is closely related to BAFF receptor (BAFF-R) and transmembrane activator and calcium modulator and cyclophilin ligand interactor (TACI). While BCMA, BAFF-R, and TACI are type III transmembrane proteins that promote B-cell survival at distinct stages of development, BCMA is expressed exclusively in B-cell lineage cells, such as, for example, plasmablasts and differentiated plasma cells (Avery et al. (2003) *J. Clin. Invest.* 112(2):286-297; O'Connor et al. (2004) *J Exp. Med.* 199(1):91-98). It is selectively induced during plasma cell differentiation, which occurs concurrently with loss of BAFF-R expression in the differentiated cells (Darce et al. (2007) *J. Immunol.* 178(9):5612-5622). BCMA expression appears to support the survival of normal plasma cells and plasmablasts but is typically absent on naïve and most memory B cells. Thus, it does not appear to be needed for overall B-cell homeostasis but is required for optimal survival of long-lived plasma cells in the bone marrow (O'Connor et al. (2004) supra; Xu, S. and K. P. Lam (2001)*Mol. Cell. Biol.* 21(12):4067-4074).

In multiple myeloma, BCMA has been shown to be universally and widely expressed in malignant plasma cells at elevated levels; however, it is typically undetected on normal human tissues except for plasma cells. Due to its selective expression as a cell-surface receptor on multiple myeloma cell lines, BCMA can potentially be targeted in therapies to treat multiple myeloma. BCMA expression is also associated with leukemia and lymphoma. Accordingly, there is a need for improved methods of targeting and/or modulating the activity of BCMA. Given the specific expression of BCMA on plasma cells and lower expression in non-cancer tissue, there is a need for improved therapeutics that can specifically target cells and tissues that express or overexpress BCMA. Antibody conjugates to BCMA could be used to deliver therapeutic or diagnostic payload moieties to target cells expressing BCMA for the treatment or diagnosis of such diseases.

SUMMARY

Provided herein are methods of using antibody conjugates that selectively bind B-cell maturation antigen (BCMA) (e.g., Conjugate 4) in combination with a gamma secretase inhibitor (GSI) (e.g. BMS-986405), such as in therapeutic methods. The antibody conjugates comprise an antibody, that binds BCMA, linked to one or more payload moieties. The antibody is linked to the payload by way of a linker. BCMA antibodies are described in detail herein, as are useful payload moieties, and useful linkers. Likewise, GSIs, such as BMS-986405, are described in detail herein.

In some embodiments, the methods are methods of delivering one or more payload moieties to a target cell or tissue expressing BCMA. In some embodiments, the methods are methods of treatment. In some embodiments, the antibody conjugates are used to treat a disease or condition. In some embodiments, the disease or condition is a cancer, for example, multiple myeloma.

In another aspect, provided herein are kits comprising the antibody conjugates and GSIs.

In some embodiments, the antibody conjugates bind human BCMA. In some embodiments, the antibody conjugates also bind homologs of human BCMA. In some aspects, the antibody conjugates also bind cynomolgus monkey and/or mouse BCMA.

In certain embodiments, provided herein is a method of treating or preventing cancer in a subject in need thereof, comprising administering to the subject: a) an effective amount of an antibody conjugate according to the formula:

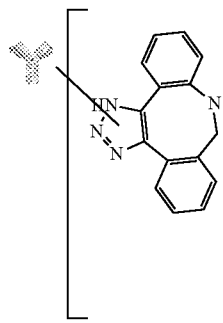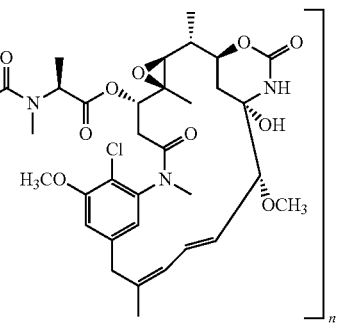

wherein n is from 1 to 4; the antibody comprises a $V_H$ region of SEQ ID NO: 13, and a $V_L$ region of SEQ ID NO: 14; the antibody further comprises a heavy chain constant region comprising residue of p-azidomethyl-phenylalanine substituting at each of sites HC-F404 and HC-Y180 according to the EU numbering scheme; and each structure within the brackets of the formula is bonded to the antibody at one of the p-azidomethyl-phenylalanine residues; and b) an effective amount of BMS-986405. In other embodiments, the antibody comprises (i) a $V_H$ region comprising a CDR1 comprising SEQ ID NO SEQ ID NO: 5 or 6; a CDR2 comprising SEQ ID NO: 7 or 8; a CDR3 comprising SEQ ID NO: 9; and (ii) a $V_L$ comprising a CDR1 comprising SEQ ID NO: 10; a CDR2 comprising SEQ ID NO: 11; and a CDR3 comprising SEQ ID NO: 12. In more specific embodiments, of the antibody conjugate, n is 1, 2, 3 or 4. In particular embodiments, the antibody conjugate further comprises at least one constant region domain. For example, in specific embodiments, the antibody conjugate comprise a human constant region domain, e.g. In yet other specific embodiments, the antibody conjugate comprises a constant region domain that comprises a human IgG1 heavy chain content region, a human IgG1 kappa light chain region, or a human IgG1 heavy chain constant region and a human IgG1 kappa light chain region. In a more specific embodiment of the antibody conjugate, the constant region comprises a sequence selected from SEQ ID NO: 19 and 20, or both SEQ ID NO: 19 and SEQ ID NO: 20. In other embodiments, the antibody conjugate comprises a heavy chain that comprises the amino acid sequence of SEQ ID NO: 15. For example, the antibody conjugate may comprise a heavy chain that comprises the amino acid sequence of SEQ ID NO: 15, wherein each of the amino acids corresponding to HC-F404 and HC-Y180 according to the EU numbering scheme have been substituted for a p-azidomethyl-phenylalanine residue. In other embodiments, the antibody conjugate comprises a light chain that comprises the amino acid sequence of SEQ ID NO: 17. In yet other embodiments, the antibody conjugate comprises a heavy chain that comprises the amino acid sequence of SEQ ID NO:15 and a light chain that comprises the amino acid sequence of SEQ ID NO: 17. For example, the antibody conjugate may comprise a heavy chain that comprises the amino acid sequence of SEQ ID NO:15 and a light chain that comprises the amino acid sequence of SEQ ID NO: 17, wherein each of the amino acids corresponding to heavy chain (HC)-F404 and HC-Y180 according to the EU numbering scheme have been substituted for a p-azidomethyl-phenylalanine residue.

In certain embodiments of any of the antibody conjugates provided herein, the antibody is a monoclonal antibody. In certain embodiments of any of the antibody conjugates provided herein, the antibody is an IgA, an IgD, an IgE, an IgG, or an IgM. In certain embodiments of any of the antibody conjugates provided herein, the antibody is humanized or human. In certain embodiments of any of the antibody conjugates provided herein, the antibody is aglycosylated. In certain embodiments of any of the antibody conjugates provided herein, the antibody is an antibody fragment, e.g., an Fv fragment, a Fab fragment, a F(ab')2 fragment, a Fab' fragment, an scFv (sFv) fragment, or an scFv-Fc fragment. In certain embodiments of any of the antibody conjugates provided herein the antibody specifically binds human BCMA and cynomolgus BCMA. In certain embodiments of any of the antibody conjugates provided herein, the antibody specifically binds human BCMA and mouse BCMA.

In certain embodiments, the amount of the antibody conjugate administered is about 0.3 mg/kg, 0.6 mg/kg, 1.0 mg/kg, 1.25 mg/kg, 1.5 mg/kg, 1.75 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.25 mg/kg, 4.5 mg/kg, 4.75 mg/kg, 5.0 mg/kg, 5.25 mg/kg, 5.5 mg/kg, 5.75 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.25 mg/kg, 7.5 mg/kg, 7.75 mg/kg, 8.0 mg/kg, 8.25 mg/kg, 8.5 mg/kg, 8.75 mg/kg, 9.0 mg/kg, 9.25 mg/kg, 9.5 mg/kg, 9.75 mg/kg, or 10.0 mg/kg of the subject's body weight. In certain embodiments, the GSI is BMS-986405. In particular embodiments, the amount of BMS-986405 administered is about 25 mg. In certain embodiments, the antibody conjugate is administered to the subject once every three weeks and the GSI, e.g., BMS-986405, is administered to the subject three times every week during a 21-day cycle. In certain embodiments, the antibody conjugate (e.g., Conjugate 4) is administered to the subject once every three weeks, wherein the every three weeks is the 21-day cycle (e.g., during which he gamma secretase inhibitor (GSI) (e.g., BMS-986405) is administered to the subject). In certain embodiments, the antibody conjugate (e.g., Conjugate 4) is administered to the subject on the first day (Day 1) of the 21-day cycle. In certain embodiments, the antibody conjugate (e.g., Conjugate 4) is administered to the subject on the first day (Day 1) of each 21-day cycle. In certain embodiments, the 21-day cycle occurs once, twice, three times, four times, five times, six times, seven times, eight times, nine times, ten times, eleven times, twelve times, thirteen times, fourteen times, or fifteen times. In certain embodiments, the effective amount of the antibody conjugate is administered to the subject on the first day (Day 1) of the 21-day cycle, and wherein the effective amount of the antibody conjugate is 0.3 mg/kg, 0.6 mg/kg, 1.25 mg/kg, 2.0 mg/kg, 3.0 mg/kg, 4.5 mg/kg, or 6.7 mg/kg. In certain embodiments, the effective amount of BMS-986405 is administered to the subject on Day 1, Day 3, Day 5, Day 8, Day 10, Day 12, Day 15, Day 17, and Day 19 of a 21-day cycle. In certain embodiments, the effective amount of the antibody conjugate is 0.3 mg/kg. In certain embodiments, the effective amount of the antibody conjugate is 0.6 mg/kg. In certain embodiments, the effective amount of the antibody conjugate is 1.25 mg/kg. In certain embodiments, the effective amount of the antibody conjugate is 2.0 mg/kg. In certain embodiments, the effective amount of the antibody conjugate is 3.0 mg/kg. In certain embodiments, the effective amount of the antibody conjugate is 4.5 mg/kg. In certain embodiments, the effective amount of the antibody conjugate is 6.7 mg/kg. In certain embodiments, the effective amount of BMS-986405 is about 25 mg. In certain embodiments, the antibody conjugate is administered intravenously. In certain embodiments, the GSI, e.g., BMS-986405 is administered orally, for example in capsule form.

In certain embodiments, the antibody conjugate is administered concurrently with the BMS-986405. In certain embodiments, the antibody conjugate is administered prior to the administration of the BMS-986405. In certain embodiments, the antibody conjugate is administered after the administration of the BMS-986405. In certain embodiments, the antibody conjugate and the BMS-986405 are administered to a subject on an empty stomach. In certain embodiments, the antibody conjugate and the BMS-986405 are administered to a subject on an full stomach.

In certain embodiments, the cancer is leukemia or lymphoma. In certain embodiments, the cancer is multiple myeloma. In specific embodiments, said multiple myeloma is Stage I, Stage II, or Stage III according to the International Staging System or the Revised International Staging System. In certain embodiments, said multiple myeloma is newly-diagnosed multiple myeloma. In other embodiments, said multiple myeloma is relapsed or refractory multiple myeloma.

Further provided herein are kits comprising an effective amount of any of the antibody conjugates provided herein and an effective amount of BMS-986405, and instructions for use of the antibody conjugate and the BMS-986405. In a specific embodiment, the antibody conjugate is lyophilized. In another specific embodiment, the kit further comprises a fluid for reconstitution of the lyophilized antibody. In a specific embodiment, the effective amount of the antibody conjugate is from about 10 mg to about 1000 mg. In a specific embodiment, the effective amount of BMS-986405 is about 25 mg. In a specific embodiment, the kit comprises one or more containers comprising the effective amount of the antibody conjugate and the effective amount of BMS-986405. In a specific embodiment, the effective amount of the antibody conjugate and the effective amount of BMS-986405 are in separate containers. In certain embodiments, provided herein are kits comprising an effective amount of an antibody conjugate provided herein, for example, Conjugate 4, and an effective amount of BMS-986405, in separate containers, and instructions for use of the antibody conjugate and the BMS-986405.

Also provided herein are kits comprising one or more doses of any of the antibody conjugates provided herein and one or more doses of BMS-986405, and instructions for use of the antibody conjugate and the BMS-986405. In a specific embodiment, the antibody conjugate is lyophilized. In another specific embodiment, the kit further comprises a fluid for reconstitution of the lyophilized antibody conjugate. In a specific embodiment, the antibody conjugate is present in an amount that comprises from about 10 mg to about 1000 mg. In a specific embodiment, the BMS-986405 is present in an amount that comprises about 25 mg. In a specific embodiment, the kit comprises one or more containers comprising the antibody conjugate and the BMS-986405. In a specific embodiment, the antibody conjugate and the BMS-986405 are in separate containers.

DETAILED DESCRIPTION OF THE EMBODIMENTS

1. Definitions

Figure 1:
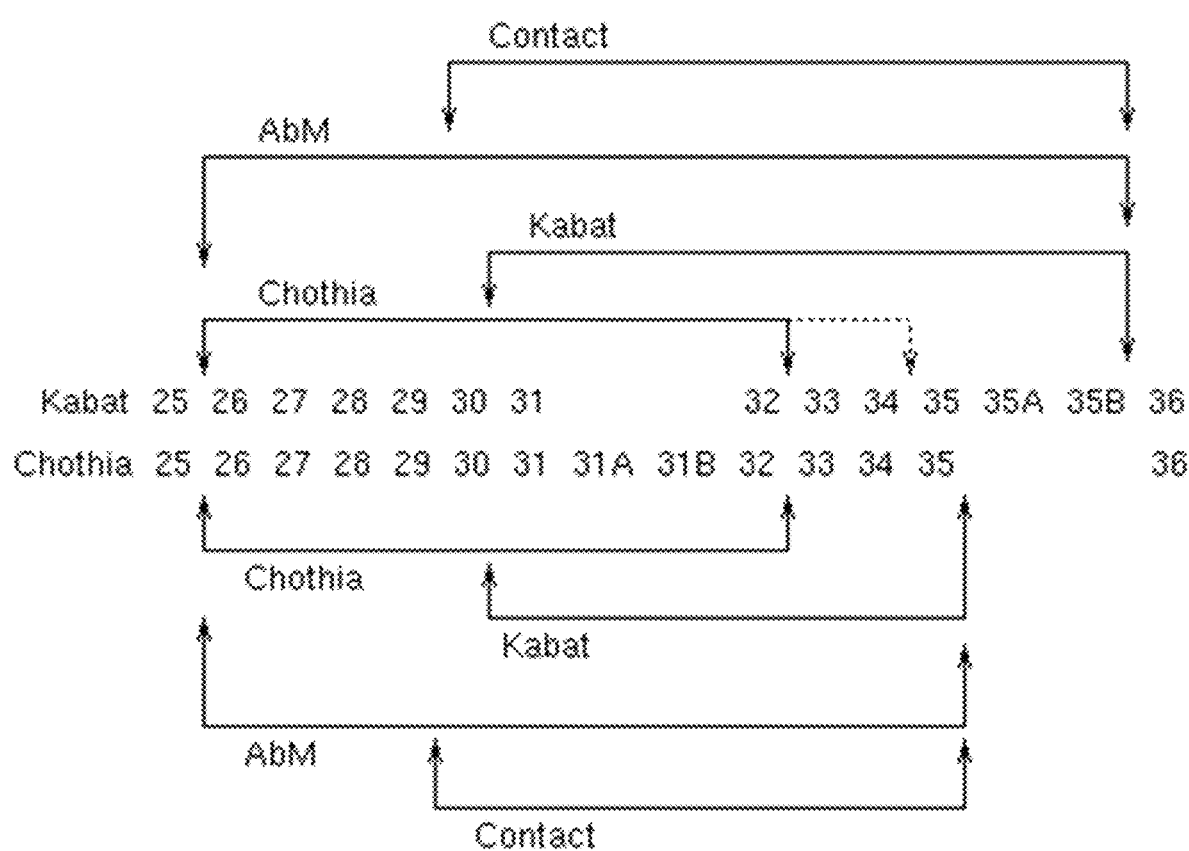
FIG. 1 provides a comparison of the Kabat and Chothia numbering systems for CDR-H1. Adapted from Martin A.C.R. (2010). Protein Sequence and Structure Analysis of Antibody Variable Domains. In R. Kontermann & S. Dübel (Eds.), *Antibody Engineering* vol. 2 (pp. 33-51). Springer-Verlag, Berlin Heidelberg.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Green & Sambrook, *Molecular Cloning: A Laboratory Manual* 4th ed. (2012), Cold Spring Harbor Laboratory Press, Cold Spring Harbor, NY; and Ausubel et al., *Current Protocols in Molecular Biology*, John Wiley & Sons. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value ±10%, ±5%, or ±1%. In certain embodiments, the term "about" indicates the designated value ±one standard deviation of that value.

The term "combinations thereof" includes every possible combination of elements to which the term refers to. For example, a sentence stating that "if $\alpha_2$ is A, then $\alpha_3$ is not D; as is not S; or $\alpha_6$ is not S; or combinations thereof" includes the following combinations when $\alpha_2$ is A: (1) $\alpha_3$ is not D; (2) as is not S; (3) $\alpha_6$ is not S; (4) $\alpha_3$ is not D; as is not S; and $\alpha_6$ is not S; (5) $\alpha_3$ is not D and as is not S; (6) $\alpha_3$ is not D and $\alpha_6$ is not S; and (7) as is not S and $\alpha_6$ is not S.

The terms "BCMA" and "B-cell maturation antigen" are used interchangeably herein. BCMA is also known by synonyms, including BCM, tumor necrosis factor receptor superfamily member 17 ("TNFRSF17"), CD269, TNFRSF13A, and TNF receptor superfamily member 17, among others. Unless specified otherwise, the terms include any variants, isoforms and species homologs of human BCMA that are naturally expressed by cells, or that are expressed by cells transfected with a BCMA or BCMA gene. BCMA proteins include, for example, human BCMA isoform 1 (SEQ ID NO: 1) and human BCMA isoform 2 (SEQ ID NO: 2). In some embodiments, BCMA proteins include cynomolgus monkey BCMA (SEQ ID NO: 3). In some embodiments, BCMA proteins include murine BCMA (SEQ ID NO: 4).

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, PA Briefly, each heavy chain typically comprises a heavy chain variable region ($V_H$ or VH) and a heavy chain constant region ($C_H$ or CH). The heavy chain constant region typically comprises three domains, abbreviated $C_H1$ (or CH1), $C_H2$ (or CH2), and $C_H3$ (or CH3). Each light chain typically comprises a light chain variable region ($V_L$ or $V_L$) and a light chain constant region. The light chain constant region typically comprises one domain, abbreviated CL or CL.

The term "antibody" describes a type of immunoglobulin molecule and is used herein in its broadest sense. An antibody specifically includes intact antibodies (e.g., intact immunoglobulins), and antibody fragments. Antibodies comprise at least one antigen-binding domain. One example of an antigen-binding domain is an antigen binding domain formed by a $V_H$-$V_L$ dimer. A "BCMA antibody," "anti-BCMA antibody," "BCMA Ab," "BCMA-specific antibody," "anti-BCMA Ab," "BCMA antibody," "anti-BCMA antibody," "BCMA Ab," "BCMA-specific antibody," or "anti-BCMA Ab," or any iteration of these phrases where "BCMA" is substituted by "TNFSF17," is an antibody, as described herein, which binds specifically to BCMA. In some embodiments, the antibody binds the extracellular domain of BCMA.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, MD, incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated $\alpha$, $\delta$, $\epsilon$, $\gamma$, and $\mu$, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme), each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

TABLE 1

Residues in CDRs according to Kabat and Chothia numbering schemes.

| CDR | Kabat | Chothia |
| --- | --- | --- |
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR, as illustrated in FIG. 1.

Unless otherwise specified, the numbering scheme used for identification of a particular CDR herein is the Kabat/Chothia numbering scheme. Where the residues encompassed by these two numbering schemes diverge (e.g., CDR-H1 and/or CDR-H2), the numbering scheme is specified as either Kabat or Chothia. For convenience, CDR-H3 is sometimes referred to herein as either Kabat or Chothia. However, this is not intended to imply differences in sequence where they do not exist, and one of skill in the art can readily confirm whether the sequences are the same or different by examining the sequences.

CDRs may be assigned, for example, using antibody numbering software, such as Abnum, available at www.bioinf.org.uk/abs/abnum/, and described in Abhinandan and Martin, *Immunology*, 2008, 45:3832-3839, incorporated by reference in its entirety.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, F(ab')2 fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). In some embodiments, the linker is SEQ ID NO: 26. In some embodiments, the linker is SEQ ID NO: 27. Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminus of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG1 Fc domain. In some embodiments, the IgG1 Fc domain comprises SEQ ID NO: 19, or a portion thereof. SEQ ID NO: 19 provides the sequence of $C_H1$, $C_H2$, and $C_H3$ of the human IgG1 constant region.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

In some embodiments, an isolated antibody is purified to at least 80%, 85%, 90%, 95%, or 99% by weight. In some embodiments, an isolated antibody is purified to at least 80%, 85%, 90%, 95%, or 99% by volume. In some embodiments, an isolated antibody is provided as a solution comprising at least 85%, 90%, 95%, 98%, 99% to 100% by weight. In some embodiments, an isolated antibody is provided as a solution comprising at least 85%, 90%, 95%, 98%, 99% to 100% by volume.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can be represented by the dissociation constant ($K_D$). Affinity can be measured by common methods known in the art, including those described herein. Affinity can be determined, for example, using surface plasmon resonance (SPR) technology, such as a Biacore® instrument. In some embodiments, the affinity is determined at 25° C.

With regard to the binding of an antibody to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that mimics the antibody binding site on the target. In that case, specific binding is indicated if the binding of the antibody to the target is competitively inhibited by the control molecule.

The term "$k_d$" or "kd" (sec$^{-1}$), as used herein, refers to the dissociation rate constant of a particular antibody-antigen interaction. This value is also referred to as the $k_{off}$ value.

The term "$k_a$" or "ka" (M$^{-1}$×sec$^{-1}$), as used herein, refers to the association rate constant of a particular antibody-antigen interaction. This value is also referred to as the kcal value.

The term "$K_D$" (also referred to as "Kd" or "KD," M or nM), as used herein, refers to the dissociation equilibrium constant of a particular antibody-antigen interaction. $K_D = k_d/k_a$. The value of $K_D$ is typically equal in magnitude to the concentration of ligand at which half the protein molecules are bound to ligand at equilibrium.

The term "$K_A$" or "$K_a$" (M$^{-1}$), as used herein, refers to the association equilibrium constant of a particular antibody-antigen interaction. $K_A = k_a/k_d$.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen. Affinity matured antibodies may be produced using a variety of methods known in the art. For example, Marks et al. (*Bio/Technology*, 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.*, 1994, 91:3809-3813); Schier et al., *Gene*, 1995, 169:147-155; Yelton et al., *J. Immunol.*, 1995, 155:1994-2004; Jackson et al., *J. Immunol.*, 1995, 154:3310-33199; and Hawkins et al, *J. Mol. Biol.*, 1992, 226:889-896, each of which is incorporated by reference in its entirety.

When used herein in the context of two or more antibodies, the term "competes with" or "cross-competes with" indicates that the two or more antibodies compete for binding to an antigen (e.g., BCMA). In one exemplary assay, BCMA is coated on a plate and allowed to bind a first antibody, after which a second, labeled antibody is added. If the presence of the first antibody reduces binding of the second antibody, then the antibodies compete. In another exemplary assay, a first antibody is coated on a plate and allowed to bind the antigen, and then the second antibody is added. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 50%, at least 60%, at least 70%, at least 80%, or at least 90%.

The term "epitope" means a portion of an antigen capable of specific binding to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter is lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to variants of BCMA with different point-mutations.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution of an amino acid with a chemically or functionally similar amino acid. Conservative substitution tables providing similar amino acids are well known in the art. Polypeptide sequences having such substitutions are known as "conservatively modified variants." By way of example, the groups of amino acids provided in Tables 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |
| Alcohol Group-Containing Residues | S and T |
| Aliphatic Residues | I, L, V, and M |
| Cycloalkenyl-associated Residues | F, H, W, and Y |
| Hydrophobic Residues | A, C, F, G, H, I, L, M, R, T, V, W, and Y |
| Negatively Charged Residues | D and E |
| Polar Residues | C, D, E, H, K, N, Q, R, S, and T |
| Positively Charged Residues | H, K, and R |
| Small Residues | A, C, D, G, N, P, S, T, and V |
| Very Small Residues | A, G, and S |
| Residues Involved in Turn Formation | A, C, D, E, G, H, K, N, Q, R, S, P, and T |
| Flexible Residues | Q, T, K, S, G, P, D, E, and R |

TABLE 3

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 4

Further selected groups of amino acids that are considered
conservative substitutions for one another, in certain embodiments.

| Group | Amino Acids |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, Proteins: Structures and Molecular Properties 2nd ed. (1993) W. H. Freeman & Co., New York, NY. An antibody generated by making one or more conservative substitutions of amino acid residues in a parent antibody is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Naturally encoded amino acids are the proteinogenic amino acids known to those of skill in the art. They include the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and the less common pyrrolysine and selenocysteine. Naturally encoded amino acids include post-translational variants of the 22 naturally occurring amino acids such as prenylated amino acids, isoprenylated amino acids, myrisoylated amino acids, palmitoylated amino acids, N-linked glycosylated amino acids, O-linked glycosylated amino acids, phosphorylated amino acids and acylated amino acids.

The term "non-natural amino acid" refers to an amino acid that is not a proteinogenic amino acid, or a post-translationally modified variant thereof. In particular, the term refers to an amino acid that is not one of the 20 common amino acids or pyrrolysine or selenocysteine, or post-translationally modified variants thereof.

The term "conjugate" or "antibody conjugate" refers to an antibody linked to one or more payload moieties. The antibody can be any antibody described herein. The payload can be any payload described herein. The antibody can be directly linked to the payload via a covalent bond, or the antibody can be linked to the payload indirectly via a linker. Typically, the linker is covalently bonded to the antibody and also covalently bonded to the payload. The term "antibody drug conjugate" or "ADC" refers to a conjugate wherein at least one payload is a therapeutic moiety such as a drug.

The term "payload" refers to a molecular moiety that can be conjugated to an antibody. In particular embodiments, payloads are selected from the group consisting of therapeutic moieties and labelling moieties.

The term "linker" refers to a molecular moiety that is capable of forming at least two covalent bonds. Typically, a linker is capable of forming at least one covalent bond to an antibody and at least another covalent bond to a payload. In certain embodiments, a linker can form more than one covalent bond to an antibody. In certain embodiments, a linker can form more than one covalent bond to a payload or can form covalent bonds to more than one payload. After a linker forms a bond to an antibody, or a payload, or both, the remaining structure, i.e. the residue of the linker after one or more covalent bonds are formed, may still be referred to as a "linker" herein. The term "linker precursor" refers to a linker having one or more reactive groups capable of forming a covalent bond with an antibody or payload, or both. In some embodiments, the linker is a cleavable linker. For example, a cleavable linker can be one that is released by an bio-labile function, which may or may not be engineered. In some embodiments, the linker is a non-cleavable linker. For example, a non-cleavable linker can be one that is released upon degradation of the antibody.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder.

As used herein, the term "therapeutically effective amount" or "effective amount" refers to an amount of an antibody or composition that when administered to a subject is effective to treat a disease or disorder. In some embodiments, a therapeutically effective amount or effective amount refers to an amount of an antibody or composition that when administered to a subject is effective to prevent or ameliorate a disease or the progression of the disease, or result in amelioration of symptoms.

As used herein, the term "inhibits growth" (e.g. referring to cells, such as tumor cells) is intended to include any measurable decrease in cell growth (e.g., tumor cell growth) when contacted with a BCMA antibody, as compared to the growth of the same cells not in contact with a BCMA antibody. In some embodiments, growth may be inhibited by at least about 10%, 20%, 30%, 40%, 50%, 60%, 70%, 80%, 90%, 99%, or 100%. The decrease in cell growth can occur by a variety of mechanisms, including but not limited to antibody internalization, apoptosis, necrosis, and/or effector function-mediated activity.

As used herein, the term "subject" means a mammalian subject. Exemplary subjects include, but are not limited to humans, monkeys, dogs, cats, mice, rats, cows, horses, camels, avians, goats, and sheep. In certain embodiments, the subject is a human. In some embodiments, the subject has a disease that can be treated or diagnosed with an antibody provided herein. In some embodiments, the disease is leukemia, lymphoma, or multiple myeloma, a plasmacytoid dendritic cell tumor, a B-cell lineage malignancy, a plasma cell neoplasm, diffuse large B-cell lymophoma (DLBCL), a low-grade B-cell lymphoma, Burkitt's lymphoma, a plasmablastic lymphoma, or a follicular lymphoma.

In some chemical structures illustrated herein, certain substituents, chemical groups, and atoms are depicted with a curvy/wavy line (e.g.,

that intersects a bond or bonds to indicate the atom through which the substituents, chemical groups, and atoms are bonded. For example, in some structures, such as but not limited to

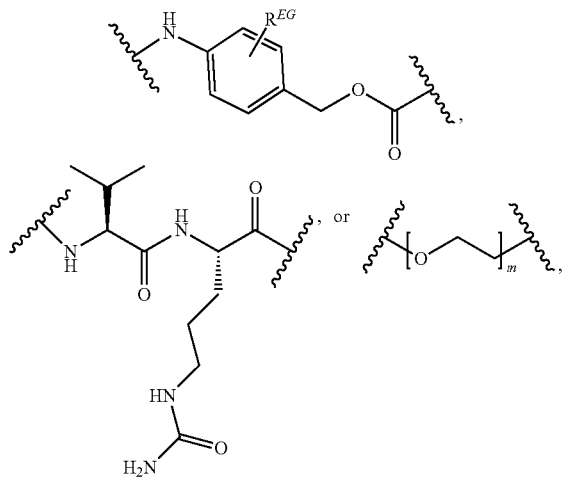

this curvy/wavy line indicates the atoms in the backbone of a conjugate or linker-payload structure to which the illustrated chemical entity is bonded. In some structures, such as but not limited to

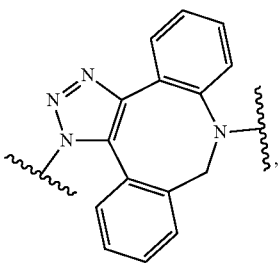 [SMILES: *N1Cc2ccccc2-c2c(nnn2*)-c2ccccc21]

this curvy/wavy line indicates the atoms in the antibody or antibody fragment as well as the atoms in the backbone of a conjugate or linker-payload structure to which the illustrated chemical entity is bonded.

The term "site-specific" refers to a modification of a polypeptide at a predetermined sequence location in the polypeptide. The modification is at a single, predictable residue of the polypeptide with little or no variation. In particular embodiments, a modified amino acid is introduced at that sequence location, for instance recombinantly or synthetically. Similarly, a moiety can be "site-specifically" linked to a residue at a particular sequence location in the polypeptide. In certain embodiments, a polypeptide can comprise more than one site-specific modification.

2. Conjugates

Provided herein are conjugates of antibodies to BCMA that may be used in combination with a gamma secretase inhibitor (e.g., BMS-986405). The conjugates comprise an antibody to BCMA covalently linked via a linker to a payload. In certain embodiments, the antibody is linked to one payload. In further embodiments, the antibody is linked to more than one payload. In certain embodiments, the antibody is linked to two, three, four, five, six, seven, eight, or more payloads.

In the conjugates provided herein, the antibody can be from any species. In certain embodiments, the BCMA is a vertebrate BCMA. In certain embodiments, the BCMA is a mammalian BCMA. In certain embodiments, the BCMA is human BCMA. In certain embodiments, the BCMA is mouse BCMA. In certain embodiments, the BCMA is cynomolgus BCMA.

The antibody is typically a protein comprising multiple polypeptide chains. In certain embodiments, the antibody is a heterotetramer comprising two identical light (L) chains and two identical heavy (H) chains. Each light chain can be linked to a heavy chain by one covalent disulfide bond. Each heavy chain can be linked to the other heavy chain by one or more covalent disulfide bonds. Each heavy chain and each light chain can also have one or more intrachain disulfide bonds. As is known to those of skill in the art, each heavy chain typically comprises a variable domain ($V_H$) followed by a number of constant domains. Each light chain typically comprises a variable domain at one end ($V_L$) and a constant domain. As is known to those of skill in the art, antibodies typically have selective affinity for their target molecules, i.e. antigens.

The antibodies provided herein can have any antibody form known to those of skill in the art. They can be full-length, or fragments. Exemplary full length antibodies include IgA, IgA1, IgA2, IgD, IgE, IgG, IgG1, IgG2, IgG3, IgG4, IgM, etc. Exemplary fragments include Fv, Fab, Fc, scFv, scFv-Fc, etc.

In certain embodiments, the antibody of the conjugate comprises six of the CDR sequences described herein. In certain embodiments, the antibody of the conjugate comprises a heavy chain variable domain ($V_H$) described herein. In certain embodiments, the antibody of the conjugate comprises a light chain variable domain ($V_L$) described herein. In certain embodiments, the antibody of the conjugate comprises a heavy chain variable domain ($V_H$) described herein and a light chain variable domain ($V_L$) described herein. In certain embodiments, the antibody of the conjugate comprises a paired heavy chain variable domain and a light chain variable domain described herein ($V_H$-$V_L$ pair).

In certain embodiments, the antibody conjugate can be formed from an antibody that comprises one or more reactive groups. In certain embodiments, the antibody conjugate can be formed from an antibody comprising all naturally encoded amino acids. Those of skill in the art will recognize that several naturally encoded amino acids include reactive groups capable of conjugation to a payload or to a linker. These reactive groups include cysteine side chains, lysine side chains, and amino-terminal groups. In these embodiments, the antibody conjugate can comprise a payload or linker linked to the residue of an antibody reactive group. In these embodiments, the payload precursor or linker precursor comprises a reactive group capable of forming a bond with an antibody reactive group. Typical reactive groups include maleimide groups, activated carbonates (including but not limited to, p-nitrophenyl ester), activated esters (including but not limited to, N-hydroxysuccinimide, p-nitrophenyl ester, and aldehydes). Particularly useful reactive groups include maleimide and succinimide, for instance N-hydroxysuccinimide, for forming bonds to cysteine and lysine side chains. Further reactive groups are described in the sections and examples below.

In further embodiments, the antibody comprises one or more modified amino acids having a reactive group, as described herein. Typically, the modified amino acid is not a naturally encoded amino acid. These modified amino acids can comprise a reactive group useful for forming a covalent bond to a linker precursor or to a payload precursor. One of skill in the art can use the reactive group to link the polypeptide to any molecular entity capable of forming a covalent bond to the modified amino acid. Thus, provided herein are conjugates comprising an antibody comprising a modified amino acid residue linked to a payload directly or indirectly via a linker. Exemplary modified amino acids are described in the sections below. Generally, the modified amino acids have reactive groups capable of forming bonds to linkers or payloads with complementary reactive groups.

In certain embodiments, the non-natural amino acids are positioned at select locations in a polypeptide chain of the antibody. These locations were identified as providing optimum sites for substitution with the non-natural amino acids. Each site is capable of bearing a non-natural amino acid with optimum structure, function and/or methods for producing the antibody.

In certain embodiments, a site-specific position for substitution provides an antibody that is stable. Stability can be measured by any technique apparent to those of skill in the art.

In certain embodiments, a site-specific position for substitution provides an antibody that has optimal functional properties. For instance, the antibody can show little or no loss of binding affinity for its target antigen compared to an antibody without the site-specific non-natural amino acid. In certain embodiments, the antibody can show enhanced binding compared to an antibody without the site-specific non-natural amino acid.

In certain embodiments, a site-specific position for substitution provides an antibody that can be made advantageously. For instance, in certain embodiments, the antibody shows advantageous properties in its methods of synthesis, discussed below. In certain embodiments, the antibody can show little or no loss in yield in production compared to an antibody without the site-specific non-natural amino acid. In certain embodiments, the antibody can show enhanced yield in production compared to an antibody without the site-specific non-natural amino acid. In certain embodiments, the antibody can show little or no loss of tRNA suppression compared to an antibody without the site-specific non-natural amino acid. In certain embodiments, the antibody can show enhanced tRNA suppression in production compared to an antibody without the site-specific non-natural amino acid.

In certain embodiments, a site-specific position for substitution provides an antibody that has advantageous solubility. In certain embodiments, the antibody can show little or no loss in solubility compared to an antibody without the site-specific non-natural amino acid. In certain embodiments, the antibody can show enhanced solubility compared to an antibody without the site-specific non-natural amino acid.

In certain embodiments, a site-specific position for substitution provides an antibody that has advantageous expression. In certain embodiments, the antibody can show little or no loss in expression compared to an antibody without the site-specific non-natural amino acid. In certain embodiments, the antibody can show enhanced expression compared to an antibody without the site-specific non-natural amino acid.

In certain embodiments, a site-specific position for substitution provides an antibody that has advantageous folding. In certain embodiments, the antibody can show little or no loss in proper folding compared to an antibody without the site-specific non-natural amino acid. In certain embodiments, the antibody can show enhanced folding compared to an antibody without the site-specific non-natural amino acid.

In certain embodiments, a site-specific position for substitution provides an antibody that is capable of advantageous conjugation. As described below, several non-natural amino acids have side chains or functional groups that facilitate conjugation of the antibody to a second agent, either directly or via a linker. In certain embodiments, the antibody can show enhanced conjugation efficiency compared to an antibody without the same or other non-natural amino acids at other positions. In certain embodiments, the antibody can show enhanced conjugation yield compared to an antibody without the same or other non-natural amino acids at other positions. In certain embodiments, the antibody can show enhanced conjugation specificity compared to an antibody without the same or other non-natural amino acids at other positions.

The one or more non-natural amino acids are located at selected site-specific positions in at least one polypeptide chain of the antibody. The polypeptide chain can be any polypeptide chain of the antibody without limitation, including either light chain or either heavy chain. The site-specific position can be in any domain of the antibody, including any variable domain and any constant domain.

In certain embodiments, the antibodies provided herein comprise one non-natural amino acid at a site-specific position. In certain embodiments, the antibodies provided herein comprise two non-natural amino acids at site-specific positions. In certain embodiments, the antibodies provided herein comprise three non-natural amino acids at site-specific positions. In certain embodiments, the antibodies provided herein comprise more than three non-natural amino acids at site-specific positions.

In certain embodiments, the antibodies provided herein comprise non-natural amino acids each at the positions HC-F404 and HC-Y180, according to the Kabat or Chothia or EU numbering scheme, or a post-translationally modified variant thereof. In these designations, HC indicates a heavy chain residue, and LC indicates a light chain residue. Those of skill will recognize that the non-natural amino acids substitute for the residues HC-F404 and HC-Y180 in the antibody amino acid sequence. In certain embodiments, the non-natural amino acids are residues of Formula (30), herein.

3. Conjugating Groups and Residues Thereof

Conjugating groups facilitate conjugation of the payloads described herein to a second compound, such as an antibody described herein. In certain embodiments, the conjugating group is designated R herein. Conjugating groups can react via any suitable reaction mechanism known to those of skill in the art. In certain embodiments, a conjugating group reacts through a [3+2] alkyne-azide cycloaddition reaction, inverse-electron demand Diels-Alder ligation reaction, thiol-electrophile reaction, or carbonyl-oxyamine reaction, as described in detail herein. In certain embodiments, the conjugating group comprises an alkyne, for instance a strained alkyne. In certain embodiments, the conjugating group is:

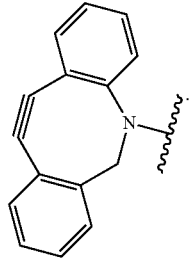 [SMILES: *N1Cc2ccccc2C#Cc2ccccc21]

Additional conjugating groups are described in, for example, U.S. Patent Publication No. 2014/0356385, U.S. Patent Publication No. 2013/0189287, U.S. Patent Publication No. 2013/0251783, U.S. Pat. Nos. 8,703,936, 9,145,361, 9,222,940, and 8,431,558.

After conjugation, a divalent residue of the conjugating group is formed and is bonded to the residue of a second compound. The structure of the divalent residue is determined by the type of conjugation reaction employed to form the conjugate.

In certain embodiments when a conjugate is formed through a [3+2] alkyne-azide cycloaddition reaction, the divalent residue of the conjugating group comprises a triazole ring or fused cyclic group comprising a triazole ring. In certain embodiments when a conjugate is formed through a strain-promoted [3+2] alkyne-azide cycloaddition (SPAAC) reaction, the divalent residue of the conjugating group is:

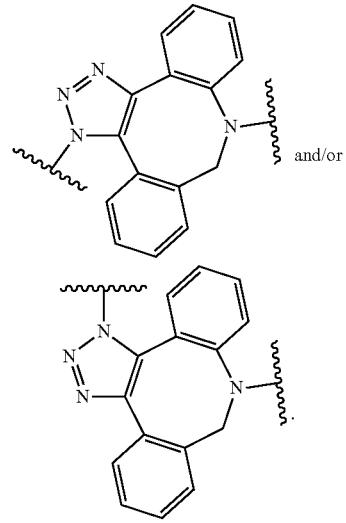

In an embodiment, provided herein is a conjugate according to any of Formulas 101a-105b, where COMP indicates a residue of the anti-BCMA antibody and PAY indicates the payload moiety:

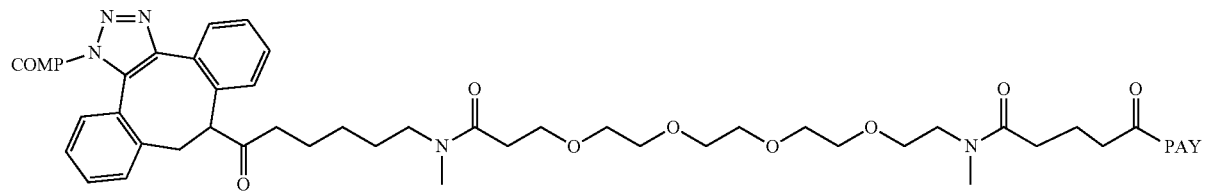

(105a)

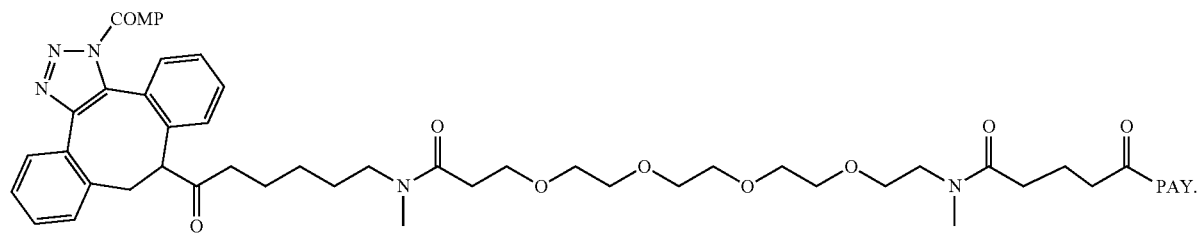

(105b)

In any of the foregoing embodiments, the conjugate comprises n number of PAY moieties, wherein n is an integer from 1 to 8. In some embodiments, n is 2. In some embodiments, n is 3. In some embodiments, n is 4. In some embodiments, n is 5. In some embodiments, n is 6. In some embodiments, n is 7. In some embodiments, n is 8.

In particular embodiments, provided herein are anti-BCMA conjugates according to any of Formulas 105a-105b wherein COMP indicates a residue of the non-natural amino acid according to Formula (30), below. In particular embodiments, provided herein are anti-BCMA conjugates according to any of Formulas 105a-105b wherein COMP indicates a residue of the non-natural amino acid according to Formula (30), below, at heavy chain position 404 according to the EU numbering system. In particular embodiments, provided herein are anti-BCMA conjugates according to any of Formulas 105a-105b wherein COMP indicates a residue of the non-natural amino acid according to Formula (30), below, at heavy chain position 180 according to the EU numbering system.

bodies as residues. For instance, a residue of Formula (30) can be according to the following Formula:

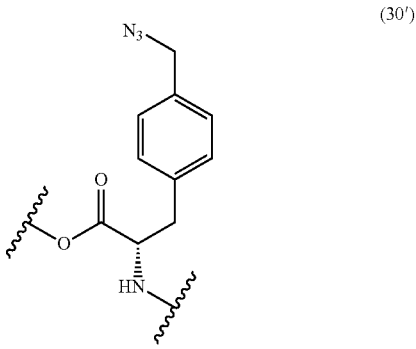

(30')

Further modification, for instance at —N₃ is also encompassed within the term residue herein.

In an embodiment, provided herein is a conjugate according to any of Formulas 105c-105d, where COMP indicates a residue of the anti-BCMA antibody and PAY indicates the payload moiety:

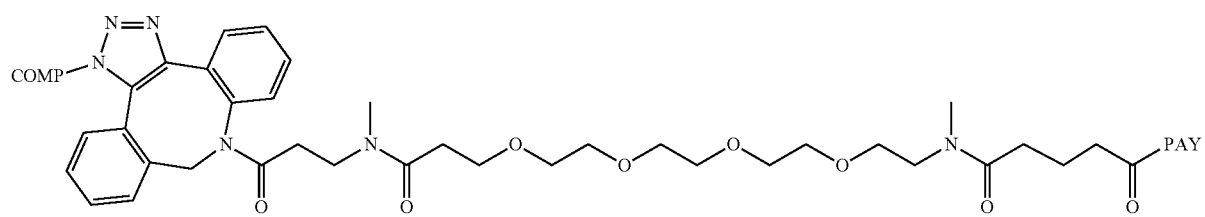

(105c)

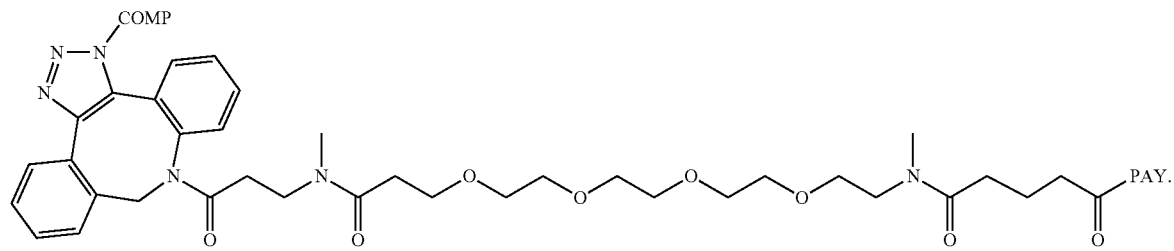

(105d)

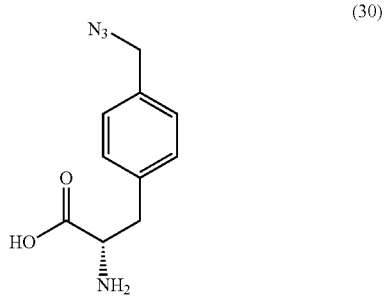 [SMILES: [N-]=[N+]=NCc1ccc(C[C@H](N)C(=O)O)cc1]

(30)

Those of skill will recognize that amino acids such as Formula (30) are incorporated into polypeptides and anti- In any of the foregoing embodiments, the conjugate comprises n number of PAY moieties, wherein n is an integer from 1 to 8. In some embodiments, n is 2. In some embodiments, n is 3. In some embodiments, n is 4. In some embodiments, n is 5. In some embodiments, n is 6. In some embodiments, n is 7. In some embodiments, n is 8.

In particular embodiments, provided herein are anti-BCMA conjugates according to any of Formulas 105c-105d wherein COMP indicates a residue of the non-natural amino acid according to Formula (30), below. In particular embodiments, provided herein are anti-BCMA conjugates according to any of Formulas 105c-105d wherein COMP indicates a residue of the non-natural amino acid according to Formula (30), below, at heavy chain position 404 according to the EU numbering system. In particular embodiments, provided herein are anti-BCMA conjugates according to any of Formulas 105c-105d wherein COMP indicates a residue of the non-natural amino acid according to Formula (30), below, at heavy chain position 180 according to the EU numbering system.

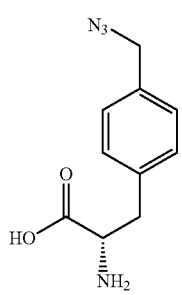

(30)

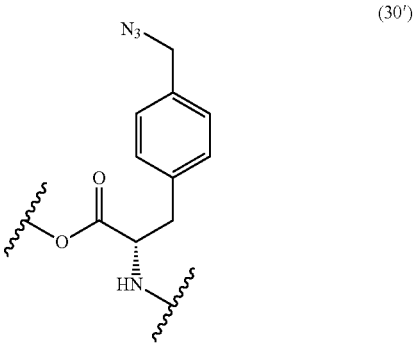 [SMILES: *N[C@@H](Cc1ccc(CN=[N+]=[N-])cc1)C(=O)O*]

(30′)

Those of skill will recognize that amino acids such as Formula (30) are incorporated into polypeptides and antibodies as residues. For instance, a residue of Formula (30) can be according to the following Formula:

Further modification, for instance at —N$_3$ is also encompassed within the term residue herein.

In particular embodiments, provided herein are anti-BCMA conjugates having the structure of Conjugate M:

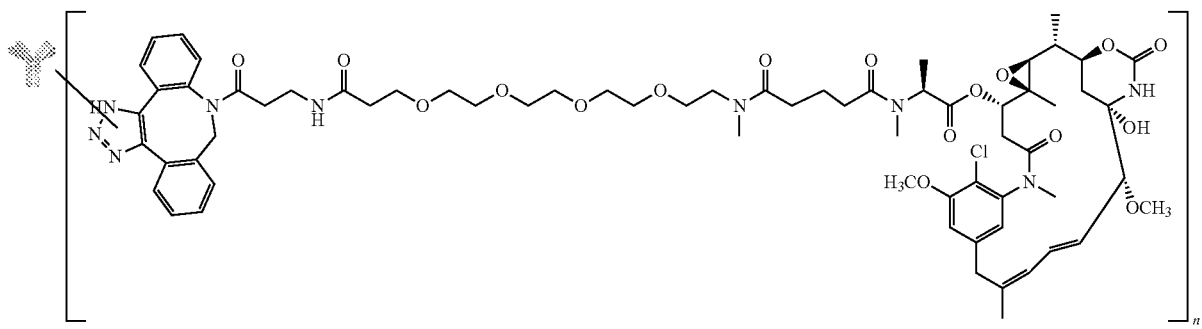

where n is an integer from 1 to 6. In some embodiments, n is an integer from 1 to 4. In some embodiments, n is 2. For example, in particular embodiments, the anti-BCMA conjugate has the structure:

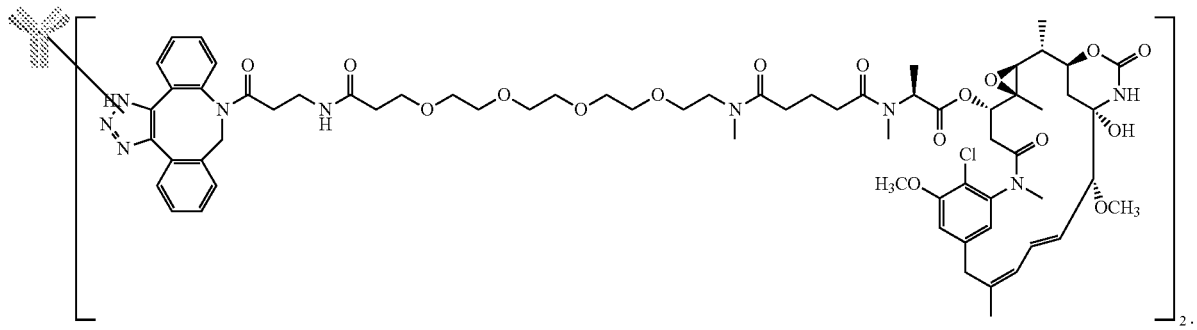

In some embodiments, n is 4. For example, in particular embodiments, the anti-BCMA conjugate has the structure:

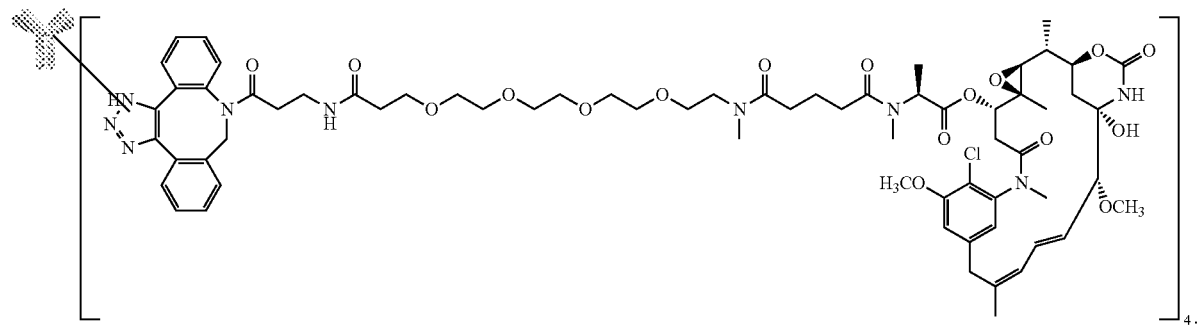

In any of the foregoing embodiments wherein the anti-BCMA conjugate has a structure according to Conjugate M, the bracketed structure can be covalently bonded to one or more non-natural amino acids of the antibody at sites HC-F404 and HC-Y180, according to the Kabat or EU numbering scheme of Kabat. In particular embodiments, each non-natural amino acid is a residue according to Formula (30).

In one embodiment, the anti-BCMA conjugate is Conjugate 4, having the structure of:

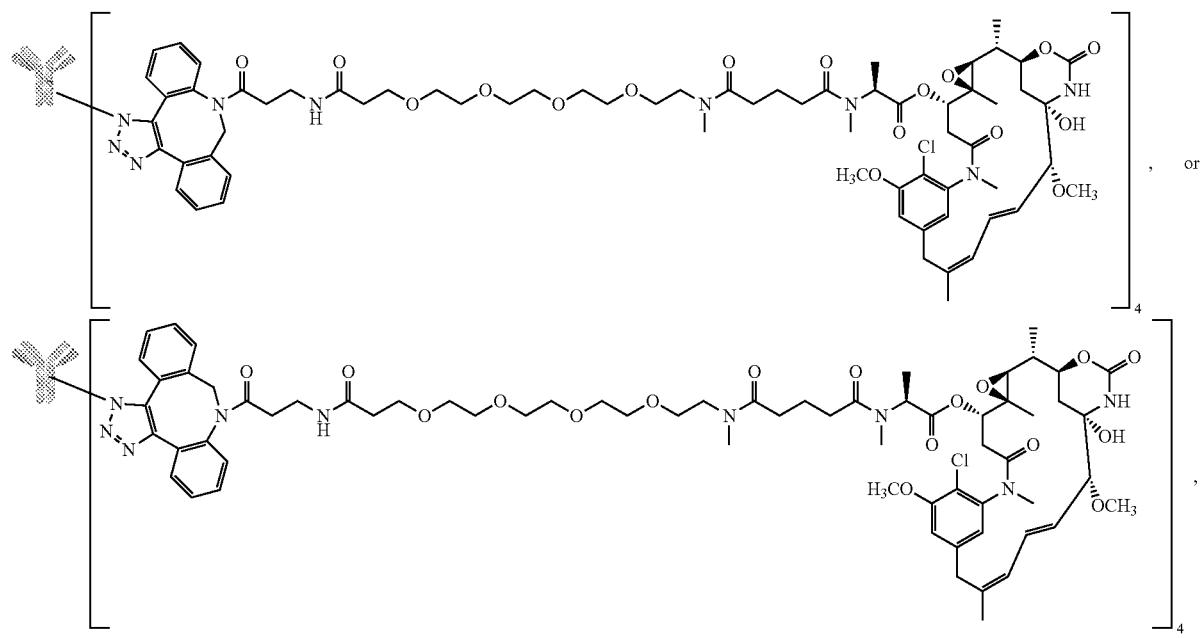

wherein the antibody comprises a heavy chain sequence provided in SEQ ID NO: 15, and a light chain sequence provided in SEQ ID NO: 17;

wherein the antibody further comprises residues of p-azidomethyl-phenylalanine substituting at each of sites HC-F404 and HC-Y180 according to the EU numbering scheme; and each structure within the brackets of the formulas is bonded to the antibody at one of the p-azidomethyl-phenylalanine residues.

In one embodiment, the anti-BCMA conjugate is Conjugate 4, wherein the predominant species is:

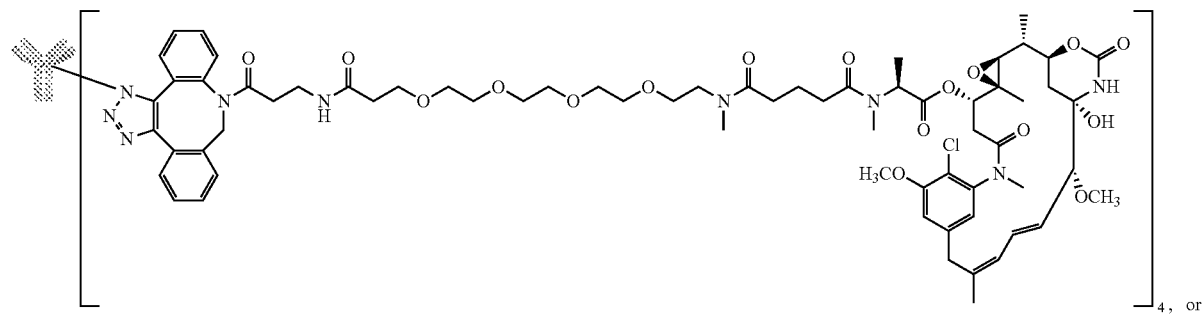

wherein the antibody comprises a heavy chain sequence provided in SEQ ID NO: 15, and a light chain sequence provided in SEQ ID NO: 17;
wherein the antibody further comprises residues of p-azidomethyl-phenylalanine substituting at each of sites HC-F404 and HC-Y180 according to the EU numbering scheme; and
each structure within the brackets of the formulas is bonded to the antibody at one of the p-azidomethyl-phenylalanine residues.

In one embodiment, the anti-BCMA conjugate is Conjugate 4, wherein the predominant species is:

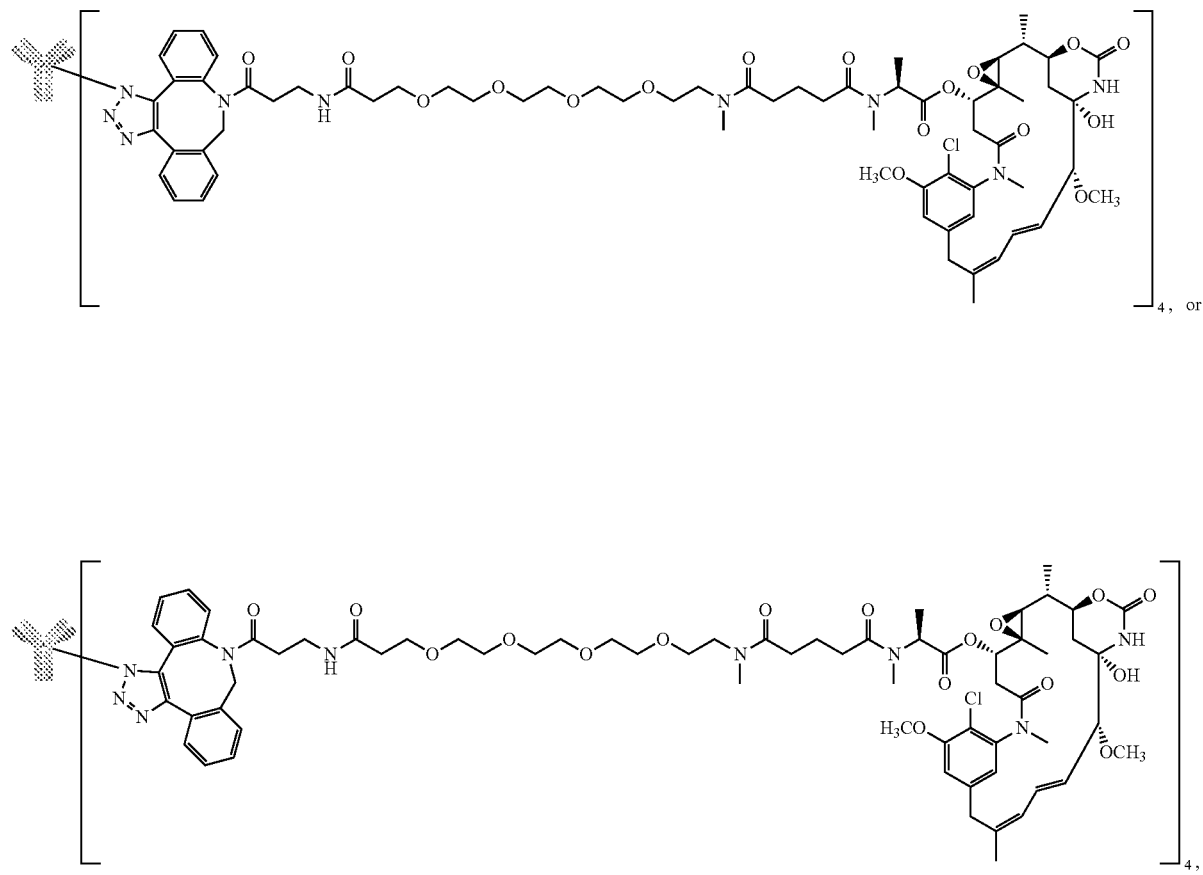

wherein the antibody comprises a heavy chain sequence provided in SEQ ID NO: 15, and a light chain sequence provided in SEQ ID NO: 17;
wherein the antibody further comprises residues of p-azidomethyl-phenylalanine substituting at each of sites HC-F404 and HC-Y180 according to the EU numbering scheme; and
each structure within the brackets of the formulas is bonded to the antibody at one of the p-azidomethyl-phenylalanine residues.

In one embodiment, the anti-BCMA conjugate is Conjugate 4, wherein the predominant species is:

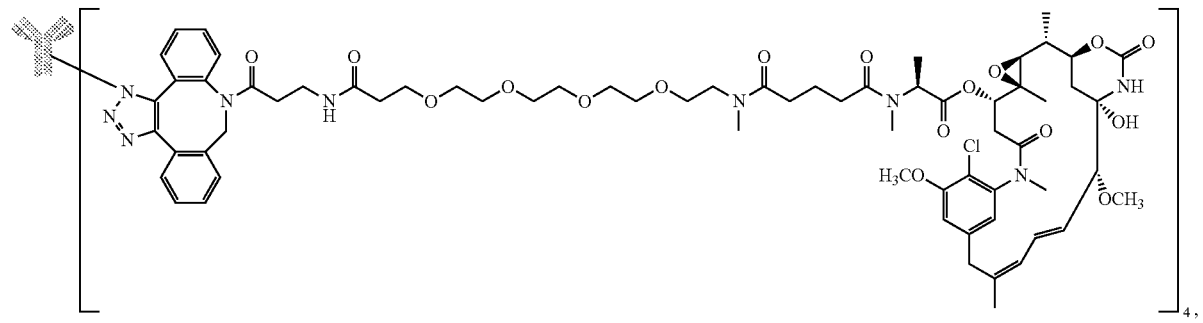

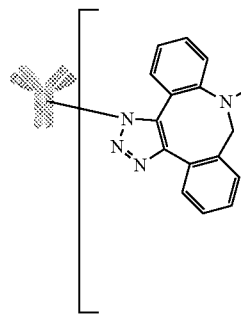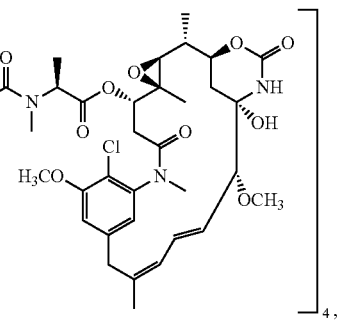

wherein the antibody comprises a heavy chain sequence provided in SEQ ID NO: 15, and a light chain sequence provided in SEQ ID NO: 17;
wherein the antibody further comprises residues of p-azidomethyl-phenylalanine substituting at each of sites HC-F404 and HC-Y180 according to the EU numbering scheme; and
each structure within the brackets of the formulas is bonded to the antibody at one of the p-azidomethyl-phenylalanine residues.

4. Antibody Specificity

The conjugates comprise antibodies that selectively bind human BCMA. In some aspects, the antibody selectively binds to the extracellular domain of human BCMA (human BCMA).

In some embodiments, the antibody binds to a homolog of human BCMA. In some aspects, the antibody binds to a homolog of human BCMA from a species selected from monkeys, mice, dogs, cats, rats, cows, horses, goats and sheep. In some aspects, the homolog is a cynomolgus monkey homolog. In some aspects, the homolog is a mouse or murine homolog.

In some embodiments, the antibody comprises a light chain. In some aspects, the light chain is a kappa light chain. In some aspects, the light chain is a lambda light chain. In specific embodiments, the kappa light chain comprises a constant region comprising the amino acid sequence provided SEQ ID NO: 20.

In some embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a F(ab')$_2$ fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

In some embodiments, the antibody is an affinity matured antibody. In some aspects, the antibody is an affinity matured antibody derived from an illustrative sequence provided in this disclosure.

The antibody conjugates provided herein may be useful for the treatment of a variety of diseases and conditions including cancers. In some embodiments, the antibody conjugates provided herein may be useful for the treatment of cancers of solid tumors. For example, the antibody conjugates provided herein can be useful for the treatment of colorectal cancer.

In some embodiments, the antibody comprises, consists of, or consists essentially of a $V_H$ sequence provided in SEQ ID NO: 13. In some embodiments, the antibody comprises, consists of, or consists essentially of a $V_L$ sequence provided in SEQ ID NO: 14. In some embodiments, the antibody comprises a $V_H$ sequence and a $V_L$ sequence. In some aspects, the $V_H$ sequence is a $V_H$ sequence comprising, consisting of, or consisting essentially of any one of SEQ ID NO: 13, and the $V_L$ sequence is a $V_L$ sequence comprising, consisting of, or consisting essentially of any one of SEQ ID NO: 14. In certain embodiments, the antibody comprises, consists of, or consists essentially of, a heavy chain sequence provided in SEQ ID NO: 15. In a specific embodiments, the heavy chain sequence, e.g., heavy chain sequence provided in SEQ ID NO: 15, additionally comprises an N-terminal methionine. An certain embodiments, such heavy chain sequence is encoded by the nucleotide sequence provided in SEQ ID NO: 16. In certain embodiments, the antibody comprises, consists of, or consists essentially of, a light chain sequence provided in SEQ ID NO: 17. In a specific embodiments, the light chain sequence, e.g., light chain sequence provided in SEQ ID NO: 17, additionally comprises an N-terminal methionine. An certain embodiments, such light chain sequence is encoded by the nucleotide sequence provided in SEQ ID NO: 18.

In some embodiments, the antibodies comprise six of the CDRs indicated in Table 5 below. In particular embodiments, Chothia CDRs are selected. In particular embodiments, Kabat CDRs are selected.

TABLE 5

Antibody 2265-F02 CDRs.

| | Chothia CDR H1 SEQ ID NO | Kabat CDR H1 SEQ ID NO | Chothia CDR H2 SEQ ID NO | Kabat CDR H2 SEQ ID NO | CDR H3 SEQ ID NO | CDR L1 SEQ ID NO | CDR L2 SEQ ID NO | CDR L3 SEQ ID NO |
|---|---|---|---|---|---|---|---|---|
| 2265-F02 | 5 | 6 | 7 | 8 | 9 | 10 | 11 | 12 |

In some embodiments, the antibody comprises three of: a CDR-H1 comprising one of SEQ ID NOs: 5 and 6; a CDR-H2 comprising one of SEQ ID NOs: 7 and 8; a CDR-H3 comprising SEQ ID NO: 9; and one, two, or all three of: a CDR-L1 comprising SEQ ID NO: 10; a CDR-L2 comprising SEQ ID NO: 11; and a CDR-L3 comprising SEQ ID NO: 12. In particular embodiments, the CDRs are according to Chothia. In particular embodiments, the CDRs are according to Kabat.

5. Germline

In some embodiments, the antibody that specifically binds BCMA is an antibody comprising a variable region that is encoded by a particular germline gene, or a variant thereof. The illustrative antibodies provided herein comprise variable regions that are encoded by the heavy chain variable region germline genes VH1-18, VH3-33, VH2-5, VH2-70, and VH4-30-4. or variants thereof; and the light chain variable region germline genes Vκ1-5, Vκ3-11, Vκ2-20, Vκ1-33, and Vκ1-16, or variants thereof.

One of skill in the art would recognize that the CDR sequences provided herein may also be useful when combined with variable regions encoded by other variable region germline genes, or variants thereof. In particular, the CDR sequences provided herein may be useful when combined with variable regions encoded by variable region germline genes, or variants thereof, that are structurally similar to the variable region germline genes recited above. For example, in some embodiments, a CDR-H sequence provided herein may be combined with a variable region encoded by a variable region germline gene selected from the $V_H 1$, $V_H 2$, $V_H 3$, or $V_H 4$ families, or a variant thereof. In some embodiments, a CDR-L sequence provided herein may be combined with a variable region encoded by a variable region germline gene selected from the Vκ1, Vκ2, or Vκ3, or a variant thereof.

6. Glycosylation Variants

In certain embodiments, an antibody may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

7. Fc Variants

In certain embodiments, amino acid modifications may be introduced into the Fc region of an antibody provided herein to generate an Fc region variant. In certain embodiments, the Fc region variant possesses some, but not all, effector functions. Such antibodies may be useful, for example, in applications in which the half-life of the antibody in vivo is important, yet certain effector functions are unnecessary or deleterious. Examples of effector functions include complement-dependent cytotoxicity (CDC) and antibody-directed complement-mediated cytotoxicity (ADCC). Numerous substitutions or substitutions or deletions with altered effector function are known in the art.

In some embodiments, the Fc comprises one or more modifications in at least one of the CH3 sequences. In some embodiments, the Fc comprises one or more modifications in at least one of the CH2 sequences. For example, the Fc can include one or modifications selected from the group consisting of: V262E, V262D, V262K, V262R, V262S, V264S, V303R, and V305R. In some embodiments, an Fc is a single polypeptide. In some embodiments, an Fc is multiple peptides, e.g., two polypeptides. Exemplary modifications in the Fc region are described, for example, in International Patent Application No. PCT/US2017/037545, filed Jun. 14, 2017.

An alteration in in CDC and/or ADCC activity can be confirmed using in vitro and/or in vivo assays. For example, Fc receptor (FcR) binding assays can be conducted to measure FcγR binding. The primary cells for mediating ADCC, NK cells, express FcγRIII only, whereas monocytes express FcγRI, FcγRII and FcγRIII. FcR expression on hematopoietic cells is summarized in Ravetch and Kinet, *Ann. Rev. Immunol.,* 1991, 9:457-492, incorporated by reference in its entirety.

Non-limiting examples of in vitro assays to assess ADCC activity of a molecule of interest are provided in U.S. Pat. Nos. 5,500,362 and 5,821,337; Hellstrom et al., *Proc. Natl. Acad. Sci. U.S.A.,* 1986, 83:7059-7063; Hellstrom et al., *Proc. Natl. Acad. Sci. U.S.A.,* 1985, 82:1499-1502; and Bruggemann et al., *J. Exp. Med.,* 1987, 166:1351-1361; each of which is incorporated by reference in its entirety. Useful effector cells for such assays include peripheral blood mononuclear cells (PBMC) and Natural Killer (NK) cells. Alternatively, or additionally, ADCC activity of the molecule of interest may be assessed in vivo, using an animal model such as that disclosed in Clynes et al. *Proc. Natl. Acad. Sci. U.S.A.*, 1998, 95:652-656, incorporated by reference in its entirety.

C1q binding assays may also be carried out to confirm that the antibody is unable to bind C1q and hence lacks CDC activity. Examples of C1q binding assays include those described in WO 2006/029879 and WO 2005/100402, each of which is incorporated by reference in its entirety.

Complement activation assays include those described, for example, in Gazzano-Santoro et al., *J. Immunol. Methods*, 1996, 202:163-171; Cragg et al., *Blood*, 2003, 101: 1045-1052; and Cragg and Glennie, Blood, 2004, 103:2738-2743; each of which is incorporated by reference in its entirety.

FcRn binding and in vivo clearance (half-life determination) can also be measured, for example, using the methods described in Petkova et al., *Intl. Immunol.*, 2006, 18:1759-1769, incorporated by reference in its entirety.

8. Modified Amino Acids

When the antibody conjugate comprises a modified amino acid, the modified amino acid can be any modified amino acid deemed suitable by the practitioner. In particular embodiments, the modified amino acid is p-azido-methyl-L-phenylalanine (also referred to as p-methylazido phenylalanine). In particular embodiments, the non-natural amino acid is compound (30):

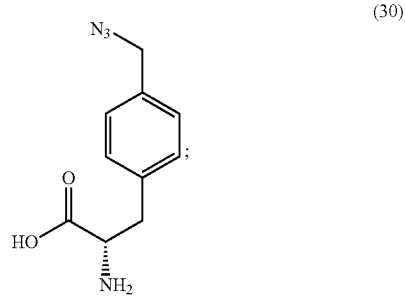 [SMILES: [N-]=[N+]=NCc1ccc(C[C@H](N)C(=O)O)cc1]

(30)

or a salt thereof. Such non-natural amino acids may be in the form of a salt. It will be understood by one of ordinary skill in the art that the azido moiety of the p-azido-methyl-L-phenylalanine residue reacts with a conjugating group to form the triazole of the fused cyclic group formed through the strain-promoted [3+2] alkyne-azide cycloaddition reaction used to make certain of the conjugates described herein.

9. Preparation of Antibody Conjugates 9.1. Antigen Preparation

The BCMA protein to be used for isolation of the antibodies may be intact BCMA or a fragment of BCMA. The intact BCMA protein, or fragment of BCMA, may be in the form of an isolated protein or protein expressed by a cell. Other forms of BCMA useful for generating antibodies will be apparent to those skilled in the art.

9.2. Monoclonal Antibodies

Monoclonal antibodies may be obtained, for example, using the hybridoma method first described by Kohler et al., *Nature*, 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage or yeast-based libraries. See e.g., U.S. Pat. Nos. 8,258,082 and 8,691,730, each of which is incorporated by reference in its entirety.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* $3^{rd}$ ed. (1986) Academic Press, San Diego, CA, incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, CA), and SP-2 or X63-Ag8-653 cells (available from the American Type Culture Collection, Rockville, MD). Human myeloma and mouse-human heteromyeloma cell lines also have been described for the production of human monoclonal antibodies. See e.g., Kozbor, *J. Immunol.*, 1984, 133:3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

9.3. Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature*, 1991, 349:293-299; Rader et al., *Proc. Nat. Acad. Sci. U.S.A.,* 1998, 95:8910-8915; Steinberger et al., *J. Biol. Chem.,* 2000, 275:36073-36078; Queen et al., *Proc. Natl. Acad. Sci. U.S.A.,* 1989, 86:10029-10033; and U.S. Pat. Nos. 5,585,089, 5,693,761, 5,693,762, and 6,180,370; each of which is incorporated by reference in its entirety.

9.4. Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.,* 1993, 90:2551; Jakobovits et al., *Nature,* 1993, 362:255-258; Bruggermann et al., *Year in Immuno.,* 1993, 7:33; and U.S. Pat. Nos. 5,591,669, 5,589,369 and 5,545,807; each of which is incorporated by reference in its entirety. Human antibodies can also be derived from phage-display libraries (see e.g., Hoogenboom et al., *J. Mol. Biol.,* 1991, 227:381-388; Marks et al., *J. Mol. Biol.,* 1991, 222:581-597; and U.S. Pat. Nos. 5,565,332 and 5,573,905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. No. 8,691,730, incorporated by reference in its entirety).

9.5. Conjugation

The antibody conjugates can be prepared by standard techniques. In certain embodiments, an antibody is contacted with a payload precursor under conditions suitable for forming a bond from the antibody to the payload to form an antibody-payload conjugate. In certain embodiments, an antibody is contacted with a linker precursor under conditions suitable for forming a bond from the antibody to the linker. The resulting antibody-linker is contacted with a payload precursor under conditions suitable for forming a bond from the antibody-linker to the payload to form an antibody-linker-payload conjugate. In certain embodiments, a payload precursor is contacted with a linker precursor under conditions suitable for forming a bond from the payload to the linker. The resulting payload-linker is contacted with an antibody under conditions suitable for forming a bond from the payload-linker to the antibody to form an antibody-linker-payload conjugate. Suitable linkers for preparing the antibody conjugates are disclosed herein, and exemplary conditions for conjugation are described in the Examples below.

In some embodiments, an anti-BCMA conjugate is prepared by contacting an anti-BCMA antibody as disclosed herein with a linker precursor having a structure (M):

Such a linker precursor can be prepared by standard techniques, or obtained from commercial sources, e.g. WO 2019/055931, WO 2019/055909, WO 2017/132617, WO 2017/132615, each incorporated by reference in its entirety.

It will be understood that the conjugates from the conjugation reaction disclosed herein may result in a mixture of conjugates with a distribution of one or more drugs (e.g., PAY moieties) attached to an antibody. Individual conjugates may be identified in the mixture by, for example, mass spectroscopy and separated by HPLC, e.g., hydrophobic interaction chromatography, including such methods known in the art. In certain embodiments, the mixture of conjugates comprises a predominant conjugate species. In certain embodiments, a homogeneous conjugate with a single drug to antibody ratio (DAR) value may be isolated from the conjugation mixture, for example by electrophoresis or chromatography.

DAR may range from 1 to 8 units per conjugate. The quantitative distribution of DAR in terms of n may also be determined. In some instances, separation, purification, and characterization of homogeneous conjugate where n is a certain value may be achieved by means such as electrophoresis.

In certain embodiments, the DAR for a conjugate provided herein ranges from 1 to 8. In certain embodiments, the DAR for a conjugate provided herein ranges from about 2 to about 6; from about 3 to about 5.

In some embodiments, the DAR for a conjugate provided herein is about 1. In some embodiments, the DAR for a conjugate provided herein is about 2. In some embodiments, the DAR for a conjugate provided herein is about 2.5. In some embodiments, the DAR for a conjugate provided herein is about 3. In some embodiments, the DAR for a conjugate provided herein is about 3.5. In some embodiments, the DAR for a conjugate provided herein is about 4. In some embodiments, the DAR for a conjugate provided herein is about 3.0, about 3.1, about 3.2, about 3.3, about 3.4, about 3.5, about 3.6, about 3.7, about 3.8, or about 3.9. In some embodiments, the DAR for a conjugate provided herein is about 5. In some embodiments, the DAR for a conjugate provided herein is about 6. In some embodiments, the DAR for a conjugate provided herein is about 7. In some embodiments, the DAR for a conjugate provided herein is about 8.

In some preferred embodiments, the DAR for a conjugate provided herein is about 4.

(M)

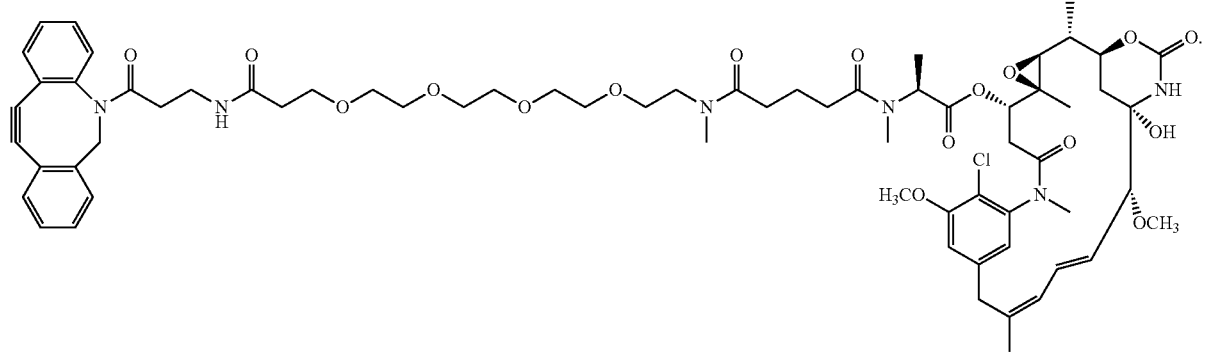

10. Vectors, Host Cells, and Recombinant Methods

Embodiments are also directed to the provision of isolated nucleic acids encoding anti-BCMA antibodies, vectors and host cells comprising the nucleic acids, and recombinant techniques for the production of the antibodies.

For recombinant production of the antibody, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells are provided below. These host cells are not meant to be limiting.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter*, *Erwinia*, *Klebsiella*, *Proteus*, *Salmonella* (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are suitable.

In addition to prokaryotes, eukaryotic microbes such as filamentous fungi or yeast are also suitable cloning or expression hosts for anti-BCMA antibody-encoding vectors. *Saccharomyces cerevisiae*, or common baker's yeast, is a commonly used lower eukaryotic host microorganism. However, a number of other genera, species, and strains are available and useful, such as *Spodoptera frugiperda* (e.g., SF9), *Schizosaccharomyces pombe*, *Kluyveromyces* (*K. lactis*, *K. fragilis*, *K. bulgaricus K. wickeramii*, *K. waltii*, *K. drosophilarum*, *K. thermotolerans*, and *K. marxianus*), *Yarrowia*, *Pichia pastoris*, *Candida* (*C. albicans*), *Trichoderma reesia*, *Neurospora crassa*, *Schwanniomyces* (*S. occidentalis*), and filamentous fungi such as, for example *Penicillium*, *Tolypocladium*, and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the anti-BCMA antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.*, 1979, 58:44; Barnes et al., *Anal. Biochem.*, 1980, 102:255; and U.S. Pat. Nos. 4,767,704, 4,657,866, 4,927,762, 4,560,655, and 5,122,469, or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio/Technology*, 1992, 10:163-167) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., *mAbs*, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low. The antibodies produced in a cell-free system may be aglycosylated depending on the source of the cells.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.*, 1983, 62:1-13, incorporated by reference in its entirety). Protein G is useful for all mouse isotypes and for human γ3 (Guss et al., *EMBO J.*, 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

11. Gamma Secretase Inhibitors (GSIs)

Provided herein are gamma secretase inhibitors (GSIs) (e.g., BMS-986405) that may be used in combination with conjugates of antibodies to BCMA provided herein. Any of the conjugates of antibodies to BCMA provided herein, e.g., Conjugate 4, may be used in combination with a GSI. In certain embodiments, the antibody conjugates provided herein are administered in combination with a gamma secretase inhibitor (GSI), e.g., BMS-986405 (Bristol-Myers Squibb, formerly known as JSMD194 or LY3039478), avagacestat (BMS-708163; Bristol-Myers Squibb), MK-0752 (Merck & Co.), R04929097 (Roche), semagacestat (LY-450139; Eli Lilly & Co.), DAPT (N—[N-(3,5-Difluorophenylacetyl-L-alanyl)]-S-phenylglycine t-Butyl ester), L685, 458, compound E ((s,s)-2-(3,5-Difluorophenyl)-acetylamino1-N-(1-methyl-2-oxo-5-phenyl-2,3- -dihydro-1H-benzo[e][1,4]diazepin-3-yl)-propionamide), DBZ (dibenzazepine), JLK6 (7-amino-4-chloro-3-methoxyisocoumarin), or [11-endo]-N-(5,6,7,8,9,10-hexahydro-6,9-methano benzo[9][8]annulen-11-yl)-thiophene-2-sulfonamide, or a pharmaceutically acceptable salt, solid form, clathrate, solvate, tautomer or racemic mixture of the GSI.

The IUPAC Name for BMS-946405 is: 4,4,4-trifluoro-N-[(1S)-1-{[(10S)-8-(2-hydroxyethyl)-9-oxo-6,8-diazatricyclo [9.4.0.02,7]pentadeca-1(11),2(7),3,5,12,14-hexaen-10 yl]carbamoyl}ethyl]butanamide hydrate. The CA Index Name for BMS-986405 is: Butanamide, N-[(1 S)-2-[[(7S)-6,7-dihydro-5-(2-hydroxyethyl)-6-oxo-5H-pyrido[3,2-a][3] benzazepin-7-yl] amino]-1-methyl-2-oxoethyl]-4,4,4-trifluoro-hydrate).

BMS-986405 has the following formula:

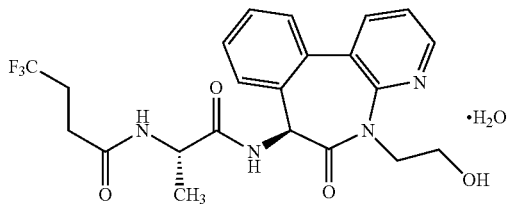

In certain embodiments, the GSI is BMS-986405, according to the formula:

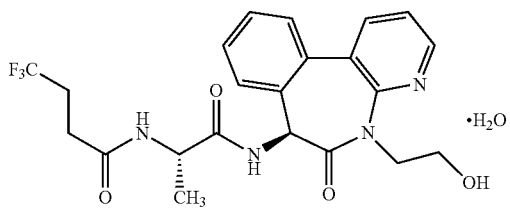

In certain embodiments, the GSI is BMS-986405, according to the formula:

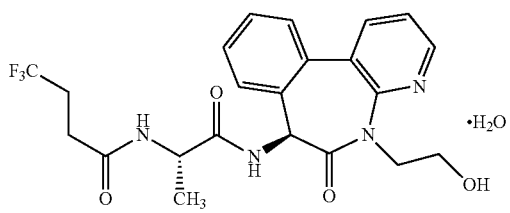

or a pharmaceutically acceptable salt, clathrate, solid form, solvate, stereoisomer, tautomer or racemic mixture thereof. In certain embodiments, the GSI is BMS-986405, according to the formula:

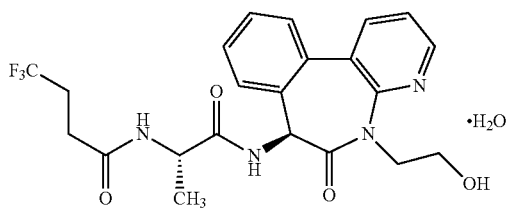

or a pharmaceutically acceptable salt thereof.

In certain embodiments, an effective amount of BMS-986405 is administered to a subject. In certain embodiments, BMS-986405 is administered to the subject orally. In certain embodiments, BMS-986405 is administered to the subject as capsules.

12. Pharmaceutical Compositions and Methods of Administration

The antibody conjugates provided herein can be formulated into pharmaceutical compositions using methods available in the art and those disclosed herein. Likewise, the gamma secretase inhibitors (e.g., BMS-986405) provided herein can be formulated into pharmaceutical compositions using methods available in the art and those disclosed herein. Any of the antibody conjugates provided herein can be provided in the appropriate pharmaceutical composition and be administered by a suitable route of administration.

The methods provided herein encompass administering pharmaceutical compositions comprising at least one antibody conjugate provided herein and one or more compatible and pharmaceutically acceptable carriers. Likewise, the methods provided herein encompass administering pharmaceutical compositions comprising at least one gamma secretase inhibitor (e.g., BMS-986405) provided herein and one or more compatible and pharmaceutically acceptable carriers. In this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like.

Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Martin, E. W., *Remington's Pharmaceutical Sciences*.

In clinical practice the pharmaceutical compositions or antibody conjugates or gamma secretase inhibitors provided herein may be administered by any route known in the art. Exemplary routes of administration include, but are not limited to, the inhalation, intraarterial, intradermal, intramuscular, intraperitoneal, intravenous, nasal, parenteral, pulmonary, and subcutaneous routes. In some embodiments, a pharmaceutical composition or antibody conjugate provided herein is administered parenterally.

The compositions for parenteral administration can be emulsions or sterile solutions. Parenteral compositions may include, for example, propylene glycol, polyethylene glycol, vegetable oils, and injectable organic esters (e.g., ethyl oleate). These compositions can also contain wetting, isotonizing, emulsifying, dispersing and stabilizing agents. Sterilization can be carried out in several ways, for example using a bacteriological filter, by radiation or by heating. Parenteral compositions can also be prepared in the form of sterile solid compositions which can be dissolved at the time of use in sterile water or any other injectable sterile medium.

In some embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibody conjugates.

The pharmaceutical composition may comprise one or more pharmaceutical excipients. Any suitable pharmaceutical excipient may be used, and one of ordinary skill in the art is capable of selecting suitable pharmaceutical excipients. Non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific antibody in the dosage form. The composition or single unit dosage form, if desired, can also contain minor amounts of wetting or emulsifying agents, or pH buffering agents. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a co-solvent. Illustrative examples of co-solvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an antibody conjugate, since, in some embodiments, water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition can be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Lactose-free compositions provided herein can comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pre gelatinized starch, and magnesium stearate.

Also provided are pharmaceutical compositions and dosage forms that comprise one or more excipients that reduce the rate by which an antibody or antibody-conjugate will decompose. Such excipients, which are referred to herein as "stabilizers," include, but are not limited to, antioxidants such as ascorbic acid, pH buffers, or salt buffers.

12.1. Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

12.2. Dosage and Unit Dosage Forms

In human therapeutics, the doctor will determine the posology which they consider most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies.

The amount of the antibody conjugate, gamma secretase inhibitor (GSI) (e.g., BMS-986405), or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of the antibody conjugate, gamma secretase inhibitor (GSI) (e.g., BMS-986405), or composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiments, the dosage of the antibody conjugate provided herein, based on weight of the antibody, administered to prevent, treat, manage, or ameliorate a disorder, or one or more symptoms thereof in a subject is 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.25 mg/kg, 1.5 mg/kg, 1.75 mg/kg, 2 mg/kg, 2.25 mg/kg, 2.5 mg/kg, 2.75 mg/kg, 3 mg/kg, 3.25 mg/kg, 3.5 mg/kg, 3.75 mg/kg, 4 mg/kg, 4.25 mg/kg, 4.5 mg/kg, 4.75 mg/kg, 5 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.25 mg/kg, 8.5 mg/kg, 8.75 mg/kg, 9.0 mg/kg, 9.25 mg/kg, 9.5 mg/kg, 9.75 mg/kg, 10 mg/kg, 10.25 mg/kg, 10.5 mg/kg, 10.75 mg/kg, 11.0 mg/kg, 11.25 mg/kg, 11.5 mg/kg, 11.75 mg/kg, 12.0 mg/kg, 12.25 mg/kg, 12.5 mg/kg, 12.75 mg/kg, 13.0 mg/kg, 13.25 mg/kg, 13.5 mg/kg, 13.75 mg/kg, 14.0 mg/kg, 14.25 mg/kg, 14.5 mg/kg, 14.75 mg/kg, or 15 mg/kg or more of a subject's body weight. In certain embodiments, the dosage of the antibody conjugate provided herein, based on weight of the antibody, administered to prevent, treat, manage, or ameliorate a disorder, or one or more symptoms thereof in a subject is about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.25 mg/kg, 1.5 mg/kg, 1.75 mg/kg, 2 mg/kg, 2.25 mg/kg, 2.5 mg/kg, 2.75 mg/kg, 3 mg/kg, 3.25 mg/kg, 3.5 mg/kg, 3.75 mg/kg, 4 mg/kg, 4.25 mg/kg, 4.5 mg/kg, 4.75 mg/kg, 5 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.25 mg/kg, 8.5 mg/kg, 8.75 mg/kg, 9.0 mg/kg, 9.25 mg/kg, 9.5 mg/kg, 9.75 mg/kg, 10 mg/kg, 10.25 mg/kg, 10.5 mg/kg, 10.75 mg/kg, 11.0 mg/kg, 11.25 mg/kg, 11.5 mg/kg, 11.75 mg/kg, 12.0 mg/kg, 12.25 mg/kg, 12.5 mg/kg, 12.75 mg/kg, 13.0 mg/kg, 13.25 mg/kg, 13.5 mg/kg, 13.75 mg/kg, 14.0 mg/kg, 14.25 mg/kg, 14.5 mg/kg, 14.75 mg/kg, or 15 mg/kg or more of a subject's body weight. In another embodiment, the dosage of the antibody conjugate provided herein, based on weight of the antibody, administered to prevent, treat, manage, or ameliorate a disorder, or one or more symptoms thereof in a subject is about 0.1 mg/kg to 15 mg/kg, 0.1 mg/kg to 14 mg/kg, 0.1 mg/kg to 13 mg/kg, 0.1 mg/kg to 12 mg/kg, 0.1 mg/kg to 11 mg/kg, 0.1 mg/kg to 10 mg/kg, 0.1 mg/kg to 9 mg/kg, 0.1 mg/kg to 8 mg/kg, 0.1 mg/kg to 7 mg/kg, 0.1 mg/kg to 6 mg/kg, 0.1 mg/kg to 5 mg/kg, 0.1 mg/kg to 4 mg/kg, 0.1 mg/kg to 3 mg/kg, 0.1 mg/kg to 2 mg/kg, 0.1 mg/kg to 1.0 mg/kg, 0.1 mg/kg to 0.5 mg/kg, 0.3 mg/kg to 15 mg/kg, 0.3 mg/kg to 14 mg/kg, 0.3 mg/kg to 13 mg/kg, 0.3 mg/kg to 12 mg/kg, 0.3 mg/kg to 11 mg/kg, 0.3 mg/kg to 10 mg/kg, 0.3 mg/kg to 9 mg/kg, 0.3 mg/kg to 8 mg/kg, 0.3 mg/kg to 7 mg/kg, 0.3 mg/kg to 6 mg/kg, 0.3 mg/kg to 5 mg/kg, 0.3 mg/kg to 4 mg/kg, 0.3 mg/kg to 3 mg/kg, 0.3 mg/kg to 2 mg/kg, 0.3 mg/kg to 1.0 mg/kg, 1.0 mg/kg to 15 mg/kg, 1.0 mg/kg to 14 mg/kg, 1.0 mg/kg to 13 mg/kg, 1.0 mg/kg to 12 mg/kg, 1.0 mg/kg to 11 mg/kg, 1.0 mg/kg to 10 mg/kg, 1.0 mg/kg to 9 mg/kg, 1.0 mg/kg to 8 mg/kg, 1.0 mg/kg to 7 mg/kg, 1.0 mg/kg to 6 mg/kg, 1.0 mg/kg to 5 mg/kg, 1.0 mg/kg to 4 mg/kg, 1.0 mg/kg to 3 mg/kg, 1.0 mg/kg to 2 mg/kg, 3.0 mg/kg to 15 mg/kg, 3.0 mg/kg to 14 mg/kg, 3.0 mg/kg to 13 mg/kg, 3.0 mg/kg to 12 mg/kg, 3.0 mg/kg to 11 mg/kg, 3.0 mg/kg to 10 mg/kg, 3.0 mg/kg to 9 mg/kg, 3.0 mg/kg to 8 mg/kg, 3.0 mg/kg to 7 mg/kg, 3.0 mg/kg to 6 mg/kg, 3.0 mg/kg to 5 mg/kg, or 3.0 mg/kg to 4 mg/kg.

In another embodiment, the dosage of the antibody conjugate or a composition provided herein administered to prevent, treat, manage, or ameliorate a disorder, or one or more symptoms thereof in a subject is 0.1 mg, 0.25 mg, 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 15 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, or 200 mg. In another embodiment, the dosage of the antibody conjugate or a composition provided herein administered to prevent, treat, manage, or ameliorate a disorder, or one or more symptoms thereof in a subject is about 0.1 mg, 0.25 mg, 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, 10 mg, 15 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, or 200 mg. In another embodiment, the dosage of the antibody conjugate or a composition provided herein administered to prevent, treat, manage, or ameliorate a disorder, or one or more symptoms thereof in a subject is about 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg. In another embodiment, the dosage of the antibody conjugate or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg. In another embodiment, the dosage of the antibody conjugate or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 mg to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg. In another embodiment, the dosage of the antibody conjugate or a composition provided herein administered to prevent, treat, manage, or ameliorate a disorder, or one or more symptoms thereof in a subject is about 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg. In another embodiment, the dosage of the antibody conjugate or a composition provided herein administered to prevent, treat, manage, or ameliorate a disorder, or one or more symptoms thereof in a subject is about 10 mg to 2000 mg, 10 mg to 1900 mg, 10 mg to 1800 mg, 10 mg to 1700 mg, 10 mg to 1600 mg, 10 mg to 1500 mg, 10 mg to 1400 mg, 10 mg to 1300 mg, 10 mg to 1200 mg, 10 mg to 1100 mg, 10 mg to 1000 mg, 10 mg to 900 mg, 10 mg to 800 mg, 10 mg to 700 mg, 10 mg to 600 mg, 10 mg to 500 mg, 10 mg to 400 mg, 10 mg to 300 mg, 10 mg to 200 mg, 10 mg to 100 mg, 15 mg to 2000 mg, 15 mg to 1900 mg, 15 mg to 1800 mg, 15 mg to 1700 mg, 15 mg to 1600 mg, 15 mg to 1500 mg, 15 mg to 1400 mg, 15 mg to 1300 mg, 15 mg to 1200 mg, 15 mg to 1100 mg, 15 mg to 1000 mg, 15 mg to 900 mg, 15 mg to 800 mg, 15 mg to 700 mg, 15 mg to 600 mg, 15 mg to 500 mg, 15 mg to 400 mg, 15 mg to 300 mg, 15 mg to 200 mg, or 15 mg to 100 mg.

In another embodiment, the dosage of the gamma secretase inhibitor (e.g., BMS-986405) provided herein administered to prevent, treat, manage, or ameliorate a disorder, or one or more symptoms thereof in a subject is 10 mg, 15 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 40 mg, 45 mg, or 50 mg. In another embodiment, the dosage of the gamma secretase inhibitor (e.g., BMS-986405) provided herein administered to prevent, treat, manage, or ameliorate a disorder, or one or more symptoms thereof in a subject is about 10 mg, 15 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 40 mg, 45 mg, or 50 mg. In another embodiment, the dosage of the gamma secretase inhibitor (e.g., BMS-986405) provided herein administered to prevent, treat, manage, or ameliorate a disorder, or one or more symptoms thereof in a subject is 10 mg to 50 mg, 10 mg to 45 mg, 10 mg to 40 mg, 10 mg to 35 mg, 10 mg to 30 mg, 10 mg to 25 mg, 10 mg to 20 mg, 10 mg to 15 mg, 20 mg to 50 mg, 20 mg to 45 mg, 20 mg to 40 mg, 20 mg to 35 mg, 20 mg to 30 mg, or 20 mg to 25 mg. In another embodiment, the dosage of the gamma secretase inhibitor (e.g., BMS-986405) provided herein administered to prevent, treat, manage, or ameliorate a disorder, or one or more symptoms thereof in a subject is about 10 mg to 50 mg, 10 mg to 45 mg, 10 mg to 40 mg, 10 mg to 35 mg, 10 mg to 30 mg, 10 mg to 25 mg, 10 mg to 20 mg, 10 mg to 15 mg, 20 mg to 50 mg, 20 mg to 45 mg, 20 mg to 40 mg, 20 mg to 35 mg, 20 mg to 30 mg, or 20 mg to 25 mg.

The dose can be administered according to a suitable schedule, for example, once, two times, three times, or for times weekly. In certain embodiments, the dose can be administered once every three weeks or once every four weeks. It may be necessary to use dosages of the antibody conjugate or the gamma secretase inhibitor (GSI) outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody conjugate, gamma secretase inhibitor (GSI), or composition provided herein followed by one or more maintenance doses.

In certain embodiments, a dose of an antibody conjugate, gamma secretase inhibitor, or composition provided herein can be administered to achieve a steady-state concentration of the antibody, gamma secretase inhibitor (GSI), or composition provided herein in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, 75 days, 3 months, or 6 months.

The antibody conjugates disclosed herein (e.g., Conjugate 4) can be administered prior to (e.g., just prior to), concurrently with, or after (e.g., shortly after) the administration of the gamma secretase inhibitor (GSI) provided herein (e.g., BMS-986405). In certain embodiments, the antibody conjugates disclosed herein (e.g., Conjugate 4) can be administered 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours or 24 hours prior to the administration of the gamma secretase inhibitor (GSI) provided herein (e.g., BMS-986405). In certain embodiments, the antibody conjugates disclosed herein (e.g., Conjugate 4) can be administered 1 day, 2 days, 3 days, 4 days, 5 days, 6 days, or 7 days prior to the administration of the gamma secretase inhibitor (GSI) provided herein (e.g., BMS-986405). In certain embodiments, the antibody conjugates disclosed herein (e.g., Conjugate 4) can be administered 1 week, 2 weeks, 3 weeks, or 4 weeks prior to the administration of the gamma secretase inhibitor (GSI) provided herein (e.g., BMS-986405). In certain embodiments, the antibody conjugates disclosed herein (e.g., Conjugate 4) can be administered 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours or 24 hours after the administration of the gamma secretase inhibitor (GSI) provided herein (e.g., BMS-986405). In certain embodiments, the antibody conjugates disclosed herein (e.g., Conjugate 4) can be administered 1 day, 2 days, 3 days, 4 days, 5 days, 6 days, or 7 days after the administration of the gamma secretase inhibitor (GSI) provided herein (e.g., BMS-986405). In certain embodiments, the antibody conjugates disclosed herein (e.g., Conjugate 4) can be administered 1 week, 2 weeks, 3 weeks, or 4 weeks after the administration of the gamma secretase inhibitor (GSI) provided herein (e.g., BMS-986405). In certain embodiments, the effective amount of the antibody conjugate (e.g., Conjugate 4) is administered to the subject once every three weeks and the effective amount of BMS-986405 is administered to the subject three times every week during a 21-day cycle. In certain embodiments, the effective amount of the antibody conjugate (e.g., Conjugate 4) and the effective amount of the gamma secretase inhibitor (GSI) (e.g., BMS-986405) are administered to the subject on an empty stomach. In certain embodiments, the effective amount of the antibody conjugate (e.g., Conjugate 4) is administered to the subject on an empty stomach. In certain embodiments, the effective amount of the gamma secretase inhibitor (GSI) (e.g., BMS-986405) is administered to the subject on an empty stomach. In certain embodiments, the effective amount of the antibody conjugate (e.g., Conjugate 4) and the effective amount of the gamma secretase inhibitor (GSI) (e.g., BMS-986405) are administered to the subject on a full stomach. In certain embodiments, the effective amount of the antibody conjugate (e.g., Conjugate 4) is administered to the subject on a full stomach. In certain embodiments, the effective amount of the gamma secretase inhibitor (GSI) (e.g., BMS-986405) is administered to the subject on a full stomach.

In certain embodiments, the antibody conjugate (e.g., Conjugate 4) is administered to the subject once every three weeks and the gamma secretase inhibitor (GSI) (e.g., BMS-986405) is administered to the subject three times a week every week during a 21-day cycle (e.g., Day 1, Day 3, Day 5, Day 8, Day 10, Day 12, Day 15, Day 17, and Day 19). In certain embodiments, the antibody conjugate (e.g., Conjugate 4) is administered to the subject once every three weeks, wherein the every three weeks is the 21-day cycle (e.g., during which he gamma secretase inhibitor (GSI) (e.g., BMS-986405) is administered to the subject). In certain embodiments, the antibody conjugate (e.g., Conjugate 4) is administered to the subject on the first day (Day1) of the 21-day cycle. In certain embodiments, the antibody conjugate (e.g., Conjugate 4) is administered to the subject on the first day (Day 1) of each 21-day cycle. In certain embodiments, the 21-day cycle occurs once, twice, three times, four times, five times, six times, seven times, eight times, nine times, ten times, eleven times, twelve times, thirteen times, fourteen times, or fifteen times. In certain embodiments, the effective amount of the antibody conjugate is administered to the subject on the first day (Day 1) of the 21-day cycle, and wherein the effective amount of the antibody conjugate is 0.3 mg/kg, 0.6 mg/kg, 1.25 mg/kg, 2.0 mg/kg, 3.0 mg/kg, 4.5 mg/kg, or 6.7 mg/kg. In certain embodiments, the effective amount of BMS-986405 is administered to the subject on Day 1, Day 3, Day 5, Day 8, Day 10, Day 12, Day 15, Day 17, and Day 19 of a 21-day cycle. In certain embodiments, the antibody conjugate is administered to the subject once every three weeks, wherein the amount of the antibody conjugate administered is about 0.3 mg/kg, 0.6 mg/kg, 1.0 mg/kg, 1.25 mg/kg, 1.5 mg/kg, 1.75 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.25 mg/kg, 4.5 mg/kg, 4.75 mg/kg, 5.0 mg/kg, 5.25 mg/kg, 5.5 mg/kg, 5.75 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.25 mg/kg, 7.5 mg/kg, 7.75 mg/kg, 8.0 mg/kg, 8.25 mg/kg, 8.5 mg/kg, 8.75 mg/kg, 9.0 mg/kg, 9.25 mg/kg, 9.5 mg/kg, 9.75 mg/kg, or 10.0 mg/kg of the subject's body weight and the gamma secretase inhibitor (GSI) (e.g., BMS-986405) is administered to the subject three times a week every week during a 21-day cycle, wherein the amount of the gamma secretase inhibitor (GSI) (e.g., BMS-986405) is about 25 mg. In certain embodiments, the antibody conjugate is administered to the subject once every three weeks, wherein the amount of the antibody conjugate administered is about 0.3 mg/kg, and the gamma secretase inhibitor (GSI) (e.g., BMS-986405) is administered to the subject three times a week every week during a 21-day cycle, wherein the amount of the gamma secretase inhibitor (GSI) (e.g., BMS-986405) is about 25 mg. In certain embodiments, the antibody conjugate is administered to the subject once every three weeks, wherein the amount of the antibody conjugate administered is about 0.6 mg/kg, and the gamma secretase inhibitor (GSI) (e.g., BMS-986405) is administered to the subject three times a week every week during a 21-day cycle, wherein the amount of the gamma secretase inhibitor (GSI) (e.g., BMS-986405) is about 25 mg. In certain embodiments, the antibody conjugate is administered to the subject once every three weeks, wherein the amount of the antibody conjugate administered is about 1.25 mg/kg, and the gamma secretase inhibitor (GSI) (e.g., BMS-986405) is administered to the subject three times a week every week during a 21-day cycle, wherein the amount of the gamma secretase inhibitor (GSI) (e.g., BMS-986405) is about 25 mg. In certain embodiments, the antibody conjugate is administered to the subject once every three weeks, wherein the amount of the antibody conjugate administered is about 2.0 mg/kg, and the gamma secretase inhibitor (GSI) (e.g., BMS-986405) is administered to the subject three times a week every week during a 21-day cycle, wherein the amount of the gamma secretase inhibitor (GSI) (e.g., BMS-986405) is about 25 mg. In certain embodiments, the antibody conjugate is administered to the subject once every three weeks, wherein the amount of the antibody conjugate administered is about 3.0 mg/kg, and the gamma secretase inhibitor (GSI) (e.g., BMS-986405) is administered to the subject three times a week every week during a 21-day cycle, wherein the amount of the gamma secretase inhibitor (GSI) (e.g., BMS-986405) is about 25 mg. In certain embodiments, the antibody conjugate is administered to the subject once every three weeks, wherein the amount of the antibody conjugate administered is about 4.5 mg/kg, and the gamma secretase inhibitor (GSI) (e.g., BMS-986405) is administered to the subject three times a week every week during a 21-day cycle, wherein the amount of the gamma secretase inhibitor (GSI) (e.g., BMS-986405) is about 25 mg. In certain embodiments, the antibody conjugate is administered to the subject once every three weeks, wherein the amount of the antibody conjugate administered is about 6.7 mg/kg, and the gamma secretase inhibitor (GSI) (e.g., BMS-986405) is administered to the subject three times a week every week during a 21-day cycle, wherein the amount of the gamma secretase inhibitor (GSI) (e.g., BMS-986405) is about 25 mg. In certain embodiments, the antibody conjugate is administered to the subject once every three weeks, wherein the amount of the antibody conjugate administered is about 10.0 mg/kg, and the gamma secretase inhibitor (GSI) (e.g., BMS-986405) is administered to the subject three times a week every week during a 21-day cycle, wherein the amount of the gamma secretase inhibitor (GSI) (e.g., BMS-986405) is about 25 mg. In certain embodiments, the amount of the antibody conjugate administered is an effective amount. In certain embodiments, the amount of the antibody conjugate administered is an effective amount, wherein the effective amount is about 0.3 mg/kg, 0.6 mg/kg, 1.0 mg/kg, 1.25 mg/kg, 1.5 mg/kg, 1.75 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.25 mg/kg, 4.5 mg/kg, 4.75 mg/kg, 5.0 mg/kg, 5.25 mg/kg, 5.5 mg/kg, 5.75 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.25 mg/kg, 7.5 mg/kg, 7.75 mg/kg, 8.0 mg/kg, 8.25 mg/kg, 8.5 mg/kg, 8.75 mg/kg, 9.0 mg/kg, 9.25 mg/kg, 9.5 mg/kg, 9.75 mg/kg, or 10.0 mg/kg of the subject's body weight. In certain embodiments, the amount of the gamma secretase inhibitor (GSI) (e.g., BMS-986405) administered is an effective amount. In certain embodiments, the amount of the gamma secretase inhibitor (GSI) (e.g., BMS-986405) administered is an effective amount, wherein the effective amount is 10 mg, 15 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 40 mg, 45 mg, or 50 mg. In certain embodiments, the amount of the gamma secretase inhibitor (GSI) (e.g., BMS-986405) administered is an effective amount, wherein the effective amount is 25 mg.

In certain embodiments, wherein the antibody conjugate is administered as a monotherapy, the antibody conjugate is administered to the subject once every three weeks. In certain embodiments, the antibody conjugate is administered to the subject once every three weeks and the amount of the antibody conjugate administered is about 0.3 mg/kg, 0.6 mg/kg, 1.0 mg/kg, 1.25 mg/kg, 1.5 mg/kg, 1.75 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.25 mg/kg, 4.5 mg/kg, 4.75 mg/kg, 5.0 mg/kg, 5.25 mg/kg, 5.5 mg/kg, 5.75 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.25 mg/kg, 7.5 mg/kg, 7.75 mg/kg, 8.0 mg/kg, 8.25 mg/kg, 8.5 mg/kg, 8.75 mg/kg, 9.0 mg/kg, 9.25 mg/kg, 9.5 mg/kg, 9.75 mg/kg, or 10.0 mg/kg of the subject's body weight. In certain embodiments, the antibody conjugate is administered to the subject once every three weeks and the amount of the antibody conjugate administered is about 0.3 mg/kg. In certain embodiments, the antibody conjugate is administered to the subject once every three weeks and the amount of the antibody conjugate administered is about 0.6 mg/kg. In certain embodiments, the antibody conjugate is administered to the subject once every three weeks and the amount of the antibody conjugate administered is about 1.25 mg/kg. In certain embodiments, the antibody conjugate is administered to the subject once every three weeks and the amount of the antibody conjugate administered is about 2.0 mg/kg. In certain embodiments, the antibody conjugate is administered to the subject once every three weeks and the amount of the antibody conjugate administered is about 3.0 mg/kg. In certain embodiments, the antibody conjugate is administered to the subject once every three weeks and the amount of the antibody conjugate administered is about 4.5 mg/kg. In certain embodiments, the antibody conjugate is administered to the subject once every three weeks and the amount of the antibody conjugate administered is about 6.7 mg/kg. In certain embodiments, the antibody conjugate is administered to the subject once every three weeks and the amount of the antibody conjugate administered is about 10.0 mg/kg. In certain embodiments, the amount of the antibody conjugate administered is an effective amount. In certain embodiments, the amount of the antibody conjugate administered is an effective amount, wherein the effective amount is about 0.3 mg/kg, 0.6 mg/kg, 1.0 mg/kg, 1.25 mg/kg, 1.5 mg/kg, 1.75 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.25 mg/kg, 4.5 mg/kg, 4.75 mg/kg, 5.0 mg/kg, 5.25 mg/kg, 5.5 mg/kg, 5.75 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.25 mg/kg, 7.5 mg/kg, 7.75 mg/kg, 8.0 mg/kg, 8.25 mg/kg, 8.5 mg/kg, 8.75 mg/kg, 9.0 mg/kg, 9.25 mg/kg, 9.5 mg/kg, 9.75 mg/kg, or 10.0 mg/kg of the subject's body weight.

In certain embodiments, wherein the antibody conjugate is administered as a monotherapy, the antibody conjugate is administered to the subject once every four weeks. In certain embodiments, the antibody conjugate is administered to the subject once every four weeks and the amount of the antibody conjugate administered is about 0.3 mg/kg, 0.6 mg/kg, 1.0 mg/kg, 1.25 mg/kg, 1.5 mg/kg, 1.75 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.25 mg/kg, 4.5 mg/kg, 4.75 mg/kg, 5.0 mg/kg, 5.25 mg/kg, 5.5 mg/kg, 5.75 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.25 mg/kg, 7.5 mg/kg, 7.75 mg/kg, 8.0 mg/kg, 8.25 mg/kg, 8.5 mg/kg, 8.75 mg/kg, 9.0 mg/kg, 9.25 mg/kg, 9.5 mg/kg, 9.75 mg/kg, or 10.0 mg/kg of the subject's body weight. In certain embodiments, the antibody conjugate is administered to the subject once every four weeks and the amount of the antibody conjugate administered is about 0.3 mg/kg. In certain embodiments, the antibody conjugate is administered to the subject once every four weeks and the amount of the antibody conjugate administered is about 0.6 mg/kg. In certain embodiments, the antibody conjugate is administered to the subject once every four weeks and the amount of the antibody conjugate administered is about 1.25 mg/kg. In certain embodiments, the antibody conjugate is administered to the subject once every four weeks and the amount of the antibody conjugate administered is about 2.0 mg/kg. In certain embodiments, the antibody conjugate is administered to the subject once every four weeks and the amount of the antibody conjugate administered is about 3.0 mg/kg. In certain embodiments, the antibody conjugate is administered to the subject once every four weeks and the amount of the antibody conjugate administered is about 4.5 mg/kg. In certain embodiments, the antibody conjugate is administered to the subject once every four weeks and the amount of the antibody conjugate administered is about 6.7 mg/kg. In certain embodiments, the antibody conjugate is administered to the subject once every four weeks and the amount of the antibody conjugate administered is about 10.0 mg/kg. In certain embodiments, the amount of the antibody conjugate administered is an effective amount. In certain embodiments, the amount of the antibody conjugate administered is an effective amount, wherein the effective amount is about 0.3 mg/kg, 0.6 mg/kg, 1.0 mg/kg, 1.25 mg/kg, 1.5 mg/kg, 1.75 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.25 mg/kg, 4.5 mg/kg, 4.75 mg/kg, 5.0 mg/kg, 5.25 mg/kg, 5.5 mg/kg, 5.75 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.25 mg/kg, 7.5 mg/kg, 7.75 mg/kg, 8.0 mg/kg, 8.25 mg/kg, 8.5 mg/kg, 8.75 mg/kg, 9.0 mg/kg, 9.25 mg/kg, 9.5 mg/kg, 9.75 mg/kg, or 10.0 mg/kg of the subject's body weight.

12.3. Additional Combination Therapies and Formulations

The antibody conjugates disclosed herein (e.g., Conjugate 4) may be administered as a monotherapy or in combination with a gamma secretase inhibitor (GSI) as provided herein (e.g., BMS-986405). In certain embodiments that comprise using conjugates of antibodies to BCMA in combination with a gamma secretase inhibitor (GSI), one or more additional therapeutic agents may be used as part of the compositions, therapeutic formulations, and methods of treatment provided herein. In certain embodiments, conjugates of antibodies to BCMA used in combination with a gamma secretase inhibitor (GSI) may be used in combination with one or more chemotherapeutic agents disclosed herein, and methods of treatment comprising administering such combinations to subjects in need thereof. Examples of chemotherapeutic agents include, but are not limited to, Bendamustine (TREANDA®, Cephalon), Venetoclax (VENCLEXTA®, Abbvie, Genentech), Denosumab (XGEVA®, Amgen; PROLIA®, Amgen), Carfilzomib (KYPROLIS®, Amgen), Ixazomib (NINLARO®, Takeda), Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially uncialamycin, calicheamicin gammall, and calicheamicin omegall (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pladienolide B, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

In certain embodiments, provided are compositions, therapeutic formulations, and methods of treatment or uses comprising any of the antibody conjugates used in combination with gamma secretase inhibitors (GSIs) provided herein in combination with one or more PD-1 or PD-L1 inhibitors, and methods of treatment comprising administering such combinations to subjects in need thereof. In some embodiments, the one or more PD-1 or PD-L1 inhibitors comprise a small molecule blocker of the PD-1 or PD-L1 pathway. In some embodiments, the one or more PD-1 or PD-L1 inhibitors comprise an antibody that inhibits PD-1 or PD-L1 activity. In some embodiments, the one or more PD-1 or PD-L1 inhibitors are selected from the group consisting of: CA-170, BMS-8, BMS-202, BMS-936558, CK-301, and AUNP12. In some embodiments, the one or more PD-1 or PD-L1 inhibitors are selected from the group consisting of: avelumab, nivolumab, pembrolizumab, atezolizumab, durvalumab, AMP-224 (GlaxoSmithKline), MEDI0680/AMP-514 (AstraZeneca), PDR001 (Novartis), cemiplimab, TSR-042 (Tesaro, GlaxoSmithKline), Tizlelizumab/BGB-A317 (Beigene), CK-301 (Checkpoint Therapeutics), BMS-936559 (Bristol-Meyers Squibb), cemiplimab (Regeneron), camrelizumab, sintilimab, toripalimab, genolimzumab, and A167 (Sichuan Kelun-Biotech Biopharmaceutical). In some embodiments, the one or more PD-1 or PD-L1 inhibitors are selected from the group consisting of: MGA012 (Incyte/MacroGenics), PF-06801591 (Pfizer/Merck KGaA), LY3300054 (Eli Lilly), FAZ053 (Novartis), PD-11 (Novartis), CX-072 (CytomX), BGB-A333 (Beigene), BI 754091 (Boehringer Ingelheim), JNJ-63723283 (Johnson and Johnson/Jannsen), AGEN2034 (Agenus), CA-327 (Curis), CX-188 (CytomX), STI-A1110 (Servier), JTX-4014 (Jounce), AM0001 (Armo Biosciences, Eli Lilly), CBT-502 (CBT Pharmaceuticals), FS118 (F-Star/Merck KGaA), XmAb20717 (Xencor), XmAb23104 (Xencor), AB122 (Arcus Biosciences), KY1003 (Kymab), RXI-762 (RXi). In some embodiments, the one or more PD-1 or PD-L1 inhibitors are selected from the group consisting of: PRS-332 (*Pieris* Pharmaceuticals), ALPN-202 (Alpine Immune Science), TSR-075 (Tesaro/Anaptys Bio), MCLA-145 (Merus), MGD013 (Macrogenics), MGD019 (Macrogenics), R07121661 (Hoffman-La Roche), LY3415244 (Eli Lilly). In some embodiments, the one or more PD-1 or PD-L1 inhibitors are selected from an anti-PD1 monospecific or bi-specific antibody described in, for example, WO 2016/077397, WO 2018/156777, and International Application No. PCT/US2013/034213, filed May 23, 2018.

In certain embodiments, provided are compositions, therapeutic formulations, and methods of treatment or uses comprising any of the antibody conjugates used in combination with gamma secretase inhibitors (GSIs) provided herein in combination with one or more LAG3 inhibitors, and methods of treatment comprising administering such combinations to subjects in need thereof. In some embodiments, the one or more LAG3 inhibitors comprise a small molecule blocker of the LAG3 pathway. In some embodiments, the one or more LAG3 inhibitors comprise an antibody that inhibits LAG3 activity. In some embodiments, the one or more LAG3 inhibitors are selected from the group consisting of: IMP321 (Eftilagimod alpha, Immutep), relatilimab (Brisol-Myers Squibb), LAG525 (Novartis), MK4280 (Merck), BI 754111 (Boehringer Ingelheim), REGN3767 (Regeneron/Sanofi), Sym022 (Symphogen) and TSR-033 (Tesaro/GSK).

In certain embodiments, provided are compositions, therapeutic formulations, and methods of treatment or uses comprising any of the antibody conjugates used in combination with gamma secretase inhibitors (GSIs) provided herein in combination with one or more TIM3 inhibitors, and methods of treatment comprising administering such combinations to subjects in need thereof. In some embodiments, the one or more TIM3 inhibitors comprise a small molecule blocker of the TIM3 pathway. In some embodiments, the one or more TIM3 inhibitors comprise an antibody that inhibits TIM3 activity. In some embodiments, the one or more TIM3 inhibitors are selected from the group consisting of: TSR-022 (Tesaro), LY3321367 (Eli Lilly), Sym023 (Symphogen) and MBG453 (Novartis).

In certain embodiments, provided are compositions, therapeutic formulations, and methods of treatment or uses comprising any of the antibody conjugates used in combination with gamma secretase inhibitors (GSIs) provided herein in combination with one or more CD73 inhibitors, and methods of treatment comprising administering such combinations to subjects in need thereof. In some embodiments, the one or more CD73 inhibitors comprise a small molecule blocker of the CD73 pathway. In some embodiments, the one or more CD73 inhibitors comprise an antibody that inhibits CD73 activity. In some embodiments, the one or more CD73 inhibitors are selected from the group consisting of: MEDI9447 (Medimmune), AB680 (Arcus), and BMS-986179 (Bristol-Myers Squibb).

In certain embodiments, provided are compositions, therapeutic formulations, and methods of treatment or uses comprising any of the antibody conjugates used in combination with gamma secretase inhibitors (GSIs) provided herein in combination with one or more CD39 inhibitors, and methods of treatment comprising administering such combinations to subjects in need thereof. In some embodiments, the one or more CD39 inhibitors comprise a small molecule blocker of the CD39 pathway. In some embodiments, the one or more CD39 inhibitors comprise an antibody that inhibits CD39 activity. In some embodiments, the one or more CD39 inhibitors are selected from the group consisting of: CPI-444 (Corvus), PBF-509 (Pablobio, Novartis), MK-3814 (Merck), and AZD4635 (AstraZeneca).

In certain embodiments, the antibody conjugates used in combination with gamma secretase inhibitors (GSIs) provided herein are administered in combination with VELCADE® (bortezomib), KYPROLIS® (Carfilzomib), NINLARO® (Ixazomib). In certain embodiments, the antibody conjugates provided herein are administered in combination with FARYDAK® (panobinostat). In certain embodiments, the antibody conjugates provided herein are administered in combination with DARZALEX® (daratumumab). In certain embodiments, the antibody conjugates provided herein are administered in combination with EMPLICITI® (elotuzumab). In certain embodiments, the antibody conjugates provided herein are administered in combination with AREDIA® (pamidronate) or ZOMETA® (zolendronic acid). In certain embodiments, the antibody conjugates provided herein are administered in combination with XGEVA® (denosumab) or PROLIA® (denosumab).

The agents administered in combination with the antibody conjugates disclosed herein can be administered just prior to, concurrent with, or shortly after the administration of the antibody conjugates. In certain embodiments, the antibody conjugates provided herein are administered on a first dosing schedule, and the one or more second agents are administered on their own dosing schedules. For purposes of the present disclosure, such administration regimens are considered the administration of an antibody conjugate "in combination with" an additional therapeutically active component. Embodiments include pharmaceutical compositions in which an antibody conjugate disclosed herein is co-formulated with one or more of the chemotherapeutic agents, PD-1 inhibitors, or PD-L1 inhibitors disclosed herein.

13. Therapeutic Applications

For therapeutic applications, the antibody conjugates and gamma secretase inhibitors (GSIs) of the invention are administered to a mammal, generally a human, in a pharmaceutically acceptable dosage form such as those known in the art and those discussed above. For example, the antibody conjugates and gamma secretase inhibitors, e.g., BMS-986405, may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibody conjugates and gamma secretase inhibitors (GSIs) also are suitably administered by peritumoral, intralesional, or perilesional routes, to exert local as well as systemic therapeutic effects. The intraperitoneal route may be particularly useful, for example, in the treatment of ovarian tumors. In certain embodiments, the antibody conjugate is administered intravenously and the GS1, e.g., BMS-986405, is administered orally, for example in capsule form.

In certain embodiments, the antibody conjugates may be administered by infusion over at least 60 minutes. In certain embodiments, the antibody conjugates may be administered by infusion over at least 50 minutes. In certain embodiments, the antibody conjugates may be administered by infusion over at least 40 minutes. In certain embodiments, the antibody conjugates may be administered by infusion over at least 30 minutes. In certain embodiments, the antibody conjugates may be administered by infusion over at least 20 minutes. In certain embodiments, the antibody conjugates may be administered by infusion, wherein the first two infusions are administered over at least 60 minutes and subsequent infusions are administered over at least 30 minutes.

The antibody conjugates and gamma secretase inhibitors provided herein may be useful for the treatment of any disease or condition involving BCMA. In some embodiments, the disease or condition is a disease or condition that can be diagnosed by overexpression of BCMA. In some embodiments, the disease or condition is a disease or condition that can benefit from treatment with an anti-BCMA antibody and/or gamma secretase inhibitors (GSIs). In some embodiments, the disease or condition is a cancer. In some embodiments, the disease or condition is a leukemia, a lymphoma, or multiple myeloma.

Any suitable cancer may be treated with the combination of antibody conjugates and gamma secretase inhibitors (GSIs) provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

In some embodiments, the disease to be treated with the combination of antibody conjugates and gamma secretase inhibitors (GSIs) provided herein is gastric cancer, colorectal cancer, renal cell carcinoma, cervical cancer, non-small cell lung carcinoma, ovarian cancer, uterine cancer, endometrial carcinoma, prostate cancer, breast cancer, head and neck cancer, brain carcinoma, liver cancer, pancreatic cancer, mesothelioma, and/or a cancer of epithelial origin. In particular embodiments, the disease is colorectal cancer. In some embodiments, the disease is ovarian cancer. In some embodiments, the disease is breast cancer. In some embodiments, the disease is lung cancer. In some embodiments, the disease is head and neck cancer. In some embodiments, the disease is renal cell carcinoma. In some embodiments, the disease is brain carcinoma. In some embodiments, the disease is endometrial carcinoma.

In certain embodiments, the disease to be treated with the combination of antibody conjugates and gamma secretase inhibitors (GSIs) provided herein is multiple myeloma. In specific embodiments, the multiple myeloma is Stage I, Stage II, or Stage III according to the International Staging System or the Revised International Staging System. In certain embodiments, said multiple myeloma is newly-diagnosed multiple myeloma. In other embodiments, said multiple myeloma is relapsed or refractory multiple myeloma.

Under the International Staging System (ISS), the stages of multiple myeloma are as follows: Stage I: Serum beta-2 microglobulin <3.5 mg/L and serum albumin ≥3.5 g/dL; Stage II: Not stage I or stage III; Stage III: Serum beta-2 microglobulin ≥5.5 mg/L. Under the Revised International Staging System (R-ISS), the stages of multiple myeloma are as follows: Stage I: ISS stage I and standard-risk chromosomal abnormalities by fluorescence in situ hybridization (FISH)(that is, no high-risk) and serum lactate dehydrogenase (LDH) level at or below the upper limit of normal; Stage II: Not R-ISS stage I or III; Stage III: ISS stage III and either high-risk chromosomal abnormalities by FISH (for example, presence of del(17p) and/or translocation t(4;14) and/or translocation t(14;16)) or serum LDH level above the upper limit of normal.

Multiple myeloma may also be staged using the Durie-Salmon system. Under this system, multiple myeloma is classified as stage I, II, or III (1, 2, or 3). Each stage is further classified into A or B, depending on whether kidney function has been affected, with the B classification indicating significant kidney damage. Stage I: Patients show no symptoms; however, if the cancer has affected kidney function, the prognosis may be worse regardless of the stage. Factors characteristic of stage I include: Number of red blood cells is within or slightly below normal range; normal amount of calcium in the blood; low levels of M protein in the blood or urine; M protein <5 g/dL for IgG; <3 g/dL for IgA; <4 g/24 h for urinary light chain; and/or no bone damage on x-rays or only 1 bone lesion is visible. Stage II: More cancer cells are present in the body in stage II, and if kidney function is affected, then the prognosis worsens regardless of the stage. Criteria for stage II are defined as those that fit neither stage I nor stage III. Stage III: Many cancer cells are present in the body at stage III. Factors characteristic of this stage include: Anemia, with a hemoglobin <8.5 g/dL; hypercalcemia; advanced bone damage (3 or more bone lesions); high levels of M protein in the blood or urine; and/or M protein >7 g/dL for IgG; >5 g/dL for IgA; >12 g/24 h for urinary light chain.

In any of the above embodiments, a subject treated for cancer in accordance with the methods provided herein is a human male or human female who is ≥18 years of age.

In any of the above embodiments, a subject treated for cancer in accordance with the methods provided herein is a human with a history of multiple myeloma with relapsed and refractory disease. In some embodiments, a subject treated for cancer in accordance with the methods provided herein is a human with a history of multiple myeloma with relapsed and refractory disease, wherein the multiple myeloma with relapsed and refractory disease was nonresponsive to the most recent antimyeloma therapy administered to the subject (e.g., failure to obtain a minimal response (MR) or better) or wherein the subject has documented disease progression on or within 60 days from the last dose of the most recent antimyeloma therapy administered to the subject. In particular, embodiments, the most recent antimyeloma therapy administered to the subject is a CAR T-cell therapy. In particular embodiments, the most recent antimyeloma therapy administered to the subject is a CAR T-cell therapy and the subject has disease that is nonresponsive to the CAR T-cell therapy (e.g., failure to obtain a minimal response (MR) or better) or wherein the subject has documented disease progression beyond 60 days after CAR T cell infusion.

In some embodiments, a subject treated for cancer in accordance with the methods provided herein is a human who has received at least one (1), two (2) or three (3) prior multiple myeloma treatment regimens. In some embodiments, a subject treated for cancer in accordance with the methods provided herein is a human who has received three (3) prior multiple myeloma treatment regimens. In some embodiments, a subject treated for cancer in accordance with the methods provided herein is a human who has received two (2) prior multiple myeloma treatment regimens. In some embodiments, a subject treated for cancer in accordance with the methods provided herein is a human who has received one (1) prior multiple myeloma treatment regimen. In certain embodiments, a multiple myeloma treatment regimen comprises at least two (2) consecutive cycles of treatment. For example, a multiple myeloma treatment regimen may comprise two (2), three (3), four (4), five (5), six (6), seven (7), or eight (8) consecutive cycles of treatment. In some embodiments, the consecutive cycles of treatment may be the same or may be different treatments. In particular embodiments, each treatment regimen has at least two (2) consecutive cycles of treatment. In particular embodiments, each treatment regimen has two (2) consecutive cycles of treatment. In particular embodiments, each treatment regimen has fewer than 2 consecutive cycles of treatment, wherein the subject had progressive disease (PD) as the best response to the treatment regimen. In particular embodiments, induction with or without hematopoietic stem cell transplant and with or without maintenance therapy is a single regimen. In particular embodiments, the subject has previously received (1) a proteasome inhibitor; (2) an immunomodulatory agent; and (3) an anti-CD38 antibody. In particular embodiments, the anti-CD38 antibody is daratumumab. In particular embodiments, the subject has failed prior treatment with and/or is intolerant to therapies for relapsed and refractory MM.

In some embodiments, a subject treated for cancer in accordance with the methods provided herein is a human who has received at least one (1), two (2) or three (3) prior multiple myeloma treatment regimens. In some embodiments, a subject treated for cancer in accordance with the methods provided herein is a human who has received three (3) prior multiple myeloma treatment regimens. In some embodiments, a subject treated for cancer in accordance with the methods provided herein is a human who has received two (2) prior multiple myeloma treatment regimens. In some embodiments, a subject treated for cancer in accordance with the methods provided herein is a human who has received one (1) prior multiple myeloma treatment regimen. In particular embodiments, induction with or without hematopoietic stem cell transplant and with or without maintenance therapy is a single regimen. In particular embodiments, the subject has previously received (1) an immunomodulatory agent and/or a proteasome inhibitor; (2) an anti-CD38 monotherapy or an anti-CD38 combination regimen; and an autologous stem cell transplant. In particular embodiments, the subject has previously received (1) an immunomodulatory agent and/or a proteasome inhibitor, wherein the subject received at least two (2) complete cycles of treatment; (2) an anti-CD38 monotherapy or an anti-CD38 combination regimen; and an autologous stem cell transplant. In particular embodiments, the immunomodulatory agent is lenalidomide or pomalidomide. In particular embodiments, the proteasome inhibitor is bortezomib, carfilzomib, or ixazomib. In particular embodiments, the anti-CD38 antibody is daratumumab.

In any of the above embodiments, a subject treated for cancer in accordance with the methods provided herein is a human with measurable disease. In some embodiments, a subject treated for cancer in accordance with the methods provided herein is a human with M-protein quantities $\geq 0.5$ g/dL determined by serum protein electrophoresis (sPEP). In some embodiments, a subject treated for cancer in accordance with the methods provided herein is a human with $\geq 200$ mg/24 hours urine collection determined by urine protein electrophoresis (uPEP). In some embodiments, a subject treated for cancer in accordance with the methods provided herein is a human with serum FLC levels >100 mg/L (milligrams/liter involved light chain) and an abnormal kappa/lambda ($\kappa/\lambda$) ratio in subjects without detectable serum or urine M-protein. In some embodiments, a subject treated for cancer in accordance with the methods provided herein is a human with a serum monoclonal IgA level >0.50 g/dL, wherein the subject has immunoglobulin class A (IgA) myeloma, wherein the myeloma is measured by quantitative immunoglobulin measurement. In some embodiments, a subject treated for cancer in accordance with the methods provided herein is a human with a serum monoclonal IgA level $\geq 0.50$ g/dL, wherein the subject immunoglobulin class A (IgA) myeloma, wherein the myeloma can only be measured by quantitative immunoglobulin measurement.

In any of the above embodiments, a subject treated for cancer in accordance with the methods provided herein consents to serial bone marrow aspirations and/or biopsies.

In any of the above embodiments, a subject treated for cancer in accordance with the methods provided herein is a human that has an ECOG PS of 0-1.

In any of the above embodiments, a subject treated for cancer in accordance with the methods provided herein is a human with absolute neutrophil count (ANC)$\geq 1.0 \times 10^9$/L without growth factor support for 7 days. In some embodiments, a subject treated for cancer in accordance with the methods provided herein is a human with absolute neutrophil count (ANC)$\geq 1.0 \times 10^9$/L without growth factor support for 14 days, wherein the subject has been administered pegfilgrastim. In some embodiments, a subject treated for cancer in accordance with the methods provided herein is a human with (1) platelets (plt)$\geq 75 \times 10^9$/L, wherein the subject has not received a transfusion for 7 days, or (2) plt $\geq 50 \times 10^9$/L and bone marrow (BM) plasma cells $\geq 50\%$. In some embodiments, a subject treated for cancer in accordance with the methods provided herein is a human with potassium within normal limits or correctable with supplements. In some embodiments, a subject treated for cancer in accordance with the methods provided herein is a human with aspartate aminotransferase (AST/SGOT) and alanine aminotransferase (ALT/SGPT)$\leq 2.5\times$ upper limit of normal (ULN). In some embodiments, a subject treated for cancer in accordance with the methods provided herein is a human with serum bilirubin $\leq 1.5 \times$ULN. In some embodiments, a subject treated for cancer in accordance with the methods provided herein is a human with $\leq 2.0 \times$ULN, wherein the subject has Gilbert's syndrome. In some embodiments, a subject treated for cancer in accordance with the methods provided herein is a human with $\leq 2.0 \times$ULN, wherein the subject has documented Gilbert's syndrome. In some embodiments, a subject treated for cancer in accordance with the methods provided herein is a human with estimated serum creatinine clearance of $\geq 60$ mL/min using the Cockcroft-Gault equation or directly calculated from the 24-hour urine collection method. In some embodiments, a subject treated for cancer in accordance with the methods provided herein is a human with international normalized ratio (INR) <1.5$\times$ULN and activated partial thromboplastin time (APTT)<1.5$\times$ULN.

In any of the above embodiments, a subject treated for cancer in accordance with the methods provided herein is a human female of childbearing potential (FCBP), wherein (1) the subject has not undergone a hysterectomy or bilateral oophorectomy; or (2) the subject has not been naturally postmenopausal for at least 24 consecutive months. In further embodiments, the female subject has committed to true abstinence from heterosexual contact or agrees to use at least two effective contraceptive methods. In further embodiments, the female subject has committed to true abstinence from heterosexual contact or agrees to use at least two effective contraceptive methods for up to 42 days following the last dose of Conjugate 4. In a particular embodiment, the contraceptive method is an oral, injectable, or implantable hormonal contraceptive; tubal ligation; an intra-uterine device; a barrier contraceptive with spermicide; or a vasectomized partner. In further embodiments, the female subject has had two negative pregnancy tests prior to receiving Conjugate 4. In a particular embodiment, negative pregnancy test is a negative serum pregnancy test, wherein sensitivity of the negative serum pregnancy test is at least 25 mIU/mL, or a negative serum or urine pregnancy test within 72 hours prior to Cycle 1 Day −1 of treatment, and within 72 hours prior to Day −1 of every subsequent cycle of treatment. In further embodiments, the female subject avoids conceiving for 42 days after the last dose of Conjugate 4. In further embodiments, the female subject avoids conceiving for 3 months after the last dose of BMS-986405. In further embodiments, the female subject agrees to ongoing pregnancy testing.

In any of the above embodiments, a subject treated for cancer in accordance with the methods provided herein is a human male practicing true abstinence or agree to use a condom during sexual contact with a pregnant female or a FCBP. In some embodiments, a subject treated for cancer in accordance with the methods provided herein is a human male practicing true abstinence or agree to use a condom during sexual contact with a pregnant female or a FCBP for at least 42 days following Conjugate 4 discontinuation and for 3 months after the last dose of BMS-986405. In a particular embodiment, the human male has undergone a successful vasectomy.

In any of the above embodiments, a subject treated for cancer in accordance with the methods provided herein is a human female of childbearing potential (FCBP), wherein (1) the subject has not undergone a hysterectomy or bilateral oophorectomy; or (2) the subject has not been naturally postmenopausal for at least 24 consecutive months. In further embodiments, the female subject has committed to true abstinence from heterosexual contact or agrees to use at least two effective contraceptive methods. In further embodiments, the female subject has committed to true abstinence from heterosexual contact or agrees to use at least two effective contraceptive methods for up to 220 days following the last dose of Conjugate 4 and for 220 days after the last dose of BMS-986405. In a particular embodiment, the contraceptive method is an oral, injectable, or implantable hormonal contraceptive; tubal ligation; an intra-uterine device; a barrier contraceptive with spermicide; or a vasectomized partner. In further embodiments, the female subject has had two negative pregnancy tests prior to receiving Conjugate 4. In a particular embodiment, negative pregnancy test is a negative serum pregnancy test, wherein sensitivity of the negative serum pregnancy test is at least 25 mIU/mL, or a negative serum or urine pregnancy test within 72 hours prior to Cycle 1 Day −1 of treatment, and within 72 hours prior to Day −1 of every subsequent cycle of treatment. In further embodiments, the female subject avoids conceiving for 220 days after the last dose of Conjugate 4. In further embodiments, the female subject avoids conceiving for 220 days after the last dose of BMS-986405. In further embodiments, the female subject agrees to ongoing pregnancy testing.

In any of the above embodiments, a subject treated for cancer in accordance with the methods provided herein is a human male practicing true abstinence or agree to use a condom during sexual contact with a pregnant female or a FCBP. In some embodiments, a subject treated for cancer in accordance with the methods provided herein is a human male practicing true abstinence or agree to use a condom during sexual contact with a pregnant female or a FCBP for at least 130 days following Conjugate 4 discontinuation and for 130 days after the last dose of BMS-986405. In a particular embodiment, the human male has undergone a successful vasectomy.

14. Affinity Purification Reagents

The antibody conjugates provided herein may be used as affinity purification agents. In this process, the antibody conjugates may be immobilized on a solid phase such a resin or filter paper, using methods well known in the art. The immobilized antibody conjugate is contacted with a sample containing the BCMA protein (or fragment thereof) to be purified, and thereafter the support is washed with a suitable solvent that will remove substantially all the material in the sample except the BCMA protein, which is bound to the immobilized antibody. Finally, the support is washed with another suitable solvent, such as glycine buffer, pH 5.0 that will release the BCMA protein from the antibody.

15. Kits

In some embodiments, a combination of an anti-BCMA antibody conjugate (e.g., Conjugate 4) and a gamma secretase inhibitor (GSI) (e.g., BMS-986405) provided herein is provided in the form of a kit, i.e., a packaged combination of reagents in predetermined amounts with instructions for performing a procedure. In some embodiments, the procedure is a diagnostic assay. In other embodiments, the procedure is a therapeutic procedure.

In certain embodiments, provided herein are kits comprising an effective amount of any of the antibody conjugates provided herein, for example, Conjugate 4, and an effective amount of BMS-986405, and instructions for use of the antibody conjugate and the BMS-986405. In certain embodiments, provided herein are kits comprising an effective amount of an antibody conjugate provided herein, for example, Conjugate 4, and an effective amount of BMS-986405, in separate containers, and instructions for use of the antibody conjugate and the BMS-986405. In a specific embodiment, the antibody conjugate is lyophilized. In another specific embodiment, the kit further comprises a fluid for reconstitution of the lyophilized antibody. In some embodiments, the kit further comprises a solvent for the reconstitution of the anti-BCMA antibody conjugate.

In certain embodiments, provided herein are kits comprising one or more doses of any of the antibody conjugates provided herein, for example, Conjugate 4, and one or more doses of BMS-986405, and instructions for use of the antibody conjugate and the BMS-986405. In a specific embodiment, the antibody conjugate is present in an amount that comprises from about 10 mg to about 1000 mg. In certain embodiments, the BMS-986405 is present in an amount that comprises about 25 mg. In certain embodiments, the kit comprises one or more containers comprising the antibody conjugate and the BMS-986405. In certain embodiments, the antibody conjugate and the BMS-986405 are in separate containers. In certain embodiments, provided herein are kits comprising an antibody conjugate provided herein, for example, Conjugate 4, and BMS-986405, in separate containers, and instructions for use of the antibody conjugate and the BMS-986405. In a specific embodiment, the antibody conjugate is lyophilized. In another specific embodiment, the kit further comprises a fluid for reconstitution of the lyophilized antibody. In some embodiments, the kit further comprises a solvent for the reconstitution of the anti-BCMA antibody conjugate.

16. Pharmaceutical Compositions

In some embodiments, the anti-BCMA antibody conjugate is provided in the form of a pharmaceutical composition. In some embodiments, the GSI, e.g., BMS-986405, is provided in the form of a pharmaceutical composition. In some embodiments, provided herein are pharmaceutical compositions that comprise an anti-BCMA antibody conjugate and a gamma secretase inhibitor (GSI) (e.g., BMS-986405). In some embodiments, the anti-BCMA antibody conjugate and the GSI are both provided to a subject.

EXAMPLES

Example 1

Generation of Anti-BCMA Antibodies

Generation and Phage Display Selection

Phage display was used to discover initial human antibody leads 2190-B01 and 2213-A06. Antibody Fab libraries were constructed using an optimized trastuzumab Fab sequence codon optimized in a modified, commercially available p3 phagemid vector (Antibody Design Labs). Briefly, the phagemid vector was modified to express Fab heavy chains as C-terminal p3 fusion proteins, and regulatory regions (start codons, restriction enzyme sites, periplasmic leader sequences) were optimized for Fab display levels. Libraries were constructed using a standard overlap extension PCR protocol with mutagenic primers targeting heavy chain complementary determining regions (CDRs). See Heckman and Pease, *Nat. Protoc.*, 2007, 2:924-932. Libraries were rescued through electroporation in M13-K07 infected SS320 *E. coli* cells. Library selections were performed using standard phage display protocols. See Rajan & Sidhu, *Methods Enzymol.*, 2012, 502:3-23; Marks & Bradbury, *Methods Mol Biol.*, 2004, 248:161-76. Following multiple selection rounds, Fab heavy chain pools were transferred into cell-free expression vectors for expression as His6 and FLAG-tagged IgG1.

Ribosome Display Selections

Ribosome display was used to discover initial human antibody leads 2137-A05 and 2137-007. Ribosome display was also used to affinity mature 2137-007, 2137-A05, 2190-B01, and 2213-A06 to generate improved derivative 2265, among others.

Antibody Fab libraries were constructed using a standard overlap extension PCR protocol with mutagenic primers targeting complementary determining regions (CDRs). See Heckman & Pease, supra. Selections for novel antibodies were performed using standard ribosome display protocols. See Hanes & Plückthun, *Proc. Natl. Acad. Sci. U.S.A*, 1997, 94:4937-4942. Specifically, Fab-based ribosome display selections were performed according to published protocols. See Stafford et al., 2014, *Protein Eng. Des. Sel.* 27:97-109; Dreier and Plückthun, 2011, *Methods Mol Biol* 687:283-306. After multiple rounds of selection, the DNA from RT-PCR output was cloned into an optimized vector for cell-free expression using standard molecular biology techniques. See Yin et al., 2012, mAbs 4:217-225. All constructs were HIS- and FLAG-tagged to streamline purification and testing during screening.

Exemplary antibodies are reported in Table 6. Antibody 4 is also referred to as "Antibody 2265-F02" herein.

TABLE 6

Antibodies produced by ribosome and phage-display

| Antibody | $V_H$ | SEQ ID NO. | $V_L$ | SEQ ID NO. |
|---|---|---|---|---|
| 4 | 2265-F02 | 13 | Trastuzumab | 14 |

Example 2

Primary Screening of Antibodies

Primary ELISA Screening of Antibody Variants

Libraries of antibody variants generated by selection workflow were transformed into *E. coli* and grown on agar plates with antibiotic (Kanamycin). Individual colonies were grown in liquid broth (TB+antibiotic Kanamycin), and used as a template for DNA amplification via rolling circle amplification (RCA). The variants were then expressed in a cell-free protein synthesis reaction as described. See Yin et al., mAbs, 2012, 4:217-225. Briefly, cell-free extracts were treated with 50 µM iodoacetamide for 30 min at RT (20° C.) and added to a premix containing cell-free components (see Cai et al., *Biotechnol Prg*, 2015, 3:823-831), 10% (v/v) RCA DNA template (approximately 10 µg/mL DNA) for HC variants of interest, and 2.5 µg/mL of the trastuzumab LC. 60 µL cell free (CF) reactions were incubated at 30° C. for 12 hr on a shaker at 650 rpm in 96-well plates. 400-1500 colonies were screened, depending on the predicted diversity of different selection campaigns. Following synthesis, each reaction was diluted 1:200 and tested for binding to human or cynomolgus BCMA-Fc protein by ELISA. Briefly, BCMA-Fc (R&D Systems, Minneapolis, MN) was coated to 384-well Maxisorp plates in 0.1M bicarbonate (pH 8.9) and blocked with 1% BSA in PBST. Antibodies from a 1:200 diluted CF reaction were incubated on the plates, washed, and detected with HRP-conjugated anti-human Fab antibodies (Jackson ImmunoResearch, West Grove, PA) and Pierce Pico Supersignal ELISA substrate (ThermoFisher Scientific)

High-Throughput Cell Binding

A high-throughput primary screen was performed to rapidly assess cell binding of antibodies produced in small-scale (60 µL) cell-free reactions. In this screen, four components were combined in equal volumes to a final volume of 100 µL/well in a U-bottom 96-well plate (Greiner Cat #650201) or flat bottom 384-well plate (Greiner Cat #781201). These components are: 1) BCMA-expressing NCI-H929 cells diluted in assay buffer (1×PBS+0.2% BSA, sterile filtered) to achieve a final concentration of 500,000 cells/well, 2) BCMA-negative MOLT-4 cells stained with CellTrace Oregon Green (Invitrogen Cat #34555) and diluted in assay buffer to achieve a final concentration of 500,000 cells/well, 3) a 1:50 dilution of cell-free reaction producing the antibody of interest diluted in assay buffer, and 4) a secondary anti-human antibody (AlexaFluor 647 AffiniPure F(ab')$_2$ Donkey anti-human IgG, Fc specific; Jackson ImmunoResearch Cat #709-606-098) diluted 1:100 in assay buffer. Plates were then incubated on ice for one hour. Cells were pelleted by spinning at 1500×g for 5 minutes and resuspended in assay buffer. High-throughput flow cytometry was then performed on resuspended cells on a FACS instrument (BD Biosciences FACSCanto II or BD Biosciences LSR II), and data was analyzed with FlowJo software. Antibody binding was assessed by the proportional level of secondary antibody signal (presumably due to binding to the antibody of interest) on NCIH929 BCMA-positive cells compared to the signal on MOLT-4 BCMA-negative cells.

Example 3

Secondary Screening of Antibodies

Preparation of IgGs

The top leads from the initial round of screening were cultured and miniprepped via the Qiaprep 96 Turbo miniprep kit (Qiagen) according to manufacturer's instructions. 7.5 µg/mL miniprepped HC DNA and 2.5 µg/mL of the trastuzumab LC was added to 4 mL cell-free reactions and incubated overnight for 12 hr at 30° C., 650 rpm. Expressed variants from clarified cell-free reactions were purified via IMAC purification using a semi-automated high throughput batch purification method. Briefly, purifications were performed in a 96-well plate format where 50 µL/well of IMAC resin (Ni Sepharose High Performance, GE Healthcare) was equilibrated in IMAC binding buffer (50 mM Tris pH 8.0, 300 mM NaCl, 10 mM imidazole), incubated with 1 mL cell-free reaction for 15 minutes followed by two washes in IMAC binding buffer. His-tagged antibody variants were then eluted using 200 µL IMAC elution buffer (50 mM Tris pH 8.0, 300 mM NaCl, 500 mM imidazole) and buffer exchanged into PBS using a 96-well Zeba plate (7 kD MWCO, Thermofisher). Purified antibodies were quantified via high throughput capillary electrophoresis using the Labchip GXII (Perkin Elmer) against a Herceptin standard curve, according to manufacturer's instructions.

Preparation of scFvs

A single-chain antibody is made in either the $V_HV_L$ or $V_LV_H$ orientation with a linker sequence between the $V_H$ and $V_L$ domains. Typically scFv linkers are composed of (GGGGS)n (SEQ ID NO: 28) repeats where n=3, 4, 5, or 6 for linkers of 15, 20, 25, or 30 residues respectively. For cell-free expression, an N-terminal Met is added, but for mammalian expression a leader peptide is added. On the C-terminal end of the scFv, an Fc sequence can be added to extend in vivo half-life or the scFv can be used directly. An optional linker sequence can be incorporated between the scFv and the Fc. An exemplary scFv-Fc linker sequence is AAGSDQEPKSS (SEQ ID NO: 27). C-terminal affinity tags can optionally be added to facilitate purification and assay development. An exemplary affinity tag is a C-terminal FlagHis tag GSGDYKDDDDKGSGHHHHHH (SEQ ID NO: 25). A stop codon is typically inserted at the end of the sequence. An exemplary scFv can include an N-terminal Met residue, a $V_H$ domain, a GGGGSGGGGSGGGGS (SEQ ID NO: 26) linker, a $V_L$ domain, an AAGSDQEPKSS (SEQ ID NO: 27) linker, an Fc domain, a FlagHis tag, and a stop codon.

Differential Scanning Fluorimetry

A protein thermal shift assay was carried out by mixing the protein to be assayed with an environmentally sensitive dye (SYPRO Orange, Life Technologies Cat #S-6650) in a phosphate buffered solution (PBS), and monitoring the fluorescence of the mixture in real time as it underwent controlled thermal denaturation. Protein solutions between 0.2-2 mg/mL were mixed at a 1:1 volumetric ratio with a 1:500 PBS-diluted solution of SYPRO Orange (SYPRO Orange stock dye is 5000× in DMSO). 10 µL aliquots of the protein-dye mixture were dispensed in quadruplicate in a 384-well microplate (Bio-Rad Cat #MSP-3852), and the plate was sealed with an optically clear sealing film (Bio-Rad Cat #MSB-1001) and placed in a 384-well plate real-time thermocycler (Bio-Rad CFX384 Real Time System). The protein-dye mixture was heated from 25° C. to 95° C., at increments of 0.1° C. per cycle (~1.5° C. per minute), allowing 3 seconds of equilibration at each temperature before taking a fluorescence measurement. At the end of the experiment, the transition melting temperatures (TM1 and TM2) were determined using the Bio-Rad CFX manager software. TM1 represents the melting temperature of the Fc domain. TM2 represents the melting temperature of the Fab domain.

Biacore Off-Rate and Kinetic Analysis

Anti-Fab or anti-Fc polyclonal antibodies were immobilized onto a CM5 chip (GE Life Sciences) using amine coupling chemistry (from Amine Coupling Kit, GE Life Sciences). The immobilization steps were carried out at a flow rate of 25 µL/min in 1×HBS-EP+buffer (GE Life Sciences; 10× Stock diluted before use). The sensor surfaces were activated for 7 min with a mixture of NHS (0.05 M) and EDC (0.2 M). The anti-Fab or anti-Fc antibodies were injected over all 4 flow cells at a concentration of 25 µg/ml in 10 mM sodium acetate, pH 4.5, for 7 min. Ethanolamine (1 M, pH 8.5) was injected for 7 min to block any remaining activated groups. An average of 12,000 response units (RU) of capture antibody was immobilized on each flow cell.

Off-rate and kinetic binding experiments were performed at 25° C. using 1×HBS-EP+buffer. Test and control antibodies were injected over the anti-Fab or anti-Fc surface at concentrations of 5-10 µg/mL for 12 seconds at a flow rate of 10 µL/min on flow cells 2, 3 and 4, followed by a buffer wash for 30 seconds at the same flow rate. Kinetic characterization of antibody samples was carried out with a range of antigen concentrations from 1-100 nM and 1 injection of 0 nM antigen (for example, 100, 50, 25, 6.25, 1.56 and 0 nM). After capturing ligand (antibody) on the anti-Fab or anti-Fc surface, the analyte (human BCMA-Fc, cyno BCMA-Fc, or human BCMA from R&D Systems, custom protein production, or Sigma Aldrich, respectively) was bound for 180 seconds, followed by a 600 second dissociation phase at a flow rate of 50 µL/min. Between each ligand capture and analyte binding cycle, regeneration was carried out using 2 injections of 10 mM glycine pH 2.0 for 30 seconds at 30 µL/min, followed by a 30 second buffer wash step.

The data was fit with the Biacore T200 Evaluation software, using a 1-1 Langmuir binding model. $K_D$ (affinity, nM) was determined as a ratio of the kinetic rate constants calculated from the fits of the association and dissociation phases.

Cell Lines and Cell Culture Conditions

NCI-H929, U266B1, MOLT-4 and ARP-1, were obtained from ATCC and the Keats Lab (Tgen, Phoenix, AZ). 293T-cynoBCMA and 293T-ratBCMA recombinant cells were generated by transfecting 293T cells with a plasmid containing cynomolgus or rat BCMA cDNA sequences and selecting for the highest stable expression of cynomolgus BCMA or rat BCMA on the cell surface. NCI-H929, U266B1, and MOLT-4 cells were maintained in RPMI-1640 (Cellgro-Mediatech; Manassas, VA) supplemented with 20% heat-inactivated fetal bovine serum (Hyclone; Thermo Scientific; Waltham, MA), 1% Penicillin/Streptomycin (Cellgro-Mediatech; Manassas, VA), and 2 mmol/L-glutamax (Life Technology; Carlsbad, CA). 293T-cynoBCMA and 293T-ratBCMA cells were maintained in Ham's F-12-high glucose DMEM (50-50) (Cellgro-Mediatech; Manassas, VA) supplemented with 10% heat-inactivated fetal bovine serum (Hyclone; Thermo Scientific; Waltham, MA), 1% Penicillin/Streptomycin (Cellgro-Mediatech; Manassas, VA), and 2 mmol/L-glutamax (Life Technology; Carlsbad, CA).

Cell Binding Experiments

Variants for which sufficient protein was purified in secondary screening were tested in a fluorescence-activated cell sorting (FACS) cell-binding assay. BCMA positive NCI-H929 and 293T-cynoBCMA cells and BCMA negative 293T cells were used to screen for FACS binders. 293T cells were treated with 1 µM DAPT 24 hours prior to cell binding to prevent BCMA shedding. 6-12 point dilutions of anti-BCMA variants starting from concentrations of about 100-200 nM antibody were dispensed into each well using a BioMekFX (Beckman Coulter). Cells were then incubated on ice for 1 hr, washed with FACS buffer and incubated for 1 hr on ice with 50 mL FACS buffer containing 2.5 µg/ml Alexa647-conjugated Goat Anti-Human IgG dispensed using BioMekFX (Beckman Coulter). Cells were then washed 2× with FACS buffer and fixed for 10 minutes in 200 ml PBS with 2% paraformaldehyde (PFA) prior to fluorescence detection. Samples were acquired using a Beckton Dickinson LSRII FACS. Geometric Mean Fluorescence Intensity of BCMA antibody binding was analyzed using FlowJo® software (Tree Star, Inc.).

Cell-Killing Analysis

The internalization of the antibodies was evaluated by drugs conjugated to secondary antibodies in a cell killing assay on BCMA positive cells. BCMA-positive cell lines ARP-1 and U266B1 were used to screen for internalizing leads. Cells were washed twice with calcium and magnesium-free Dulbecco's phosphate-buffered saline (DPBS), harvested with Accutase® (Innovative Cell Technologies; San Diego, CA) and counted by the Vi-CELL Cell Viability Analyzers (Beckman Coulter, Brea, CA) A total of 12,500 cells in a volume of 25 microliter were seeded in a 384-well flat bottom white polystyrene plate (Greiner Bio-One, Monroe, NC) on the day of assay. Lead antibodies were formulated at 4× starting concentration in the cell culture medium and filtered through MultiScreenHTS 96-Well Filter Plates (Millipore; Billerica, MA). 12.5 µL of the serial diluted antibody (1:3 serial dilution starting from 100 nM) was added into treatment wells and 12.5 µL of an anti-human nanobody conjugated to according to Conjugate P (hemiasterlin via a cleavable linker) or according to Conjugate M (maytansinoid via a non-cleavable linker) was then added into each well at a fixed final concentration of 20 nM. Assay plates were cultured at 37° C. in a $CO_2$ incubator for 72 hrs before assay. For cell viability measurement, 30 µL of Cell Titer-Glo® reagent (Promega Corp. Madison, WI) was added into each well, and plates were processed as per product instructions. Relative luminescence was measured on an ENVISION® plate reader (Perkin-Elmer; Waltham, MA). Relative luminescence readings were converted to % viability using untreated cells as controls. Data was fitted with non-linear regression analysis, using a log(inhibitor) vs. response-variable slope, 4 parameter fit with GraphPad Prism (GraphPad v 5.0, Software; San Diego, CA). Data was expressed as relative cell viability (ATP content) % vs. dose of antibody.

Example 4

Characteristics of Illustrative Anti-BCMA Antibodies

Tables 7A and 7B show results obtained with antibodies produced by ribosome and phage-display of initial leads and after affinity maturation.

TABLE 7A

| Antibodies from ribosome and phage-display. | | | | | | | |
|---|---|---|---|---|---|---|---|
| | NCI-H929 (BCMA+ cells) cell binding | | 293T-cynoBCMA cell binding | | ARP-1, Conjugate M 2° antibody cell killing | | U266B1, Conjugate M 2° antibody cell killing | |
| Fab-HC Variant ID | $B_{max}$ (MFI) | Kd (nM) | $B_{max}$ (MFI) | Kd (nM) | $EC_{50}$ (nM) | Span (%) | $EC_{50}$ (nM) | Span (%) |
| 2265-F02 | 11728 | 5.2 | 23759 | 6.2 | 1.9 | 55 | 0.9 | 58 |

NK = no killing

TABLE 7B

| Antibodies from ribosome and phage-display. | | | | | | | |
|---|---|---|---|---|---|---|---|
| | Thermo-stability | Biacore, human BCMA-Fc | | | Biacore, cyno BCMA-Fc | | |
| Fab-HC Variant ID | Fab TM2 (° C.) | $k_a$ (1/Ms) | $k_d$ (1/s) | $K_D$ (M) | $k_a$ (1/Ms) | $k_d$ (1/s) | $K_D$ (M) |
| 2265-F02 | 85.0 | 5.87E+05 | 2.93E−04 | 4.99E−10 | 3.15E+05 | 1.16E−03 | 3.68E−09 |

ND = not detected

Example 5

Antibody-Drug Conjugation and Dar Ratio Determination

Antibody-drug conjugation is described in Zimmerman E S, et al. 2014, Bioconjugate Chem., 25 (2), pp 351-361. Briefly, purified anti-BCMA antibody variants were conjugated to a cytotoxic agent. Stock drug was dissolved in DMSO to a final concentration of 5 mM. The compound was diluted with PBS to 1 mM and then added to the purified protein sample in to final drug concentration of 100 µM. Mixture was incubated at RT (20° C.) for 17 hours. Unincorporated drug was removed by passing the reaction sample through a 7000 MWCO resin in Zeba plates (Thermo Scientific) equilibrated in formulation buffer. Filtrate was then passed through a MUSTANG® Q plate (Pall Corp.) to remove endotoxin.

Following purification, the purified antibody or antibody drug conjugate samples were quantified on a Caliper GXII system by comparing with by mass standards of HERCEPTIN® run on the same Protein Express LabChip (Caliper Life Sciences #760499). Samples were prepared for analysis as specified in the Protein Express Reagent Kit (Caliper Life Sciences #760328) with the exception that the samples (mixed in sample buffer+50 mM NEM) were heated at 65° C. for 10 minutes prior to analysis on the Caliper system.

Antibody drug conjugates were reduced in with 10 mM TCEP (Pierce) for 10 min at 37° C. Add 30 uL of TA30 (30% Acetonitrile, 70% of 0.1% Trifluoroacetic acid) to the reduced sample. Dissolve 20 mg of super-DHB (Sigma, part No. 50862) into TA50 (50% acetonitrile, 50% of 0.1% trifluoroacetic acid) to generate a sample matrix. Next add 0.5 uL of sample in TA30 to 0.8 uL of super-DHB matrix in TA50 and deposit onto MALDI sample plate. Spectra were acquired on a Bruker Autoflex Speed MALDI instrument with the following initial settings: Mass range 7000-70000 Da, sample rate and digitizer settings of 0.05, 0.1, 0.5, 1, 2, with realtime smoothing set at High and no baseline offset adjustment. High voltage switched On and Ion source 1 adjusted to 20 kV. Pulse ion extraction at 200 ns, matrix suppression on deflection and suppress up to 6000 Da. Peak detection algorithm is centroid with signal to noise threshold at 20, peak width at 150m/z height at 80% with baseline subtraction TopHat. Smoothing algorithm is SavtzkyGolay with width of 10m/z and cycles of 10. The drug-antibody ratio (DAR) for all samples was determined as a weighted average of the deconvoluted mass spectrum area under the curve for each conjugate.

Example 6

Chemical Characteristics of Conjugate 4

Conjugate 4 is a conjugate of antibody and drug-linker. Conjugate 4 is an aglycosylated anti-B-cell maturation antigen (anti-BCMA) humanized IgG1 antibody drug conjugate (ADC) comprised of an anti-BCMA IgG1 humanized antibody (aglycosylated 2265-F02) conjugated covalently at the non-natural amino acid (nnAA) para-azidomethyl-L-phenylalanine (pAMF) residue at nominal positions 180 and 404 by EU numbering (actual positions 186 and 410) to a 20-methyl-1-(3-methyl-3,9-dihydro-8Hdibenzo[b,f] [1,2,3]triazolo[4,5-d]azocin-8-yl)-1,5,21-trioxo-8,11,14,17-tetraoxa-4,20-diazapentacosan-25-oyl (desacetyl) maytansinoid drug-linker. The ADC, Conjugate 4, is a single predominant conjugated species (existing as a ~1:1 mixture of two regioisomers) with a drug to antibody ratio (DAR) of 4. The molecular weight of Conjugate 4 is approximately 151 kDa. A sample of Conjugate 4, prepared using the methods described herein, exhibited a DAR of 3.9 to 4, as measured and calculated using the methods described herein (see, e.g., Example 6).

Disulfide bonds in Conjugate 4 are as follows: Inter chain (LC1): Cys 24-Cys 89; Cys 135-Cys 195. Inter Chain (HC1): Cys 23-Cys 97; Cys 150-Cys 206; Cys 267-Cys 327; Cys 373-Cys 431. Inter Chain (HC2): Cys 23-Cys 97; Cys 150-Cys 206; Cys 267-Cys 327; Cys 373-Cys 431. Inter chain (LC2): Cys 24-Cys 89; Cys 135-Cys 195. Intra-LC1-HC-1: Cys 215-Cys 226. Intra-LC2-HC-2: Cys 215-Cys 226. Intra-HC-HC-Hinge-1: Cys 232-Cys 232. Intra-HC-HC-Hinge-2: Cys 235-Cys 235.

Example 7

Sequences

Table 8 provides sequences referred to herein.

TABLE 8

Sequences

| SEQ ID NO: | Molecule | Region | Scheme | Sequence |
|---|---|---|---|---|
| 1 | Human BCMA (Isoform 1, UniprotKB-Q02223) | | | MLQMAGQCSQNEYFDSLLHACIP CQLRCSSNTPPLTCQRYCNASVTN SVKGTNAILWTCLGLSLIISLAVFV LMFLLRKINSEPLKDEFKNTGSGL LGMANIDLEKSRTGDEIILPRGLEY TVEECTCEDCIKSKPKVDSDHCFP LPAMEEGATILVTTKTNDYCKSLP AALSATEIEKSISAR |
| 2 | Human BCMA (Isoform 2, UniprotKB-Q02223) | | | MLQMAGQCSQNEYFDSLLHACIP CQLRCSSNTPPLTCQRYCNARSGL LGMANIDLEKSRTGDEIILPRGLEY TVEECTCEDCIKSKPKVDSDHCFP LPAMEEGATILVTTKTNDYCKSLP AALSATEIEKSISAR |
| 3 | Cynomolgus BCMA (Predicted NCBI Reference Sequence: XP_00110 6892.1) | | | MLQMARQCSQNEYFDSLLHDCKP CQLRCSSTPPLTCQRYCNASMTNS VKGMNAILWTCLGLSLIISLAVFV LTFLLRKMSSEPLKDEFKNTGSGL LGMANIDLEKGRTGDEIVLPRGLE YTVEECTCEDCIKNKPKVDSDHCF PLPAMEEGATILVTTKTNDYCNSL SAALSVTEIEKSISAR |
| 4 | Murine BCMA (NBCI Reference Sequence: NP_035 738.1) | | | MAQQCFHSEYFDSLLHACKPCHL RCSNPPATCQPYCDPSVTSSVKGT YTVLWIFLGLTLVLSLALFTISFLL RKMNPEALKDEPQSPGQLDGSAQ LDKADTELTRIRAGDDRIFPRSLEY TVEECTCEDCVKSKPKGDSDHFFP LPAMEEGATILVTTKTGDYGKSSV PTALQSVMGMEKPTHTR |
| 5 | 2265-F02 | CDR-H1 | Chothia | GFNISAP |
| 6 | 2265-F02 | CDR-H1 | Kabat | APGIH |
| 7 | 2265-F02 | CDR-H2 | Chothia | NPAGGY |
| 8 | 2265-F02 | CDR-H2 | Kabat | FINPAGGYTDYADSVKG |
| 9 | 2265-F02 | CDR-H3 | | DYIRQYWTYVLDY |
| 10 | trastuzumab | CDR-L1 | | RASQDVNTAVA |
| 11 | trastuzumab | CDR-L2 | | SASFLYS |
| 12 | trastuzumab | CDR-L3 | | QQHYTTPPT |

TABLE 8-continued

Sequences

| SEQ ID NO: | Molecule | Region | Scheme | Sequence |
|---|---|---|---|---|
| 13 | 2265-F02 | V$_H$ | | EVQLVESGGGLVQPGGSLRLSCA ASGFNISAPGIHWVRQAPGKGLE WVGFINPAGGYTDYADSVKGRFTI SADTSKNTAYLQMNSLRAEDTAV YYCARDYIRQYWTYVLDYWGQG TLVTVSS |
| 14 | trastuzumab | V$_L$ | | DIQMTQSPSSLSASVGDRVTITCR ASQDVNTAVAWYQQKPGKAPKLLI YSASFLYSGVPSRFSGSRSGTDFT LTISSLQPEDFATYYCQQHYTTPP TFGQGTKVEIK |
| 15 | Antibody 2265-F02 | Heavy Chain | | EVQLVESGGGLVQPGGSLRLSCA ASGFNISAPGIHWVRQAPGKGLE WVGFINPAGGYTDYADSVKGRFTI SADTSKNTAYLQMNSLRAEDTAV YYCARDYIRQYWTYVLDYWGQGT LVTVSSASTKGPSVFPLAPSSKST SGGTAALGCLVKDYFPEPVTVSW NSGALTSGVHTFPAVLQSSGLYSL SSWTVPSSSLGTQTYICNVNHKPS NTKVDKKVEPKSCDKTHTCPPCPA PELLGGPSVFLFPPKPKDTLMISR TPEVTCVVVDVSHEDPEVKFNWY VDGVEVHNAKTKPREEQYNSTYR VVSVLTVLHQDWLNGKEYKCKVS NKALPAPIEKTISKAKGQPREPQV YTLPPSREEMTKNQVSLTCLVKGF YPSDIAVEWESNGQPENNYKTTPP VLDSDGSFFLYSKLTVDKSRWQQ GNVFSCSVMHEALHNHYTQKSLS LSPGK<br>Residues in bold are replaced with p-azidomethyl-phenylalanine in Antibody 2265-F02. |
| 16 | Antibody 2265-F02 | Heavy Chain | | GAAGTTCAGTTAGTGGAATCAGG CGGCGGTTTAGTTCAACCAGGCG GTTCATTGCGTCTGTCATGCGCG GCTTCCGGTTTCAACATCAGTGC GCCTGGGATCCATTGGGTGCGTC AGGCCCCAGGCAAGGGTCTGGA GTGGGTCGGTTTTATCAATCCTG CTGGCGGTTATACCGACTATGCG GACTCTGTGAAGGGTCGCTTCAC CATTAGCGCGGATACCTCGAAGA ATACGGCGTATTTACAGATGAAT TCCCTGCGTGCAGAGGACACTGC CGTCTACTATTGTGCGCGCGATT ACATTCGGCAGTACTGGACCTAC GTTCTTGACTACTGGGGCCAGGG TACGCTGGTCACCGTGTCGTCGG CGTCAACCAAGGGTCCGTCGGTT TTTCCGCTGGCGCCGTCGTCAAA ATCTACGTCCGGTGGTACCGCCG CTCTGGGTTGCCTGGTTAAAGAC TACTTTCCGGAGCCGGTCACGGT TTCGTGGAACTCTGGTGCCCTGA CTTCTGGCGTCCACACGTTCCCA GCCGTTTTGCAGTCATCCGGTCT GTAGTCGTTGTCCTCTGTGGTCA CGGTGCCGTCATCGTCTCTGGGC ACCCAAACCTATATCTGCAATGT CAACCACAAACCGTCCAATACG AAAGTTGACAAAAAAGTCGAGC CGAAATCTTGCGACAAGACCCAC ACGTGCCCTCCGTGCCCGGCACC GGAACTGCTGGGCGGTCCGTCGG TGTTCCTGTTCCCGCCGAAGCCG AAAGATACTCTGATGATCTCACG |

TABLE 8-continued

Sequences

| SEQ ID NO: | Molecule | Region | Scheme | Sequence |
|---|---|---|---|---|
| | | | | TACCCCGGAAGTCACGTGTGTTG<br>TTGTTGACGTGTCACACGAAGAT<br>CCAGAGGTGAAATTCAATTGGTA<br>TGTGGACGGTGTCGAAGTGCATA<br>ATGCCAAAACCAAACCGCGCGA<br>GGAACAGTACAACTCCACCTACC<br>GCGTCGTGTCGGTGTTGACCGTC<br>CTGCATCAAGACTGGCTGAACGG<br>TAAAGAGTACAAGTGCAAGGTTT<br>CAAATAAGGCACTGCCTGCGCCG<br>ATTGAAAAGACCATCTCTAAGGC<br>AAAGGGCCAGCCGCGTGAGCCA<br>CAGGTGTATACCCTGCCGCCGTC<br>GCGTGAAGAAATGACCAAGAAC<br>CAAGTTTCACTGACGTGTCTGGT<br>CAAGGGCTTTTATCCGTCCGATA<br>TTGCGGTGGAGTGGGAGTCTAAT<br>GGCCAGCCGGAAAACAATTACA<br>AAACGACTCCGCCGGTGCTGGAT<br>TCCGACGGTTCGTAGTTCCTGTA<br>TTCCAAGCTGACCGTTGACAAAT<br>CACGTTGGCAGCAAGGCAACGTT<br>TTTTCTTGTTCGGTAATGCACGA<br>AGCGCTGCACAATCATTACACCC<br>AGAAATCACTGTCGTTGTCTCCG<br>GGCAAA |
| 17 | Antibody 2265-F02 | Light Chain | | DIQMTQSPSSLSASVGDRVTITCR<br>ASQDVNTAVAWYQQKPGKAPKLLI<br>YSASFLYSGVPSRFSGSRSGTDFTL<br>TISSLQPEDFATYYCQQHYTTPPTF<br>GQGTKVEIKRTVAAPSVFIFPPSDE<br>QLKSGTASVVCLLNNFYPREAKV<br>QWKVDNALQSGNSQESVTEQDSK<br>DSTYSLSSTLTLSKADYEKHKVYA<br>CEVTHQGLSSPVTKSFNRGEC |
| 18 | Antibody 2265-F02 | Light Chain | | GACATTCAAATGACCCAGTCTCC<br>GTCGTCACTGTCCGCATCCGTTG<br>GCGACCGCGTTACCATCACGTGC<br>CGTGCGTCGCAAGATGTGAACAC<br>CGCCGTGGCGTGGTATCAGCAAA<br>AACCGGGCAAAGCTCCGAAGCT<br>GCTGATCTATTCAGCCTCTTTCCT<br>GTACTCGGGTGTTCCGTCCCGTT<br>TCTCAGGCTCTCGCTCGGGTACG<br>GATTTCACCCTGACTATTTCTTCA<br>CTGCAACCGGAAGATTTTGCGAC<br>GTACTACTGTCAGCAGCATTACA<br>CGACTCCGCCGACCTTTGGTCAG<br>GGTACCAAGGTCGAGATTAAGC<br>GTACCGTGGCTGCACCATCCGTG<br>TTTATCTTCCCTCCGTCTGATGAG<br>CAGCTGAAATCCGGTACGGCGTC<br>GGTCGTCTGCTTGCTGAATAACT<br>TCTATCCGCGTGAAGCGAAGGTG<br>CAATGGAAGGTTGACAATGCCCT<br>GCAGTCAGGTAACTCCCAAGAGT<br>CTGTTACCGAACAAGATTCGAAA<br>GACTCAACCTACTCCCTGTCTTC<br>GACGCTGACGTTGTCCAAAGCGG<br>ACTATGAGAAACACAAGGTTTAC<br>GCATGTGAAGTGACCCACCAGG<br>GCCTGTCATCTCCGGTCACCAAA<br>TCATTTAATCGCGGTGAGTGC |
| 19 | Human IGg1 HC Constant | | | ASTKGPSVFPLAPSSKSTSGGTAAL<br>GCLVKDYFPEPVTVSWNSGALTS<br>GVHTFPAVLQSSGLYSLSSVVTVP<br>SSSLGTQTYICNVNHKPSNTKVDK<br>KVEPKSCDKTHTCPPCPAPELLGG<br>PSVFLFPPKPKDTLMISRTPEVTC<br>VVVDVSHEDPEVKFNWYVDGVEV<br>HNAKTKPREEQYNSTYRVVSVLT |

TABLE 8-continued

Sequences

| SEQ ID NO: | Molecule | Region | Scheme | Sequence |
|---|---|---|---|---|
| | | | | VLHQDWLNGKEYKCKVSNKALPA PIEKTISKAKGQPREPQVYTLPPS REEMTKNQVSLTCLVKGFYPSDIA VEWESNGQPENNYKTTPPVLDSD GSFFLYSKLTVDKSRWQQGNVFS CSVMHEALHNHYTQKSLSLSPGK |
| 20 | Human IgG LC Constant Ckappa | | | RTVAAPSVFIFPPSDEQLKSGTASV VCLLNNFYPREAKVQWKVDNAL QSGNSQESVTEQDSKDSTYSLSST LTLSKADYEKHKVYACEVTHQGL SSPVTKSFNRGEC |
| 21 | Mouse IGg1 HC Constant | | | AKTTPPSVYPLAPGSAAQTNSMVT LGCLVKGYFPEPVTVTWNSGSLSS GVHTFPAVLQSDLYTLSSSVTVPS STWPSETVTCNVAHPASSTKVDKK IVPRDCGCKPCICTVPEVSSVFIFP PKPKDVLTITLTPKVTCVVVDISK DDPEVQFSWFVDDVEVHTAQTQP REEQFNSTFRSVSELPIMHQDWLN GKEFKCRVNSAAFPAPIEKTISKTK GRPKAPQVYTIPPPKEQMAKDKVS LTCMITDFFPEDITVEWQWNGQPA ENYKNTQPIMDTDGSYFVYSKLN VQKSNWEAGNTFTCSVLHEGLHN HHTEKSLSHSPG |
| 22 | Mouse IgG LC Constant Ckappa | | | RADAAPTVS1FPPSSEQLTSGGASV VCFLNNFYPKDINVKWKIDGSERQ NGVLNSWTDQDSKDSTYSMSSTL TLTKDEYERHNSYTCEATHKTSTS PIVKSFNRNEC |
| 23 | Kappa LC | | | HMTVAAPSVFIFPPSDEQLKSGTA SVVCLLNNFYPREAKVQWKVDN ALQSGNSQESVTEQDSKDSTYSLS STLTLSKADYEKHKVYACEVTHQ GLSSPVTKSFNRGEC |
| 24 | Lambda LD | | | GQPKAAPSVTLFPPSSEELQANKA TLVCLISDFYPGAVTVAWKADSSP VKAGVETTTPSKQSNNKYAASSY LSLTPEQWKSHRSYSCQVTHEGST VEKTVAPTECS |
| 25 | FlagHis Tag | | | GSGDYKDDDDKGSGHHHHHH |
| 26 | Linker | | | GGGGSGGGGSGGGGS |
| 27 | Linker | | | AAGSDQEPKSS |

Example 8

An Open-Label, Phase 1, Dose Escalation (Part A) and Clinical Expansion (Part B) First-In-Human (FIH) Clinical Study of Conjugate 4 in Monotherapy or in Combination with in Subjects with Relapsed and Refractory Multiple Myeloma (MM)

This Example outlines a Phase 1, Multicenter, Open-label, Dose Finding Study of Conjugate 4, a BCMA Antibody-Drug Conjugate, in Subjects with Relapsed and Refractory Multiple Myeloma (MM). In particular, the Phase 1 study is a dose escalation (Part A) and expansion (Part B), first-in-human (FIH) clinical study of Conjugate 4 monotherapy and in combination with BMS-986405 (a gamma secretase inhibitor (GSI)) in subjects with relapsed and refractory MM. The primary objectives of this study are (1) to determine the safety and tolerability of Conjugate 4 monotherapy and in combination with BMS-986405 in subjects with relapsed and refractory MM and (2) to define the maximum tolerated dose (MTD) and/or the recommended Phase 2 dose (RP2D) of Conjugate 4 monotherapy and in combination with BMS-986405 in subjects with relapsed and refractory MM. The secondary objectives of this study are (1) to evaluate the preliminary efficacy of Conjugate 4 monotherapy and in combination with BMS-986405 in relapsed and refractory MM, (2) to characterize the pharmacokinetics (PK) of Conjugate 4 in monotherapy and of Conjugate 4 and BMS-986405 in combination, and (3) to determine the presence, frequency, and functional impact of Conjugate 4 anti-drug antibodies (ADAs).

Inclusion criteria. Subjects may satisfy the following criteria to be enrolled in the study: (1) the subject (male or female) is ≥18 years of age at the time of signing the ICF;

(2) the subject has a history of MM with relapsed and refractory disease, and: (a) may have disease that is nonresponsive while on their last antimyeloma therapy (failure to obtain a minimal response (MR) or better) or documented disease progression on or within 60 days from the last dose of their last antimyeloma therapy and, (b) may have received at least 3 prior MM treatment regimens, wherein each regimen may have at least 2 consecutive cycles of treatment unless progressive disease (PD) was the best response to the regimen (Note: induction with or without hematopoietic stem cell transplant and with or without maintenance therapy is considered a single regimen) and, (c) may have received a proteasome inhibitor, an immunomodulatory agent and an anti-CD38 antibody (e.g., daratumumab) and, (d) should have failed treatment with or are intolerant to all established therapies known to provide clinical benefit in relapsed and refractory MM; (3) subjects may have measurable disease, including at least one of the criteria as follows: (a) M-protein quantities ≥0.5 g/dL by serum protein electrophoresis (sPEP) or, (b) ≥200 mg/24 hours urine collection by urine protein electrophoresis (uPEP) or, (c) serum FLC levels >100 mg/L (milligrams/liter involved light chain) and an abnormal kappa/lambda (κ/λ) ratio in patients without detectable serum or urine M-protein or, (d) for subjects with immunoglobulin class A (IgA) myeloma whose disease can only be reliably measured by quantitative immunoglobulin measurement, a serum monoclonal IgA level ≥0.50 g/dL; (4) the subject consents to serial bone marrow aspirations and/or biopsies; (5) the subject has an ECOG PS of 0-1; (6) the subjects may have the following laboratory values: (a) Absolute neutrophil count (ANC) ≥1.0×10$^9$/L without growth factor support for 7 days (14 days ifpegfilgrastim), (b) Platelets (plt)≥75×10$^9$/L without transfusion for 7 days or plt ≥50×10$^9$/L when BM plasma cells ≥50%, (c) Potassium within normal limits or correctable with supplements, (d) Aspartate aminotransferase (AST/SGOT) and alanine aminotransferase (ALT/SGPT) ≤2.5× upper limit of normal (ULN), (e) Serum bilirubin ≤1.5×ULN (or ≤2.0×ULN for subjects with documented Gilbert's syndrome), (f) Estimated serum creatinine clearance of ≥60 mL/min using the Cockcroft-Gault equation or directly calculated from the 24-hour urine collection method, (g) International normalized ratio (INR)<1.5×ULN and activated partial thromboplastin time (APTT)<1.5× ULN; (7) Females of childbearing potential (FCBP) (a female of childbearing potential is a sexually mature woman who 1) has not undergone a hysterectomy (the surgical removal of the uterus) or bilateral oophorectomy (the surgical removal of both ovaries) or 2) has not been naturally postmenopausal for at least 24 consecutive months (e.g., has had menses at any time during the preceding 24 consecutive months)) may: (a) either commit to true abstinence (true abstinence is acceptable when this is in line with the preferred and usual lifestyle of the subject. [note: periodic abstinence (e.g., calendar, ovulation, symptothermal, post-ovulation methods) and withdrawal are not acceptable methods of contraception]) from heterosexual contact (which may be reviewed on a monthly basis and source documented) or agree to use, and be able to comply with, at least two effective contraceptive methods (oral, injectable, or implantable hormonal contraceptive; tubal ligation; intrauterine device; barrier contraceptive with spermicide; or vasectomized partner), one of which may be barrier, from signing the ICF, throughout the study, and for up to 42 days following the last dose of Conjugate 4; and (b) have two negative pregnancy tests prior to starting Conjugate 4. She may agree to ongoing pregnancy testing during the course of the study, and after end of study treatment. This applies even if the subject practices true abstinence from heterosexual contact. The subject may not receive IP until it is verified that the result of the pregnancy test is negative, as follows: (i) a negative serum pregnancy test (sensitivity of at least 25 mIU/mL) at Screening, (ii) a negative serum or urine pregnancy test within 72 hours prior to Cycle 1 Day −1 of study treatment, and within 72 hours prior to Day −1 of every subsequent cycle (note that the Screening serum pregnancy test can be used as the test prior to Day −1 study treatment if it is performed within the prior 72 hours). A serum or urine pregnancy test may also be performed at the end of study for each female of childbearing potential (FCBP); (c) Avoid conceiving for 42 days after the last dose of Conjugate 4 and, in Arm 2, for 3 months after the last dose of BMS-986405, (d) Agree to ongoing pregnancy testing during the course of the study, and after the end of study treatment. This applies even if the subject practices true abstinence from heterosexual contact; (8) Males may practice true abstinence (which may be reviewed on a monthly basis) or agree to use a condom (a latex condom is recommended) during sexual contact with a pregnant female or a FCBP and avoids conceiving from signing the ICF, while participating in the study, during dose interruptions, and for at least 42 days following Conjugate 4 discontinuation and, in Arm 2, for 3 months after the last dose of BMS-986405, even if he has undergone a successful vasectomy; (9) Subject is willing and able to adhere to the study visit schedule and other protocol requirements.

Figure 2:
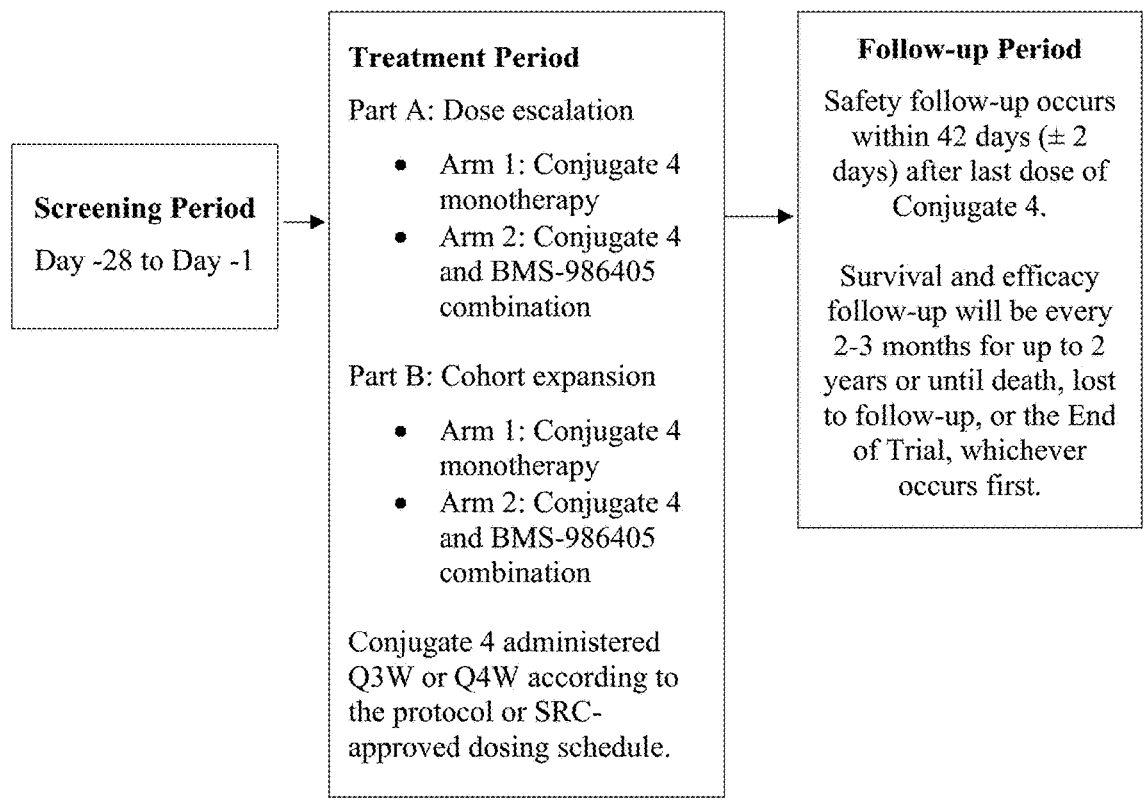
FIG. 2 illustrates the overall study design of a Phase 1, Multicenter, Open-label, Dose Finding Study of Conjugate 4, a BCMA Antibody-Drug Conjugate, in Subjects with Relapsed and Refractory Multiple Myeloma. In particular, the Phase 1 study is a dose escalation (Part A) and cohort expansion (Part B), first-in-human (FIH) clinical study of Conjugate 4 monotherapy and in combination with BMS-986405 (a gamma secretase inhibitor (GSI)) in subjects with relapsed and refractory MM.

Study Design. The dose escalation part (Part A) of the study evaluates the safety and tolerability of escalating doses of Conjugate 4, administered IV, in monotherapy (Arm 1) or in combination with BMS-986405 (Arm 2) to determine the maximum tolerated dose (MTD) of Conjugate 4 guided by a Bayesian logistic regression model (BLRM). A modified accelerated titration design is used for Arm 1 and Arm 2. The MTD may be established separately for Conjugate 4 administered Q3W (once every three weeks) and Q4W (once every four weeks). The expansion part (Part B) further evaluates the safety and efficacy of Conjugate 4 in monotherapy (Arm 1) or combination (Arm 2) administered at or below the MTD in selected expansion cohorts of approximately 80 evaluable subjects in order to determine the Recommended Phase 2 dose (RP2D). One or more doses and dosing regimens may be selected for cohort expansion to determine RP2D based on the totality of Conjugate 4 data such as nonclinical data, PK, PD, safety, and efficacy data. All subjects are treated until confirmed disease progression per IMWG criteria, unacceptable toxicity, or subject/Investigator decision to withdraw. Parts A and B consist of 3 periods: Screening, Treatment, and Follow-up. The overall study design is shown in FIG. 2.

Method of Treatment. In Part A Arm 1, the starting dose (Cohort 1) of Conjugate 4 is 0.6 mg/kg per subject. Following the first dose in Cohort 1, subsequent doses are given Q3W. If the starting dose of Conjugate 4 is not tolerated, a lower dose level (i.e., Cohort −1, 0.3 mg/kg) or alternate dosing interval (ie, Q4W) may be explored. The initial 2 dose escalation increments is approximately 2-fold; above the 2.0 mg/kg dose level, the dose increase is no more than 50%. The initial two Conjugate 4 infusions are administered over at least 60 minutes. In the absence of significant IRRs or hypersensitivity during the previous infusion, subsequent infusions can be administered over 30 minutes.

Dosing cohorts for the Arm 1 dose escalation are summarized in Table 9.

TABLE 9

Part A (Dose Escalation): Dose Levels of
Conjugate 4 Monotherapy (Arm 1)

| Cohort | Dose (mg/kg) |
| --- | --- |
| −1 | 0.3 |
| 1 | 0.6 |
| 2 | 1.25 |
| 3 | 2.0 |
| 4 | 3.0 |
| 5 | 4.5 |
| 6 | 6.7 |
| 7 | 10.0 |

In Part A Arm 2, the starting dose of Conjugate 4 is 0.6 mg/kg per subject and BMS-986405 dose is fixed at 25 mg TIW (i.e., for three times a week). In particular, BMS-986405 dose is administrated orally TIW every week during a 21-day cycle (e.g., Day 1, Day 3, Day 5, Day 8, Day 10, Day 12, Day 15, Day 17, and Day 19), with 48 hours between each dose within a week (±12 hours). Following the first dose of Conjugate 4 in the first Arm 2 cohort, subsequent doses of Conjugate 4 are given Q3W. If the starting dose of Conjugate 4 is not tolerated in Arm 2, a lower Conjugate 4 dose level/or alternate dosing interval of Conjugate 4 (e.g., Q4W) may be explored. In Arm 2 cohorts, the initial 2 dose escalation increments are approximately 2-fold; above the 2.0 mg/kg dose level, the dose increase is no more than 50%. Dosing cohorts for the Arm 2 dose escalation are summarized in Table 10.

TABLE 10

Part A (Dose Escalation): Dose Levels of Conjugate
4 Combination Therapy (Arm 2)

| Cohort | Conjugate 4 Dose (mg/kg) | BMS-986405 Dose (mg) TIW |
| --- | --- | --- |
| −1 | 0.3 | 25 |
| 1 | 0.6 | 25 |
| 2 | 1.25 | 25 |
| 3 | 2.0 | 25 |
| 4 | 3.0 | 25 |
| 5 | 4.5 | 25 |
| 6 | 6.7 | 25 |

During dose escalation, the decision to evaluate additional subjects within a dose cohort, the next higher dose level, intermediate dose levels, or declare an MTD is determined by the safety review committee (SRC), based on the Bayesian logistic regression model (BLRM, described below) recommendation, clinical and laboratory safety data (both DLT and non-DLT safety data), PK, and PD for a given dose level. The SRC may recommend to test one or more parallel dose escalation cohorts using different schedules (eg, Q4W). If an alternate dosing interval is explored, the starting dose for that cohort is at or below a dose level that was determined to be tolerated. Additionally, the SRC may recommend to split the dose escalation into two or more parallel escalation cohorts based on subject-specific variables such as baseline myeloma tumor burden (e.g., by percentage of bone marrow plasma cells, BCMA expression, or other variables).

Following completion of dose escalation (Part A), selected cohorts of subjects with relapsed and refractory MM may be enrolled into an expansion phase (Part B). Expansion uses the dose and schedule established in the dose escalation phase based on review of safety, PK, and PD data from Part A. One or more doses and dosing regimens may be explored in cohort expansion in order to determine RP2D. The SRC selects the dose, schedule, treatment regimens, and/or relapsed and refractory MM subject populations of interest for cohort expansion.

Endpoints. Response is assessed by the investigators using the International Myeloma Working Group (IMWG) Uniform Response Criteria (Kumar, S. et al., "International Myeloma Working Group consensus criteria for response and minimal residual disease assessment in multiple myeloma," *Lancet Oncol.*, 2016; 17(8):e328-46) at Day 1 of every cycle (starting on Cycle 2 Day 1) and at the end of treatment (EOT).

Key efficacy assessments include the following: Myeloma paraprotein (M-protein) in serum and 24-hour urine collections; serum immunoglobulins; serum free light chains; corrected serum calcium; percent of plasma cells in the bone marrow; radiographic assessments of lytic bone lesions; extramedullary plasmacytoma (EMP) assessments; and minimal residual disease (MRD) evaluation by EuroFlow and/or next-generation sequencing (NGS) if sample is evaluable.

Other efficacy variables to be analyzed include overall response rate (ORR), time to response, duration of response (DOR), progression-free survival (PFS), and overall survival (OS).

The efficacy variable of primary interest is myeloma response, including minimal response (MR) and progressive disease according to the IMWG criteria (Kumar, S. et al., 2016 (see above)). Additional variables are summarized including time to response: time from the start of treatment to the first documentation of response (partial response (PR) or better), and duration of response: time from the first documentation of response (PR or better) to the first documentation of progressive disease. Progression-free survival and OS is analyzed in addition to the previous list of endpoints. Efficacy variables are summarized using frequency tabulations for categorical variables or descriptive statistics for time to event endpoints and continuous variables.

Overall Response Rate (ORR). The overall response rate is defined as the proportion of subjects who achieve a partial response or better (e.g., PR, very good partial response (VGPR), complete response (CR) or stringent complete response (sCR)), according to IMWG response criteria. Analysis of ORR is based on safety population and efficacy evaluable population. The number and percentage of subjects in the following response categories is presented: stringent complete response (sCR), complete response (CR), sCR+CR, very good partial response (VGPR), partial response (PR), overall response (sCR+CR+VGPR+PR), minimal response (MR), overall response+MR (sCR, CR, VGPR, PR, and MR), stable disease (SD), progressive disease (PD), and not evaluable (NE). The corresponding 90% exact CI for each response category is also provided.

Minimal residual disease (MRD) negative rate is defined as the proportion of subjects who have negative MRD at any timepoint after the first dose. MRD negative rates as assessed by different methods including sustained MRD-negative, flow MRD-negative, sequencing MRD-negative, and imaging plus MRD-negative are reported based on the safety population. The corresponding 90% exact CI is provided.

Time to Response. Time to response is defined as the time from the first study treatment dose date to the date of first documented response (PR or better). This analysis is confined to subjects who have responded. Time to response is summarized using descriptive statistics (mean, standard deviation, median, minimum and maximum) for the safety population.

Duration of Response. Duration of response is defined as the time from the earliest date of documented response (≥PR) to the first documented disease progression or death, whichever occurs first. Duration of response is summarized using Kaplan-Meier estimates. The analysis population is confined to those who have responded. Subjects who neither progress nor die by a data cutoff date are censored at the date of their last adequate tumor assessment. The duration of response is also summarized using descriptive statistics (mean, standard deviation, median, minimum and maximum). Except for the median, which is calculated based on both observed and censored values using the Kaplan-Meier method, all other statistics (mean, standard deviation, minimum and maximum) are calculated based on observed values only.

Progression free Survival. Progression-free survival is defined as the time from the first dose of a study treatment to PD or death from any cause, whichever occurs first. Subjects who neither progress nor die by a data cut-off date are censored at the date of their last adequate tumor assessment. The PFS is summarized using the Kaplan-Meier method for the safety population.

Overall Survival. Overall survival is defined as the time from the first dose of a study treatment to death from any cause. Subjects who are still alive at the clinical cut-off date for the analysis are censored at the last known alive date. The OS is summarized using the Kaplan-Meier method for the safety population.

Table 11 provides study endpoints, including primary, secondary, and exploratory endpoints.

TABLE 11

Study Endpoints.

| Endpoint | Name | Description | Timeframe |
|---|---|---|---|
| Primary | Safety | DLTs and MTD during the DLT evaluation period; AEs evaluated using the NCI CTCAE criteria, Version 5.0 | Dose escalation and dose expansion |
| Secondary | Preliminary efficacy | Determined by IMWG criteria including: ORR Time to response Duration of response PFS OS | Dose escalation and dose expansion |
| | PK endpoints | $C_{max}$, $C_{min}$, Area under the curve (AUC), $t_{max}$, $t_{1/2}$, CL, $V_{ss}$, and accumulation index of Conjugate 4 (total antibody and ADC) and SC-246 (a catabolite consisting of a maytansinoid warhead-linker-non-natural amino acid, pAMF), which is a component of Conjugate 4, in Arm 1 and Arm 2; BMS-986405 in Arm 2, as appropriate. | Dose escalation and dose expansion |
| | ADA endpoints | Presence and frequency of Conjugate 4 ADA using a validated bridging immunoassay with electrochemiluminescence detection | Dose escalation and dose expansion |
| Exploratory | PD endpoints | Evaluate measures of tumor sensitivity/resistance to Conjugate 4 by measuring depletion of BM plasma cells during treatment by Next-generation flow cytometry (NGF). | Dose escalation and dose expansion |
| | Preliminary efficacy | Evaluate the level of MRD by NGF and/or Next-generation sequencing (NGS). | Dose escalation and dose expansion |
| | Biomarker | Evaluate the percentage of BCMA+ plasma cells and quantitate the level of surface BCMA expression in the bone marrow at baseline by flow cytometry and immunohistochemistry (IHC). | Dose escalation and dose expansion |
| | Biomarker | Evaluate mechanism of action and potential resistance by measuring malignant plasma cell proliferation by flow cytometry and IHC, loss of BCMA target expression, gene signatures by RNAseq, and molecular profiling of tumor cells by NGS. | Dose escalation and dose expansion |
| | PD endpoint | Evaluate levels of circulating sBCMA, APRIL, and BAFF as a surrogate of tumor cell depletion. Evaluate levels of sBCMA as a measure of BMS-986405 activity. | Dose escalation and dose expansion |

TABLE 11-continued

Study Endpoints.

| Endpoint | Name | Description | Timeframe |
|---|---|---|---|
| | Biomarker | Exploratory measurements of SARS-CoV-2 serology (anti-SARS-CoV-2 total or IgG) from serum samples collected at baseline and specified timepoints. | Dose escalation and dose expansion |

ADA = anti-Conjugate 4 antibodies;
AE = adverse event;
APRIL = a proliferation inducing ligand;
AUC = area under the serum concentration time-curve;
CL = total body clearance of the drug from the serum;
BAFF = B cell-activating factor;
BCMA = B cell maturation antigen;
BM = bone marrow;
$C_{max}$ = maximum serum concentration of drug;
$C_{min}$ = minimum serum concentration of drug;
DLT = dose-limiting toxicity;
IHC = immunohistochemistry;
IMWG = International Myeloma Working Group;
MRD = minimal residual disease;
MTD = maximum tolerated dose;
NCI CTCAE = National Cancer Institute common terminology criteria for adverse events;
NGF = next generation flow cytometry;
NGS = next generation sequencing;
ORR = overall response rate;
OS = overall survival;
PD = pharmacodynamic;
PFS = progression free survival;
PK = pharmacokinetic;
RNASeq = ribonucleic acid sequencing;
sBCMA = soluble B cell maturation antigen;
$t_{1/2}$ = terminal half-life;
$t_{max}$ = time to peak (maximum) serum concentration;
$V_{ss}$ = volume of distribution at steady-state.

Example 9

An Open-Label, Phase 1, Dose Escalation (Part A) and Clinical Expansion (Part B) First-In-Human (FIH) Clinical Study of Conjugate 4 in Monotherapy or in Combination with in Subjects with Relapsed and Refractory Multiple Myeloma (MM)

This example outlines a Phase 1, Multicenter, Open-label, Dose Finding Study of Conjugate 4, a BCMA Antibody-Drug Conjugate, in Subjects with Relapsed and Refractory Multiple Myeloma (MM). In particular, the Phase 1 study is a dose escalation (Part A) and expansion (Part B), first-in-human (FIH) clinical study of Conjugate 4 monotherapy and in combination with BMS-986405 (a gamma secretase inhibitor (GSI)) in subjects with relapsed and refractory MM. The primary objectives of this study are (1) to determine the safety and tolerability of Conjugate 4 monotherapy and in combination with BMS-986405 in subjects with relapsed and refractory MM and (2) to define the maximum tolerated dose (MTD) and/or the recommended Phase 2 dose (RP2D) of Conjugate 4 monotherapy and in combination with BMS-986405 in subjects with relapsed and refractory MM. The secondary objectives of this study are (1) to evaluate the preliminary efficacy of Conjugate 4 monotherapy and in combination with BMS-986405 in relapsed and refractory MM, (2) to characterize the pharmacokinetics (PK) of Conjugate 4 in monotherapy and of Conjugate 4 and BMS-986405 in combination, and (3) to determine the presence, frequency, and functional impact of Conjugate 4 anti-drug antibodies (ADAs).

Inclusion criteria. Subjects may satisfy the following criteria to be enrolled in the study: (1) the subject (male or female) is ≥18 years of age at the time of signing the ICF; (2) the subject has a history of MM with relapsed and refractory disease, and may: (a) have disease that is nonresponsive while on their last antimyeloma therapy (failure to obtain a minimal response (MR) or better) or documented disease progression on or within 60 days from the last dose of their last antimyeloma therapy (Note: subjects with documented disease progression who received chimeric antigen receptor [CAR] T cells as their last myeloma therapy are permitted to enroll with disease that is nonresponsive (failure to obtain a MR or better) or documented disease progression beyond 60 days from CAR T infusion) and (b) have received at least 3 prior MM treatment regimens (Note: induction with or without hematopoietic stem cell transplant and with or without maintenance therapy is considered a single regimen) Subjects have previously received each of the following therapies: (i) A regimen that included an immunomodulatory agent (e.g., lenalidomide, pomalidomide) and a proteasome inhibitor (e.g., bortezomib, carfilzomib, ixazomib), alone or in combination. Subjects may have undergone at least 2 complete cycles of treatment unless progressive disease was the best response to the regimen; (ii) a regimen that included anti-CD38 (e.g., daratumumab) monotherapy or as part of a combination regimen; and (iii) autologous stem cell transplant, unless the subject was ineligible; (3) subjects may have measurable disease, including at least one of the criteria as follows: (a) M-protein quantities ≥0.5 g/dL by serum protein electrophoresis (sPEP) or, (b) ≥200 mg/24 hours urine collection by urine protein electrophoresis (uPEP) or, (c) serum FLC levels >100 mg/L (milligrams/liter involved light chain) and an abnormal kappa/lambda (κ/λ) ratio in patients without detectable serum or urine M-protein or, (d) for subjects with immunoglobulin class A (IgA) myeloma whose disease can only be reliably measured by quantitative immunoglobulin measurement, a serum monoclonal IgA level >0.50 g/dL; (4) the subject consents to serial bone marrow aspirations and/or biopsies; (5) the subject has an ECOG PS of 0-1; (6) the subjects may have the following laboratory values: (a) Absolute neutrophil count (ANC)≥1.0×10$^9$/L without growth factor support for 7 days (14 days if pegfilgrastim), (b) Platelets (plt)≥75×10$^9$/L without transfusion for 7 days or plt ≥50×10$^9$/L when BM plasma cells ≥50%, (c) Potassium within normal limits or correctable with supplements, (d) Aspartate aminotransferase (AST/SGOT) and alanine aminotransferase (ALT/SGPT)≤2.5× upper limit of normal (ULN), (e) Serum bilirubin ≤1.5×ULN (or ≤2.0×ULN for subjects with documented Gilbert's syndrome), (f) Estimated serum creatinine clearance of ≥60 mL/min using the Cockcroft-Gault equation or directly calculated from the 24-hour urine collection method, (g) International normalized ratio (INR)<1.5×ULN and activated partial thromboplastin time (APTT)<1.5×ULN; (7) Females of childbearing potential (FCBP) (a female of childbearing potential is a sexually mature woman who 1) has not undergone a hysterectomy (the surgical removal of the uterus) or bilateral oophorectomy (the surgical removal of both ovaries) or 2) has not been naturally postmenopausal for at least 24 consecutive months (e.g., has had menses at any time during the preceding 24 consecutive months)) may: (a) either commit to true abstinence (true abstinence is acceptable when this is in line with the preferred and usual lifestyle of the subject. [note: periodic abstinence (e.g., calendar, ovulation, symptothermal, post-ovulation methods) and withdrawal are not acceptable methods of contraception]) from heterosexual contact (which may be reviewed on a monthly basis and source documented) or agree to use, and be able to comply with, at least two effective contraceptive methods (oral, injectable, or implantable hormonal contraceptive; tubal ligation; intra-uterine device; barrier contraceptive with spermicide; or vasectomized partner), one of which may be barrier, from signing the ICF, throughout the study, and for up to 42 days following the last dose of Conjugate 4; and (b) have two negative pregnancy tests prior to starting Conjugate 4. She may agree to ongoing pregnancy testing during the course of the study, and after end of study treatment. This applies even if the subject practices true abstinence from heterosexual contact. The subject may not receive IP until it is verified that the result of the pregnancy test is negative, as follows: (i) a negative serum pregnancy test (sensitivity of at least 25 mIU/mL) at Screening, (ii) a negative serum or urine pregnancy test within 72 hours prior to Cycle 1 Day −1 of study treatment, and within 72 hours prior to Day −1 of every subsequent cycle (note that the Screening serum pregnancy test can be used as the test prior to Day −1 study treatment if it is performed within the prior 72 hours). A serum or urine pregnancy test may also be performed at the end of study for each female of childbearing potential (FCBP); (c) Avoid conceiving for 42 days after the last dose of Conjugate 4 and, in Arm 2, for 3 months after the last dose of BMS-986405, (d) Agree to ongoing pregnancy testing during the course of the study, and after the end of study treatment. This applies even if the subject practices true abstinence from heterosexual contact; (8) Males may practice true abstinence (which may be reviewed on a monthly basis) or agree to use a condom (a latex condom is recommended) during sexual contact with a pregnant female or a FCBP and avoids conceiving from signing the ICF, while participating in the study, during dose interruptions, and for at least 42 days following Conjugate 4 discontinuation and, in Arm 2, for 3 months after the last dose of BMS-986405, even if he has undergone a successful vasectomy; (9) Subject is willing and able to adhere to the study visit schedule and other protocol requirements.

Study Design. The dose escalation part (Part A) of the study evaluates the safety and tolerability of escalating doses of Conjugate 4, administered IV, in monotherapy (Arm 1) or in combination with BMS-986405 (Arm 2) to determine the maximum tolerated dose (MTD) of Conjugate 4 guided by a Bayesian logistic regression model (BLRM). A modified accelerated titration design is used for Arm 1 and Arm 2. The MTD may be established separately for Conjugate 4 administered Q3W and Q4W. The expansion part (Part B) further evaluates the safety and efficacy of Conjugate 4 in monotherapy (Arm 1) or combination (Arm 2) administered at or below the MTD in selected expansion cohorts of approximately 80 evaluable subjects in order to determine the Recommended Phase 2 dose (RP2D). One or more doses and dosing regimens may be selected for cohort expansion to determine RP2D based on the totality of Conjugate 4 data such as nonclinical data, PK, PD, safety, and efficacy data. All subjects are treated until confirmed disease progression per IMWG criteria, unacceptable toxicity, or subject/Investigator decision to withdraw. Parts A and B consist of 3 periods: Screening, Treatment, and Follow-up. The overall study design is shown in FIG. 2.

Method of Treatment. In Part A Arm 1, the starting dose (Cohort 1) of Conjugate 4 is 0.6 mg/kg per subject. Following the first dose in Cohort 1, subsequent doses are given Q3W. If the starting dose of Conjugate 4 is not tolerated, a lower dose level (i.e., Cohort −1, 0.3 mg/kg) or alternate dosing interval (ie, Q4W) may be explored. The initial 2 dose escalation increments is approximately 2-fold; above the 2.0 mg/kg dose level, the dose increase is no more than 50%. The initial two Conjugate 4 infusions are administered over at least 60 minutes. In the absence of significant IRRs or hypersensitivity during the previous infusion, subsequent infusions can be administered over 30 minutes.

Dosing cohorts for the Arm 1 dose escalation are summarized in Table 12.

TABLE 12

Part A (Dose Escalation): Dose Levels of Conjugate 4 Monotherapy (Arm 1)

| Cohort | Dose (mg/kg) |
|---|---|
| −1 | 0.3 |
| 1 | 0.6 |
| 2 | 1.25 |
| 3 | 2.0 |
| 4 | 3.0 |
| 5 | 4.5 |
| 6 | 6.7 |
| 7 | 10.0 |

In Part A Arm 2, the starting dose of Conjugate 4 is 0.6 mg/kg per subject and BMS-986405 dose is fixed at 25 mg TIW (i.e., for three times a week). In particular, BMS-986405 dose is administrated orally TIW every week during a 21-day cycle (e.g., Day 1, Day 3, Day 5, Day 8, Day 10, Day 12, Day 15, Day 17, and Day 19), with 48 hours between each dose within a week (±12 hours). Following the first dose of Conjugate 4 in the first Arm 2 cohort, subsequent doses of Conjugate 4 are given Q3W. If the starting dose of Conjugate 4 is not tolerated in Arm 2, a lower Conjugate 4 dose level/or alternate dosing interval of Conjugate 4 (e.g., Q4W) may be explored. In Arm 2 cohorts, the initial 2 dose escalation increments are approximately 2-fold; above the 2.0 mg/kg dose level, the dose increase is no more than 50%. Dosing cohorts for the Arm 2 dose escalation are summarized in Table 13.

TABLE 13

Part A (Dose Escalation): Dose Levels of Conjugate 4 Combination Therapy (Arm 2)

| Cohort | Conjugate 4 Dose (mg/kg) | BMS-986405 Dose (mg) TIW |
|---|---|---|
| −1 | 0.3 | 25 |
| 1 | 0.6 | 25 |
| 2 | 1.25 | 25 |
| 3 | 2.0 | 25 |
| 4 | 3.0 | 25 |
| 5 | 4.5 | 25 |
| 6 | 6.7 | 25 |

During dose escalation, the decision to evaluate additional subjects within a dose cohort, the next higher dose level, intermediate dose levels, or declare an MTD is determined by the safety review committee (SRC), based on the Bayesian logistic regression model (BLRM, described below) recommendation, clinical and laboratory safety data (both DLT and non-DLT safety data), PK, and PD for a given dose level. The SRC may recommend to test one or more parallel dose escalation cohorts using different schedules (eg, Q4W). If an alternate dosing interval is explored, the starting dose for that cohort is at or below a dose level that was determined to be tolerated. Additionally, the SRC may recommend to split the dose escalation into two or more parallel escalation cohorts based on subject-specific variables such as baseline myeloma tumor burden (e.g., by percentage of bone marrow plasma cells, BCMA expression, or other variables).

Following completion of dose escalation (Part A), selected cohorts of subjects with relapsed and refractory MM may be enrolled into an expansion phase (Part B). Expansion uses the dose and schedule established in the dose escalation phase based on review of safety, PK, and PD data from Part A. One or more doses and dosing regimens may be explored in cohort expansion in order to determine RP2D. The SRC selects the dose, schedule, treatment regimens, and/or relapsed and refractory MM subject populations of interest for cohort expansion.

Endpoints. Response is assessed by the investigators using the International Myeloma Working Group (IMWG) Uniform Response Criteria (Kumar, S. et al., "International Myeloma Working Group consensus criteria for response and minimal residual disease assessment in multiple myeloma," *Lancet Oncol.*, 2016; 17(8):e328-46) at Day 1 of every cycle (starting on Cycle 2 Day 1) and at the end of treatment (EOT).

Key efficacy assessments include the following: Myeloma paraprotein (M-protein) in serum and 24-hour urine collections; serum immunoglobulins; serum free light chains; corrected serum calcium; percent of plasma cells in the bone marrow; radiographic assessments of lytic bone lesions; extramedullary plasmacytoma (EMP) assessments; and minimal residual disease (MRD) evaluation by EuroFlow and/or next-generation sequencing (NGS) if sample is evaluable.

Other efficacy variables to be analyzed include overall response rate (ORR), time to response, duration of response (DOR), progression-free survival (PFS), and overall survival (OS).

The efficacy variable of primary interest is myeloma response, including minimal response (MR) and progressive disease according to the IMWG criteria (Kumar, S. et al., 2016 (see above)). Additional variables are summarized including time to response: time from the start of treatment to the first documentation of response (partial response (PR) or better), and duration of response: time from the first documentation of response (PR or better) to the first documentation of progressive disease. Progression-free survival and OS is analyzed in addition to the previous list of endpoints. Efficacy variables are summarized using frequency tabulations for categorical variables or descriptive statistics for time to event endpoints and continuous variables.

Overall Response Rate (ORR). The overall response rate is defined as the proportion of subjects who achieve a partial response or better (eg, PR, very good partial response (VGPR), complete response (CR) or stringent complete response (sCR)), according to IMWG response criteria. Analysis of ORR is based on safety population and efficacy evaluable population. The number and percentage of subjects in the following response categories is presented: stringent complete response (sCR), complete response (CR), sCR+CR, very good partial response (VGPR), partial response (PR), overall response (sCR+CR+VGPR+PR), minimal response (MR), overall response+MR (sCR, CR, VGPR, PR, and MR), stable disease (SD), progressive disease (PD), and not evaluable (NE). The corresponding 90% exact CI for each response category is also provided.

Minimal residual disease (MRD) negative rate is defined as the proportion of subjects who have negative MRD at any timepoint after the first dose. MRD negative rates as assessed by different methods including sustained MRD-negative, flow MRD-negative, sequencing MRD-negative, and imaging plus MRD-negative are reported based on the safety population. The corresponding 90% exact CI is provided.

Time to Response. Time to response is defined as the time from the first study treatment dose date to the date of first documented response (PR or better). This analysis is confined to subjects who have responded. Time to response is summarized using descriptive statistics (mean, standard deviation, median, minimum and maximum) for the safety population.

Duration of Response. Duration of response is defined as the time from the earliest date of documented response (≥PR) to the first documented disease progression or death, whichever occurs first. Duration of response is summarized using Kaplan-Meier estimates. The analysis population is confined to those who have responded. Subjects who neither progress nor die by a data cutoff date are censored at the date of their last adequate tumor assessment. The duration of response is also summarized using descriptive statistics (mean, standard deviation, median, minimum and maximum). Except for the median, which is calculated based on both observed and censored values using the Kaplan-Meier method, all other statistics (mean, standard deviation, minimum and maximum) are calculated based on observed values only.

Progression free Survival. Progression-free survival is defined as the time from the first dose of a study treatment to PD or death from any cause, whichever occurs first. Subjects who neither progress nor die by a data cut-off date are censored at the date of their last adequate tumor assessment. The PFS is summarized using the Kaplan-Meier method for the safety population.

Overall Survival. Overall survival is defined as the time from the first dose of a study treatment to death from any cause. Subjects who are still alive at the clinical cut-off date for the analysis are censored at the last known alive date. The OS is summarized using the Kaplan-Meier method for the safety population.

Table 14 provides study endpoints, including primary, secondary, and exploratory endpoints.

TABLE 14

Study Endpoints.

| Endpoint | Name | Description | Timeframe |
|---|---|---|---|
| Primary | Safety | DLTs and MTD during the DLT evaluation period; AEs evaluated using the NCI CTCAE criteria, Version 5.0 | Dose escalation and dose expansion |
| Secondary | Preliminary efficacy | Determined by IMWG criteria including: ORR Time to response Duration of response PFS OS | Dose escalation and dose expansion |

TABLE 14-continued

Study Endpoints.

| Endpoint | Name | Description | Timeframe |
|---|---|---|---|
| | PK endpoints | $C_{max}$, $C_{min}$, Area under the curve (AUC), $t_{max}$, $t_{1/2}$, CL, $V_{ss}$, and accumulation index of Conjugate 4 (total antibody and ADC) and SC-246 (a catabolite consisting of a maytansinoid warhead-linker-non-natural amino acid, pAMF), which is a component of Conjugate 4, in Arm 1 and Arm 2; BMS-986405 in Arm 2, as appropriate. | Dose escalation and dose expansion |
| | ADA endpoints | Presence and frequency of Conjugate 4 ADA using a validated bridging immunoassay with electrochemiluminescence detection | Dose escalation and dose expansion |
| Exploratory | PD endpoints | Evaluate measures of tumor sensitivity/resistance to Conjugate 4 by measuring depletion of BM plasma cells during treatment by Next-generation flow cytometry (NGF). | Dose escalation and dose expansion |
| | Preliminary efficacy | Evaluate the level of MRD by NGF and/or Next-generation sequencing (NGS). | Dose escalation and dose expansion |
| | Biomarker | Evaluate the percentage of BCMA+ plasma cells and quantitate the level of surface BCMA expression in the bone marrow at baseline by flow cytometry and immunohistochemistry (IHC). | Dose escalation and dose expansion |
| | Biomarker | Evaluate mechanism of action and potential resistance by measuring malignant plasma cell proliferation by flow cytometry and IHC, loss of BCMA target expression, gene signatures by RNAseq, and molecular profiling of tumor cells by NGS. | Dose escalation and dose expansion |
| | PD endpoint | Evaluate levels of circulating sBCMA, APRIL, and BAFF as a surrogate of tumor cell depletion. Evaluate levels of sBCMA as a measure of BMS-986405 activity. | Dose escalation and dose expansion |
| | Biomarker | Exploratory measurements of SARS-CoV-2 serology (anti-SARS-CoV-2 total or IgG) from serum samples collected at baseline and specified timepoints. | Dose escalation and dose expansion |

ADA = anti-Conjugate 4 antibodies;
AE = adverse event;
APRIL = a proliferation inducing ligand;
AUC = area under the serum concentration time-curve;
CL = total body clearance of the drug from the serum;
BAFF = B cell-activating factor;
BCMA = B cell maturation antigen;
BM = bone marrow;
$C_{max}$ = maximum serum concentration of drug;
$C_{min}$ = minimum serum concentration of drug;
DLT = dose-limiting toxicity;
IHC = immunohistochemistry;
IMWG = International Myeloma Working Group;
MRD = minimal residual disease;
MTD = maximum tolerated dose;
NCI CTCAE = National Cancer Institute common terminology criteria for adverse events;
NGF = next generation flow cytometry;
NGS = next generation sequencing
ORR = overall response rate;
OS = overall survival;
PD = pharmacodynamic;
PFS = progression free survival;
PK = pharmacokinetic;
RNASeq = ribonucleic acid sequencing;
sBCMA = soluble B cell maturation antigen;
$t_{1/2}$ = terminal half-life;
$t_{max}$ = time to peak (maximum) serum concentration;
$V_{ss}$ = volume of distribution at steady-state.

EQUIVALENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

One or more features from any embodiments described herein or in the figures may be combined with one or more features of any other embodiments described herein or in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating or preventing cancer in a subject in need thereof, comprising administering to the subject:

a) an effective amount of an antibody conjugate according to the formula:

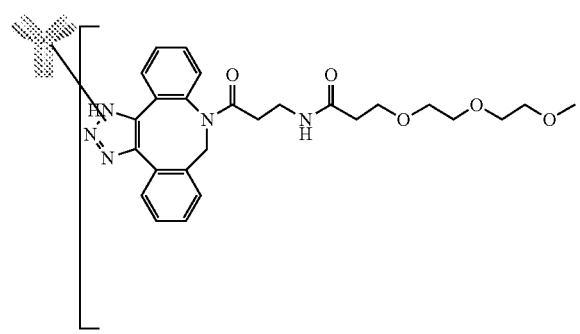

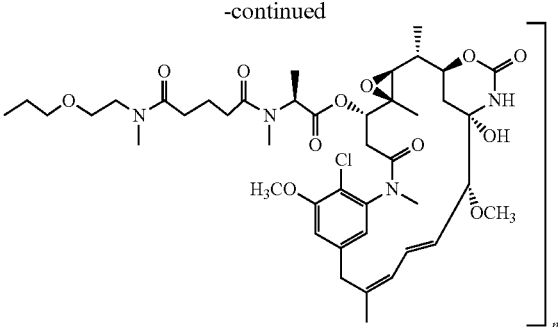

wherein n is from 1 to 4;

the antibody comprises a $V_H$ region of SEQ ID NO: 13, and a $V_L$ region of SEQ ID NO: 14;

the antibody further comprises a constant region domain that comprises a residue of p-azidomethyl-phenylalanine substituting at each of sites HC-F404 and HC-Y180 according to the EU numbering scheme; and each structure within the brackets of the formula is bonded to the antibody at one of the p-azidomethyl-phenylalanine residues, and b) an effective amount of a gamma secretase inhibitor according to the formula:

[Chemical structure]

·H₂O or a pharmaceutically acceptable salt, clathrate, solid form, solvate, stereoisomer, tautomer or racemic mixture thereof.

2. The method of claim 1, wherein the effective amount of the antibody conjugate is about 0.3 mg/kg, 0.6 mg/kg, 1.0 mg/kg, 1.25 mg/kg, 1.5 mg/kg, 1.75 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.25 mg/kg, 4.5 mg/kg, 4.75 mg/kg, 5.0 mg/kg, 5.25 mg/kg, 5.5 mg/kg, 5.75 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.25 mg/kg, 7.5 mg/kg, 7.75 mg/kg, 8.0 mg/kg, 8.25 mg/kg, 8.5 mg/kg, 8.75 mg/kg, 9.0 mg/kg, 9.25 mg/kg, 9.5 mg/kg, 9.75 mg/kg, or 10.0 mg/kg of the subject's body weight.

3. The method of claim 1, wherein the effective amount of the gamma secretase inhibitor is about 25 mg.

4. The method of claim 1, wherein the effective amount of the antibody conjugate is administered to the subject once every three weeks and the effective amount of the gamma secretase inhibitor is administered to the subject three times every week during a 21-day cycle.

5. The method of claim 4, wherein the effective amount of the antibody conjugate is administered to the subject on Day 1 of the 21-day cycle, and wherein the effective amount of the antibody conjugate is 0.3 mg/kg, 0.6 mg/kg, 1.25 mg/kg, 2.0 mg/kg, 3.0 mg/kg, 4.5 mg/kg, or 6.7 mg/kg.

6. The method of claim 5, wherein the effective amount of the gamma secretase inhibitor is administered to the subject on Day 1, Day 3, Day 5, Day 8, Day 10, Day 12, Day 15, Day 17, and Day 19 of the 21-day cycle.

7. The method of claim 1, wherein the effective amount of the antibody conjugate is administered intravenously.

8. The method of claim 1, wherein n is 4.

9. The method of claim 1, wherein the constant region comprises a sequence selected from SEQ ID NO: 19, SEQ ID NO: 20, or both.

10. The method of claim 1, wherein:
a. the antibody is a monoclonal antibody;
b. the antibody is an IgA, an IgD, an IgE, an IgG, or an IgM;
c. the antibody is humanized or human;
d. the antibody is aglycosylated; or
e. the antibody is an antibody fragment.

11. The method of claim 10, wherein the antibody is an antibody fragment, and wherein the antibody fragment is selected from an Fv fragment, a Fab fragment, a F(ab')₂ fragment, a Fab' fragment, an scFv (sFv) fragment, and an scFv-Fc fragment.

12. The method of claim 1, wherein the antibody specifically binds cynomolgus BCMA or mouse BCMA.

13. The method of claim 1, wherein the antibody conjugate is administered concurrently with the gamma secretase inhibitor.

14. The method of claim 1, wherein the antibody conjugate is administered prior to or after the administration of the gamma secretase inhibitor.

15. The method of claim 1, wherein the antibody conjugate and the gamma secretase inhibitor are administered on an empty stomach.

16. The method of claim 1, wherein the antibody conjugate and the gamma secretase inhibitor are administered on an full stomach.

17. The method of claim 1, wherein the cancer is leukemia or lymphoma.

18. The method of claim 1, wherein the cancer is multiple myeloma.

19. The method of claim 18, wherein said multiple myeloma is;
a. Stage I according to the International Staging System or the Revised International Staging System;
b. Stage II according to the International Staging System or the Revised International Staging System;
c. Stage III according to the International Staging System or the Revised International Staging System; or
d. newly-diagnosed multiple myeloma.

20. The method of claim 18, wherein said multiple myeloma is relapsed or refractory multiple myeloma.

21. A kit comprising:
a) one or more doses of an antibody conjugate according to the formula:

[Chemical structure]

wherein n is from 1 to 4;
the antibody comprises a V_H region of SEQ ID NO: 13, and a V_L region of SEQ ID NO: 14;
the antibody further comprises a constant region domain that comprises a residue of p-azidomethyl-phenylalanine substituting at each of sites HC-F404 and HC-Y180 according to the EU numbering scheme; and each structure within the brackets of the formula is bonded to the antibody at one of the p-azidomethyl-phenylalanine residues, and b) one or more doses of a gamma secretase inhibitor, according to the formula:

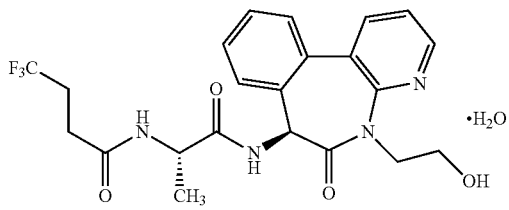

or a pharmaceutically acceptable salt, clathrate, solid form, solvate, stereoisomer, tautomer or racemic mixture thereof, and instructions for use of the antibody conjugate and the gamma secretase inhibitor.

22. The kit of claim 21, wherein:
a. the antibody conjugate is lyophilized; or
b. the antibody conjugate is lyophilized and further comprises a fluid for reconstitution of the lyophilized antibody conjugate.

23. The kit of claim 21, wherein:
a. the antibody conjugate is present in an amount that comprises from about 10 mg to about 1000 mg;
b. the gamma secretase inhibitor is present in an amount that comprises about 25 mg; or
c. the antibody conjugate is present in an amount that comprises from about 10 mg to about 1000 mg and the gamma secretase inhibitor is present in an amount that comprises about 25 mg.

24. The kit of claim 21, wherein:
a. the kit comprises one or more containers comprising the antibody conjugate and the gamma secretase inhibitor; or
b. the antibody conjugate and the gamma secretase inhibitor are in separate containers.

25. The method of claim 2, wherein the effective amount of the gamma secretase inhibitor is about 25 mg.

* * * * *

```
                           SEQUENCE LISTING

<160> NUMBER OF SEQ ID NOS: 28

<210> SEQ ID NO 1
<211> LENGTH: 184
<212> TYPE: PRT
<213> ORGANISM: Homo sapiens
<220> FEATURE:
<223> OTHER INFORMATION: Human BCMA (Isoform1)

<400> SEQUENCE: 1

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 2
<211> LENGTH: 135
<212> TYPE: PRT
<213> ORGANISM: Homo sapiens
<220> FEATURE:
<223> OTHER INFORMATION: Human BCMA (Isoform2)

<400> SEQUENCE: 2

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Arg Ser Gly Leu Leu
        35                  40                  45

Gly Met Ala Asn Ile Asp Leu Glu Lys Ser Arg Thr Gly Asp Glu Ile
    50                  55                  60

Ile Leu Pro Arg Gly Leu Glu Tyr Thr Val Glu Glu Cys Thr Cys Glu
65                  70                  75                  80

Asp Cys Ile Lys Ser Lys Pro Lys Val Asp Ser Asp His Cys Phe Pro
```

85                  90                  95

Leu Pro Ala Met Glu Glu Gly Ala Thr Ile Leu Val Thr Thr Lys Thr
                100                 105                 110

Asn Asp Tyr Cys Lys Ser Leu Pro Ala Ala Leu Ser Ala Thr Glu Ile
            115                 120                 125

Glu Lys Ser Ile Ser Ala Arg
        130                 135

<210> SEQ ID NO 3
<211> LENGTH: 183
<212> TYPE: PRT
<213> ORGANISM: Macaca fascicularis
<220> FEATURE:
<223> OTHER INFORMATION: Cynomolgus BCMA

<400> SEQUENCE: 3

Met Leu Gln Met Ala Arg Gln Cys Ser Gln Asn Glu Tyr Phe Asp Ser
1               5                   10                  15

Leu Leu His Asp Cys Lys Pro Cys Gln Leu Arg Cys Ser Ser Thr Pro
                20                  25                  30

Pro Leu Thr Cys Gln Arg Tyr Cys Asn Ala Ser Met Thr Asn Ser Val
            35                  40                  45

Lys Gly Met Asn Ala Ile Leu Trp Thr Cys Leu Gly Leu Ser Leu Ile
    50                  55                  60

Ile Ser Leu Ala Val Phe Val Leu Thr Phe Leu Leu Arg Lys Met Ser
65                  70                  75                  80

Ser Glu Pro Leu Lys Asp Glu Phe Lys Asn Thr Gly Ser Gly Leu Leu
                85                  90                  95

Gly Met Ala Asn Ile Asp Leu Glu Lys Gly Arg Thr Gly Asp Glu Ile
                100                 105                 110

Val Leu Pro Arg Gly Leu Glu Tyr Thr Val Glu Glu Cys Thr Cys Glu
            115                 120                 125

Asp Cys Ile Lys Asn Lys Pro Lys Val Asp Ser Asp His Cys Phe Pro
        130                 135                 140

Leu Pro Ala Met Glu Glu Gly Ala Thr Ile Leu Val Thr Thr Lys Thr
145                 150                 155                 160

Asn Asp Tyr Cys Asn Ser Leu Ser Ala Ala Leu Ser Val Thr Glu Ile
                165                 170                 175

Glu Lys Ser Ile Ser Ala Arg
            180

<210> SEQ ID NO 4
<211> LENGTH: 185
<212> TYPE: PRT
<213> ORGANISM: Mus musculus
<220> FEATURE:
<223> OTHER INFORMATION: Murine BCMA

<400> SEQUENCE: 4

Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Pro Ala Thr Cys
                20                  25                  30

Gln Pro Tyr Cys Asp Pro Ser Val Thr Ser Ser Val Lys Gly Thr Tyr
            35                  40                  45

Thr Val Leu Trp Ile Phe Leu Gly Leu Thr Leu Val Leu Ser Leu Ala
    50                  55                  60

```
Leu Phe Thr Ile Ser Phe Leu Leu Arg Lys Met Asn Pro Glu Ala Leu
 65                  70                  75                  80

Lys Asp Glu Pro Gln Ser Pro Gly Gln Leu Asp Gly Ser Ala Gln Leu
                 85                  90                  95

Asp Lys Ala Asp Thr Glu Leu Thr Arg Ile Arg Ala Gly Asp Asp Arg
            100                 105                 110

Ile Phe Pro Arg Ser Leu Glu Tyr Thr Val Glu Glu Cys Thr Cys Glu
        115                 120                 125

Asp Cys Val Lys Ser Lys Pro Lys Gly Asp Ser Asp His Phe Phe Pro
    130                 135                 140

Leu Pro Ala Met Glu Glu Gly Ala Thr Ile Leu Val Thr Thr Lys Thr
145                 150                 155                 160

Gly Asp Tyr Gly Lys Ser Ser Val Pro Thr Ala Leu Gln Ser Val Met
                165                 170                 175

Gly Met Glu Lys Pro Thr His Thr Arg
                180                 185

<210> SEQ ID NO 5
<211> LENGTH: 7
<212> TYPE: PRT
<213> ORGANISM: Artificial Sequence
<220> FEATURE:
<223> OTHER INFORMATION: 2265-F02, CDR-H1, Chothia

<400> SEQUENCE: 5

Gly Phe Asn Ile Ser Ala Pro
1               5

<210> SEQ ID NO 6
<211> LENGTH: 5
<212> TYPE: PRT
<213> ORGANISM: Artificial Sequence
<220> FEATURE:
<223> OTHER INFORMATION: 2265-F02, CDR-H1, Kabat

<400> SEQUENCE: 6

Ala Pro Gly Ile His
1               5

<210> SEQ ID NO 7
<211> LENGTH: 6
<212> TYPE: PRT
<213> ORGANISM: Artificial Sequence
<220> FEATURE:
<223> OTHER INFORMATION: 2265-F02, CDR-H2, Chothia

<400> SEQUENCE: 7

Asn Pro Ala Gly Gly Tyr
1               5

<210> SEQ ID NO 8
<211> LENGTH: 17
<212> TYPE: PRT
<213> ORGANISM: Artificial Sequence
<220> FEATURE:
<223> OTHER INFORMATION: 2265-F02, CDR-H2, Kabat

<400> SEQUENCE: 8

Phe Ile Asn Pro Ala Gly Gly Tyr Thr Asp Tyr Ala Asp Ser Val Lys
1               5                   10                  15

Gly
```

```
<210> SEQ ID NO 9
<211> LENGTH: 13
<212> TYPE: PRT
<213> ORGANISM: Artificial Sequence
<220> FEATURE:
<223> OTHER INFORMATION: 2265-F02, CDR-H3

<400> SEQUENCE: 9

Asp Tyr Ile Arg Gln Tyr Trp Thr Tyr Val Leu Asp Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: trastuzumab, CDR-L1

<400> SEQUENCE: 10

Arg Ala Ser Gln Asp Val Asn Thr Ala Val Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: trastuzumab, CDR-L2

<400> SEQUENCE: 11

Ser Ala Ser Phe Leu Tyr Ser
1               5

<210> SEQ ID NO 12
<211> LENGTH: 9
<212> TYPE: PRT
<213> ORGANISM: Artificial Sequence
<220> FEATURE:
<223> OTHER INFORMATION: trastuzumab, CDR-L3

<400> SEQUENCE: 12

Gln Gln His Tyr Thr Thr Pro Pro Thr
1               5

<210> SEQ ID NO 13
<211> LENGTH: 122
<212> TYPE: PRT
<213> ORGANISM: Artificial Sequence
<220> FEATURE:
<223> OTHER INFORMATION: 2265-F02, VH

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ala Pro
            20                  25                  30

Gly Ile His Trp Val Arg Gln Ala Pro Gly Lys Gly Leu Glu Trp Val
        35                  40                  45

Gly Phe Ile Asn Pro Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ala Arg Asp Tyr Ile Arg Gln Tyr Trp Thr Tyr Val Leu Asp Tyr Trp
                100                 105                 110

Gly Gln Gly Thr Leu Val Thr Val Ser Ser
        115                 120
```

<210> SEQ ID NO 14
<211> LENGTH: 107
<212> TYPE: PRT
<213> ORGANISM: Artificial Sequence
<220> FEATURE:
<223> OTHER INFORMATION: trastuzumab, VL

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 15
<211> LENGTH: 452
<212> TYPE: PRT
<213> ORGANISM: Artificial Sequence
<220> FEATURE:
<223> OTHER INFORMATION: 2265-F02, Heavy Chain

<400> SEQUENCE: 15

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ala Pro
            20                  25                  30

Gly Ile His Trp Val Arg Gln Ala Pro Gly Lys Gly Leu Glu Trp Val
        35                  40                  45

Gly Phe Ile Asn Pro Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Tyr Ile Arg Gln Tyr Trp Thr Tyr Val Leu Asp Tyr Trp
                100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

```
Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 16
<211> LENGTH: 1356
<212> TYPE: DNA
<213> ORGANISM: Artificial Sequence
<220> FEATURE:
<223> OTHER INFORMATION: 2265-F02, Heavy Chain

<400> SEQUENCE: 16
gaagttcagt tagtggaatc aggcggcggt ttagttcaac caggcggttc attgcgtctg      60
tcatgcgcgg cttccggttt caacatcagt gcgcctggga tccattgggt gcgtcaggcc     120
ccaggcaagg gtctggagtg ggtcggtttt atcaatcctg ctggcggtta taccgactat     180
gcggactctg tgaagggtcg cttcaccatt agcgcggata cctcgaagaa tacggcgtat     240
ttacagatga attccctgcg tgcagaggac actgccgtct actattgtgc gcgcgattac     300
attcggcagt actggaccta cgttcttgac tactggggcc agggtacgct ggtcaccgtg     360
tcgtcggcgt caaccaaggg tccgtcggtt tttccgctgg cgccgtcgtc aaaatctacg     420
```

```
tccggtggta ccgccgctct gggttgcctg gttaaagact actttccgga gccggtcacg    480
gtttcgtgga actctggtgc cctgacttct ggcgtccaca cgttcccagc cgttttgcag    540
tcatccggtc tgtagtcgtt gtcctctgtg gtcacggtgc cgtcatcgtc tctgggcacc    600
caaacctata tctgcaatgt caaccacaaa ccgtccaata cgaaagttga caaaaaagtc    660
gagccgaaat cttgcgacaa gacccacacg tgccctccgt gccggcaccg gaactgctg     720 ggcggtccgt cggtgttcct gttcccgccg aagccgaaag atactctgat gatctcacgt    780
accccggaag tcacgtgtgt tgttgttgac gtgtcacacg aagatccaga ggtgaaattc    840
aattggtatg tggacggtgt cgaagtgcat aatgccaaaa ccaaaccgcg cgaggaacag    900
tacaactcca cctaccgcgt cgtgtcggtg ttgaccgtcc tgcatcaaga ctggctgaac    960
ggtaaagagt acaagtgcaa ggtttcaaat aaggcactgc ctgcgccgat tgaaaagacc   1020
atctctaagg caaagggcca gccgcgtgag ccacaggtgt ataccctgcc gccgtcgcgt   1080
gaagaaatga ccaagaacca agtttcactg acgtgtctgg tcaagggctt ttatccgtcc   1140
gatattgcgg tggagtggga gtctaatggc cagccggaaa acaattacaa aacgactccg   1200
ccggtgctgg attccgacgg ttcgtagttc ctgtattcca agctgaccgt tgacaaatca   1260
cgttggcagc aaggcaacgt tttttcttgt tcggtaatgc acgaagcgct gcacaatcat   1320
tacacccaga atcactgtc gttgtctccg ggcaaa                              1356
```

```
<210> SEQ ID NO 17
<211> LENGTH: 214
<212> TYPE: PRT
<213> ORGANISM: Artificial Sequence
<220> FEATURE:
<223> OTHER INFORMATION: 2265-F02, Light Chain

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

Phe Asn Arg Gly Glu Cys
          210

<210> SEQ ID NO 18
<211> LENGTH: 642
<212> TYPE: DNA
<213> ORGANISM: Artificial Sequence
<220> FEATURE:
<223> OTHER INFORMATION: 2265-F02, Light Chain

<400> SEQUENCE: 18

```
gacattcaaa tgacccagtc tccgtcgtca ctgtccgcat ccgttggcga ccgcgttacc      60
atcacgtgcc gtgcgtcgca agatgtgaac accgccgtgg cgtggtatca gcaaaaaccg     120
ggcaaagctc cgaagctgct gatctattca gcctctttcc tgtactcggg tgttccgtcc     180
cgtttctcag gctctcgctc gggtacggat ttcaccctga ctatttcttc actgcaaccg     240
gaagattttg cgacgtacta ctgtcagcag cattacacga ctccgccgac ctttggtcag     300
ggtaccaagg tcgagattaa gcgtaccgtg gctgcaccat ccgtgtttat cttccctccg     360
tctgatgagc agctgaaatc cggtacggcg tcggtcgtct gcttgctgaa taacttctat     420
ccgcgtgaag cgaaggtgca atggaaggtt gacaatgccc tgcagtcagg taactcccaa     480
gagtctgtta ccgaacaaga ttcgaaagac tcaacctact ccctgtcttc gacgctgacg     540
ttgtccaaag cggactatga gaaacacaag gtttacgcat gtgaagtgac ccaccagggc     600
ctgtcatctc cggtcaccaa atcatttaat cgcggtgagt gc                       642
```

<210> SEQ ID NO 19
<211> LENGTH: 330
<212> TYPE: PRT
<213> ORGANISM: Homo sapiens
<220> FEATURE:
<223> OTHER INFORMATION: Human IgG1 HC Constant

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 107
<212> TYPE: PRT
<213> ORGANISM: Homo sapiens
<220> FEATURE:
<223> OTHER INFORMATION: Human IgG LC Constant Ckappa

<400> SEQUENCE: 20

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 21
<211> LENGTH: 323
<212> TYPE: PRT
<213> ORGANISM: Mus musculus
<220> FEATURE:
<223> OTHER INFORMATION: Mouse IgG1 HC Constant

<400> SEQUENCE: 21

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
```

```
            35                  40                  45
Gly Val His Thr Phe Pro Ala Val Leu Gln Ser Asp Leu Tyr Thr Leu
 50                  55                  60
Ser Ser Ser Val Thr Val Pro Ser Ser Thr Trp Pro Ser Glu Thr Val
 65                  70                  75                  80
Thr Cys Asn Val Ala His Pro Ala Ser Ser Thr Lys Val Asp Lys Lys
                     85                  90                  95
Ile Val Pro Arg Asp Cys Gly Cys Lys Pro Cys Ile Cys Thr Val Pro
             100                 105                 110
Glu Val Ser Ser Val Phe Ile Phe Pro Pro Lys Pro Lys Asp Val Leu
             115                 120                 125
Thr Ile Thr Leu Thr Pro Lys Val Thr Cys Val Val Val Asp Ile Ser
130                 135                 140
Lys Asp Asp Pro Glu Val Gln Phe Ser Trp Phe Val Asp Asp Val Glu
145                 150                 155                 160
Val His Thr Ala Gln Thr Gln Pro Arg Glu Glu Gln Phe Asn Ser Thr
                 165                 170                 175
Phe Arg Ser Val Ser Glu Leu Pro Ile Met His Gln Asp Trp Leu Asn
             180                 185                 190
Gly Lys Glu Phe Lys Cys Arg Val Asn Ser Ala Ala Phe Pro Ala Pro
             195                 200                 205
Ile Glu Lys Thr Ile Ser Lys Thr Lys Gly Arg Pro Lys Ala Pro Gln
210                 215                 220
Val Tyr Thr Ile Pro Pro Pro Lys Glu Gln Met Ala Lys Asp Lys Val
225                 230                 235                 240
Ser Leu Thr Cys Met Ile Thr Asp Phe Phe Pro Glu Asp Ile Thr Val
                 245                 250                 255
Glu Trp Gln Trp Asn Gly Gln Pro Ala Glu Asn Tyr Lys Asn Thr Gln
             260                 265                 270
Pro Ile Met Asp Thr Asp Gly Ser Tyr Phe Val Tyr Ser Lys Leu Asn
             275                 280                 285
Val Gln Lys Ser Asn Trp Glu Ala Gly Asn Thr Phe Thr Cys Ser Val
290                 295                 300
Leu His Glu Gly Leu His Asn His His Thr Glu Lys Ser Leu Ser His
305                 310                 315                 320
Ser Pro Gly

<210> SEQ ID NO 22
<211> LENGTH: 107
<212> TYPE: PRT
<213> ORGANISM: Mus musculus
<220> FEATURE:
<223> OTHER INFORMATION: Mouse IgG LC Constant Ckappa

<400> SEQUENCE: 22

Arg Ala Asp Ala Ala Pro Thr Val Ser Ile Phe Pro Pro Ser Ser Glu
 1               5                  10                  15
Gln Leu Thr Ser Gly Gly Ala Ser Val Val Cys Phe Leu Asn Asn Phe
                 20                  25                  30
Tyr Pro Lys Asp Ile Asn Val Lys Trp Lys Ile Asp Gly Ser Glu Arg
             35                  40                  45
Gln Asn Gly Val Leu Asn Ser Trp Thr Asp Gln Asp Ser Lys Asp Ser
 50                  55                  60
Thr Tyr Ser Met Ser Ser Thr Leu Thr Leu Thr Lys Asp Glu Tyr Glu
 65                  70                  75                  80
```

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 23
<211> LENGTH: 108
<212> TYPE: PRT
<213> ORGANISM: Artificial Sequence
<220> FEATURE:
<223> OTHER INFORMATION: Kappa LC

<400> SEQUENCE: 23

His Met Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 24
<211> LENGTH: 106
<212> TYPE: PRT
<213> ORGANISM: Artificial Sequence
<220> FEATURE:
<223> OTHER INFORMATION: Lambda LD

<400> SEQUENCE: 24

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 25
<211> LENGTH: 20
<212> TYPE: PRT
<213> ORGANISM: Artificial Sequence
<220> FEATURE:
<223> OTHER INFORMATION: FlagHis Tag

<400> SEQUENCE: 25

```
Gly Ser Gly Asp Tyr Lys Asp Asp Asp Lys Gly Ser Gly His His
1               5                   10                  15

His His His His
            20

<210> SEQ ID NO 26
<211> LENGTH: 15
<212> TYPE: PRT
<213> ORGANISM: Artificial Sequence
<220> FEATURE:
<223> OTHER INFORMATION: Linker

<400> SEQUENCE: 26

Gly Gly Gly Gly Ser Gly Gly Gly Gly Ser Gly Gly Gly Gly Ser
1               5                   10                  15

<210> SEQ ID NO 27
<211> LENGTH: 11
<212> TYPE: PRT
<213> ORGANISM: Artificial Sequence
<220> FEATURE:
<223> OTHER INFORMATION: Linker

<400> SEQUENCE: 27

Ala Ala Gly Ser Asp Gln Glu Pro Lys Ser Ser
1               5                   10

<210> SEQ ID NO 28
<211> LENGTH: 30
<212> TYPE: PRT
<213> ORGANISM: Artificial Sequence
<220> FEATURE:
<223> OTHER INFORMATION: Linker
<220> FEATURE:
<221> NAME/KEY: MISC_FEATURE
<222> LOCATION: (16)..(30)
<223> OTHER INFORMATION: "Gly Gly Gly Gly Ser" may or may not be present

<400> SEQUENCE: 28

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```